United States Patent
Hsieh et al.

(10) Patent No.: US 8,916,504 B2
(45) Date of Patent: Dec. 23, 2014

(54) METHODS OF RNA DISPLAY

(75) Inventors: Chung-Ming Hsieh, Newton, MA (US); Yuliya A. Kutskova, Northborough, MA (US); John E. Memmott, Framingham, MA (US)

(73) Assignee: Abbvie Inc., North Chicago, IL (US)

( * ) Notice: Subject to any disclaimer, the term of this patent is extended or adjusted under 35 U.S.C. 154(b) by 3 days.

(21) Appl. No.: 12/570,931

(22) Filed: Sep. 30, 2009

(65) Prior Publication Data

US 2010/0105569 A1 Apr. 29, 2010

Related U.S. Application Data

(60) Provisional application No. 61/101,471, filed on Sep. 30, 2008.

(51) Int. Cl.
*C40B 30/04* (2006.01)
*C07K 17/00* (2006.01)

(52) U.S. Cl.
USPC .................. 506/9; 506/7; 506/13; 530/391.3; 530/391.5; 530/412

(58) Field of Classification Search
USPC .............................................. 506/9; 530/412
See application file for complete search history.

(56) References Cited

U.S. PATENT DOCUMENTS

| | | | |
|---|---|---|---|
| 5,310,652 A | 5/1994 | Gelfand et al. | |
| 5,580,757 A | 12/1996 | Desnick et al. | |
| 5,922,545 A | 7/1999 | Mattheakis et al. | |
| 6,914,128 B1 | 7/2005 | Salfeld | |
| 6,927,025 B1 | 8/2005 | Carr et al. | |
| 7,074,557 B2 | 7/2006 | Osbourn et al. | |
| 7,264,932 B2 | 9/2007 | Latham et al. | |
| 7,662,926 B2 * | 2/2010 | Chan et al. | 530/387.1 |
| 7,749,957 B2 * | 7/2010 | Ittel et al. | 514/18.8 |
| 8,183,347 B2 * | 5/2012 | Liang et al. | 530/387.3 |
| 2004/0018536 A1 | 1/2004 | Yanagawa et al. | |
| 2005/0042623 A1 | 2/2005 | Ault-Riche et al. | |
| 2005/0123900 A1 | 6/2005 | Dimitrov et al. | |
| 2005/0232936 A1 | 10/2005 | Arico et al. | |
| 2006/0246515 A1 | 11/2006 | Zhu et al. | |
| 2006/0246549 A1 | 11/2006 | Kurz et al. | |
| 2007/0160533 A1 * | 7/2007 | Chen et al. | 424/1.69 |
| 2007/0218478 A1 | 9/2007 | Bai et al. | |
| 2007/0269879 A1 | 11/2007 | Saribas et al. | |
| 2008/0050370 A1 | 2/2008 | Glaser et al. | |
| 2008/0058217 A1 * | 3/2008 | Szostak et al. | 506/9 |
| 2009/0136986 A1 * | 5/2009 | Church et al. | 435/29 |
| 2011/0160289 A1 * | 6/2011 | Astatke et al. | 514/44 R |

OTHER PUBLICATIONS

International Search Report and Written Opinion for Application No. PCT/US09/59057, dated Jan. 13, 2010.
Irving R A et al: "Ribosome Display and Affinity Maturation: From Antibodies to Single V-Domains and Steps Towards Cancer Therapeutics", Journal of Immunological Methods, Elsevier Science Publishers B.V., Amsterdam, NL, vol. 248, No. 1/02, Feb. 1, 2001, pp. 31-45, XP001147978.
Kurz M et al: "Psoralen photo-crosslinked mRNA-puromycin conjugates: a novel template for the rapid and facile preparation of mRNA-protein fusions.", Nucleic Acids Research Sep. 15, 2000 LNKD-PUBMED: 10982894, vol. 28, No. 18, Sep. 15, 2000, p. E83, XP002300717.
Supplementary European Search Report from EP 09 81 8450 dated Feb. 7, 2012.

* cited by examiner

*Primary Examiner* — Teresa Wessendorf
(74) *Attorney, Agent, or Firm* — Lathrop & Gage LLP; James H. Velema, Esq.

(57) ABSTRACT

The present invention features improved methods of in vitro RNA display to allow reliable expression and selection of scFv antibody molecules from expression libraries. The improved methods, in part, involve the use of mildly reducing conditions, which favor of scFv intra-chain disulphide bond and thus correct folding of the scFv antibody molecules. Although particularly suited to expression and selection of scFv antibody molecules, the methods of the invention are also expedient for in vitro RNA display of all classes of protein.

35 Claims, 24 Drawing Sheets

| T7 | TMV-UTR | TK | VH | GS | VL | C | FLAG | Linker | PolyA |

17/9-short
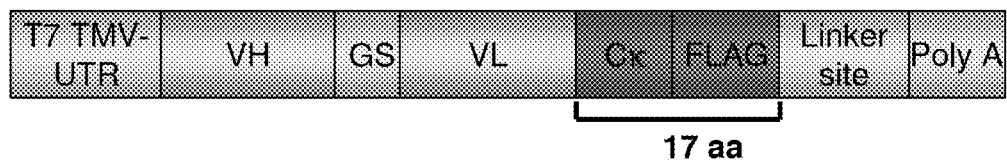
17 aa
17/9-long
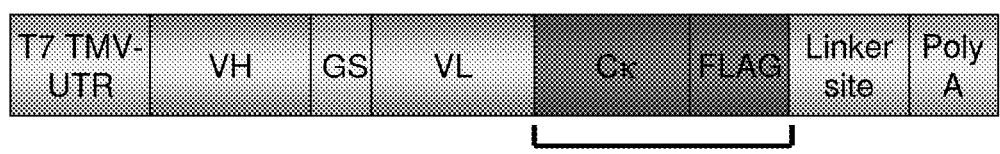
113 aa
*Fig. 9a*
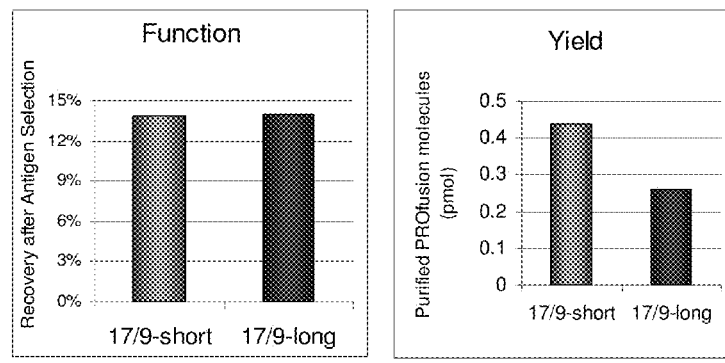
*Fig. 9b*

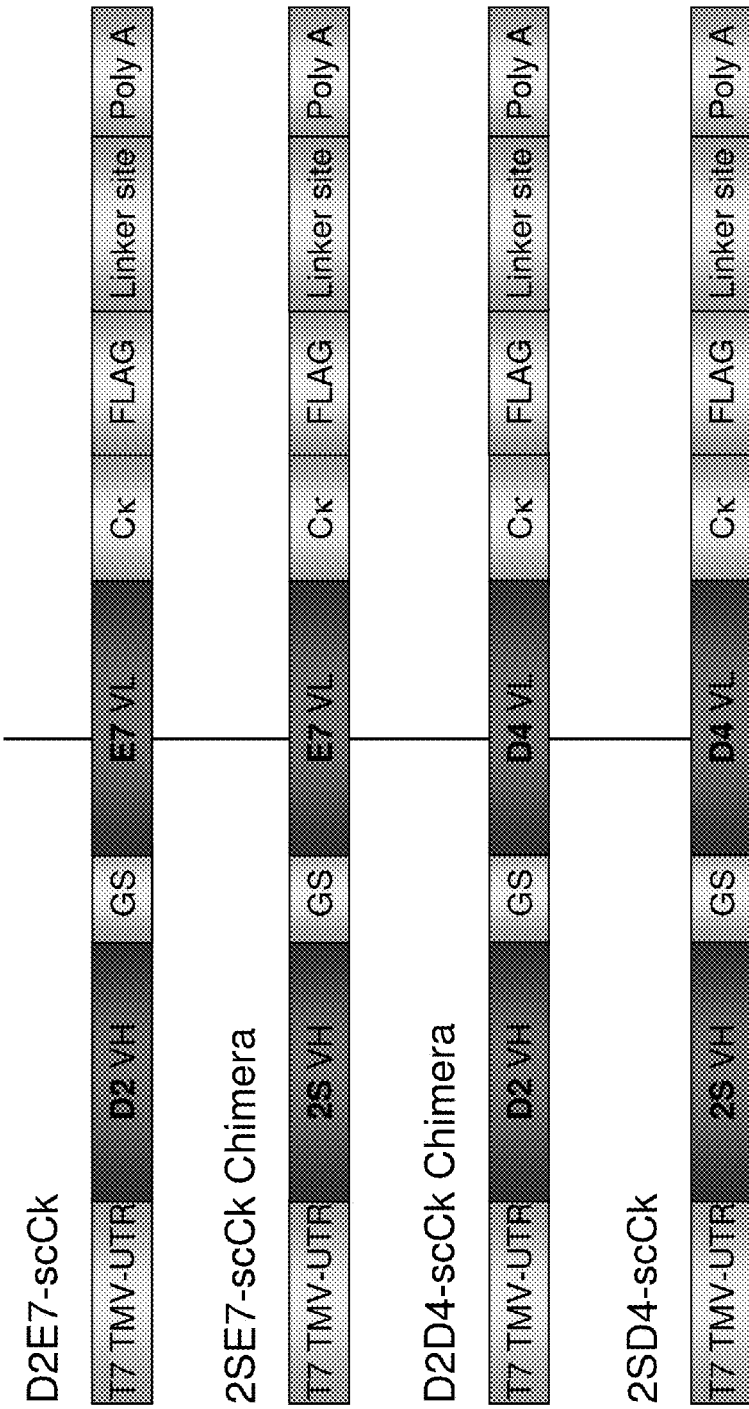

METHODS OF RNA DISPLAY

RELATED APPLICATIONS

This application claims priority to U.S. Provisional Application No. 61/101,471, filed Sep. 30, 2008, the contents of which are hereby incorporated by reference.

FIELD OF THE INVENTION

The present disclosure relates to RNA display, and particularly to methods of RNA display that allow selection of soluble and cell surface antigens.

BACKGROUND OF THE INVENTION

Antibodies can be selected that bind with high specificity and affinity to almost any structural epitope and are routinely used as research tools and as FDA approved therapeutics. As a result, therapeutic and diagnostic monoclonal antibodies constitute a multi-billion dollar market worldwide.

Classical methods of immunizing animals to obtain antibodies are slow and cumbersome. As a consequence, methods have been developed for ex vivo selection of an antibody to a desired target molecule using synthetic antibody libraries. In some methods, libraries of antibodies, or fragments thereof, are displayed on the surface of an organism, (for example, a bacteriophage, virus, yeast cell, bacterial cell or mammalian cell), and the organism is selected for expression of the desired antibody. In other methods, antibody libraries are expressed and selected in a cell free in vitro system. In one such system, termed RNA display, expressed proteins or peptides are linked covalently or by tight non-covalent interaction to their encoding mRNA to form RNA/protein fusion molecules. The protein or peptide component of an RNA/protein fusion can be selected for binding to a desired target and the identity of the protein or peptide determined by sequencing of the attached encoding mRNA component.

Current in vitro RNA display systems, although good at expressing single antibody variable domains, are inefficient at expressing multi-domain antibodies such as single chain antibody (scFv) molecules. This is mainly due to the reaction conditions of the current in vitro expression systems and the tendency to lose full length scFv cDNA from the library through repeated amplification by PCR.

There is, therefore, a need in the art for improved in vitro display methods for selection of scFv antibodies against a desired target.

SUMMARY OF THE INVENTION

The invention solves the foregoing problems by providing improved methods of in vitro RNA display to allow reliable expression and selection of scFv molecules from expression libraries. Although, particularly suited to expression and selection of scFv molecules, the methods of the invention are also expedient for in vitro display of all classes of protein, including both soluble and cell surface antigens.

Accordingly the invention has several advantages which include, but are not limited to, providing improved in vitro RNA display methods that are simpler and less time consuming to perform than previously described methods. Additionally, the methods of the invention allow for enhanced functional expression of proteins containing intra-chain disulphide bonds, for example, scFv antibody molecules.

In one aspect, the invention provides a method of screening an scFv antibody RNA display library, the method comprising the steps of (a) providing a puromycin or analogue thereof crosslinked scFv mRNA molecule, said molecule comprising an mRNA encoding a 5' scFv and a 3' spacer sequence, which molecule is crosslinked to a single stranded nucleic acid linker, the linker comprising a puromycin, or analogue thereof, at a 3' end and a Psoralen C6 at the 5' end; (b) in vitro translating the puromycin-crosslinked scFv mRNA in the presence of a label, in the presence of oxidized glutathione/reduced glutathione and PDI (protein disulphide isomerase) and in the absence of dithiothreitol under conditions such that a labeled puromycin-crosslinked scFv mRNA/protein molecule is formed; (c) purifying the labeled puromycin-crosslinked scFv mRNA/protein molecule; (d) subjecting the purified labeled puromycin-crosslinked scFv mRNA/protein molecule to antigen selection with at least one antigen; and (e) recovering the purified labeled puromycin-crosslinked scFv mRNA/protein molecules using affinity based magnetic beads.

In an embodiment, the method further comprises the step of (g) reverse transcribing the scFv mRNA after antigen selection to make a cDNA. In another embodiment, the method further comprises the step of (h) amplifying the cDNA.

In an embodiment, the label is a radioactive label, such as, for example, $^{35}S$ methionine or cysteine.

In an embodiment, the 3' spacer sequence comprises about 0 to about 200 amino acids, for example, about 16 amino acids, and/or the 3' spacer comprises an affinity tag.

In an embodiment, the linker comprises, from 5' to 3': Psoralen C6, 2'OMe ribonucleotides comprising the sequence UAGCGGAUGC (SEQ ID NO: 20), six Triethylene glycol or PEG-150 moieties, two cytidine residues, and puromycin.

In an embodiment, the scFv mRNA molecule is photocrosslinked to the DNA linker by UVA. In another embodiment, the scFv mRNA molecule comprises a 5' promoter selected from the group consisting of T7, SP6, and T3. In a particular embodiment, the scFv mRNA molecule comprises a tobacco mosaic virus 5' untranslated region.

In an embodiment, the labeled puromycin-crosslinked scFv mRNA/protein molecule is purified by oligo-dT chromatography. In another embodiment, labeled puromycin-crosslinked scFv mRNA/protein molecule is purified using anti-FLAG M2 monoclonal antibody agarose beads. In yet another embodiment, the labeled puromycin-crosslinked scFv mRNA/protein molecule is purified by oligo-dT chromatography and anti-FLAG M2 monoclonal antibody agarose beads.

In an embodiment, the antigen is a biotinylated peptide, protein, or hapten. In another embodiment, the antigen is a fusion protein with human immunoglobulin fragment crystallizable (Fc) or with murine immunoglobulin fragment crystallizable (Fc), or the antigen is a population of cells. In a particular embodiment, the antibody according to the invention is an anti-IL-12 antibody, an anti-hemaglutinin (anti-HA) antibody, a murine antibody, or a human antibody.

In an embodiment, the in vitro translation of the puromycin-crosslinked scFv mRNA is performed in the presence of oxidized glutathione/reduced glutathione.

In an embodiment, the method does not comprise an mRNA capping step. In another embodiment, the method does not comprise an in vitro reverse transcription step prior to the purification step. In yet another embodiment, an RNase inhibitor is added before, during, or after any of steps (a) through (g). In an embodiment, the purification step comprises reverse transcription of the mRNA in the absence of dithiothreitol (DTT) to produce a cDNA.

In certain embodiments, the cDNA is eluted by alkaline hydrolysis at about pH=8.0 to about pH=10.0. Alternatively, the cDNA is eluted by heat sufficient to denature DNA:RNA hybrids, by acid at about pH=3.0 to about pH=6.0, or by RNase H digestion.

In an embodiment, the cDNA is amplified by polymerase chain reaction. In an embodiment, the polymerization chain reaction employs a thermostable DNA polymerase or DNA polymerases selected from the group consisting of Platinum HiFi and KOD.

In another embodiment, the beads are selected from the group consisting of streptavidin-M280, neutravidin-M280, SA-M270, NA-M270, SA-MyOne, NA-MyOne, SA-agarose, and NA-agarose.

Other features and advantages of the invention will be apparent from the following detailed description and claims.

BRIEF DESCRIPTION OF THE DRAWINGS

FIG. 3 depicts a general depiction of the library DNA construct.

FIG. 8 depicts the sequences of the D2E7 short, medium and long length Ck 3' spacers (SEQ ID NOS 42-44, respectively in order of appearance).

FIG. 9a depicts the 17/9 mRNA-scFv constructs with short and long spacer lengths.

FIG. 9b depicts results showing that shorter spacer length improved 17/9 mRNA-scFv molecule binding to target antigen and yield of mRNA-scFv antibody molecules.

FIG. 19 depicts general depiction of chimeras between D2E7 and 2SD4.

DETAILED DESCRIPTION OF THE INVENTION

Sequence Identification Numbers

Figure 1:
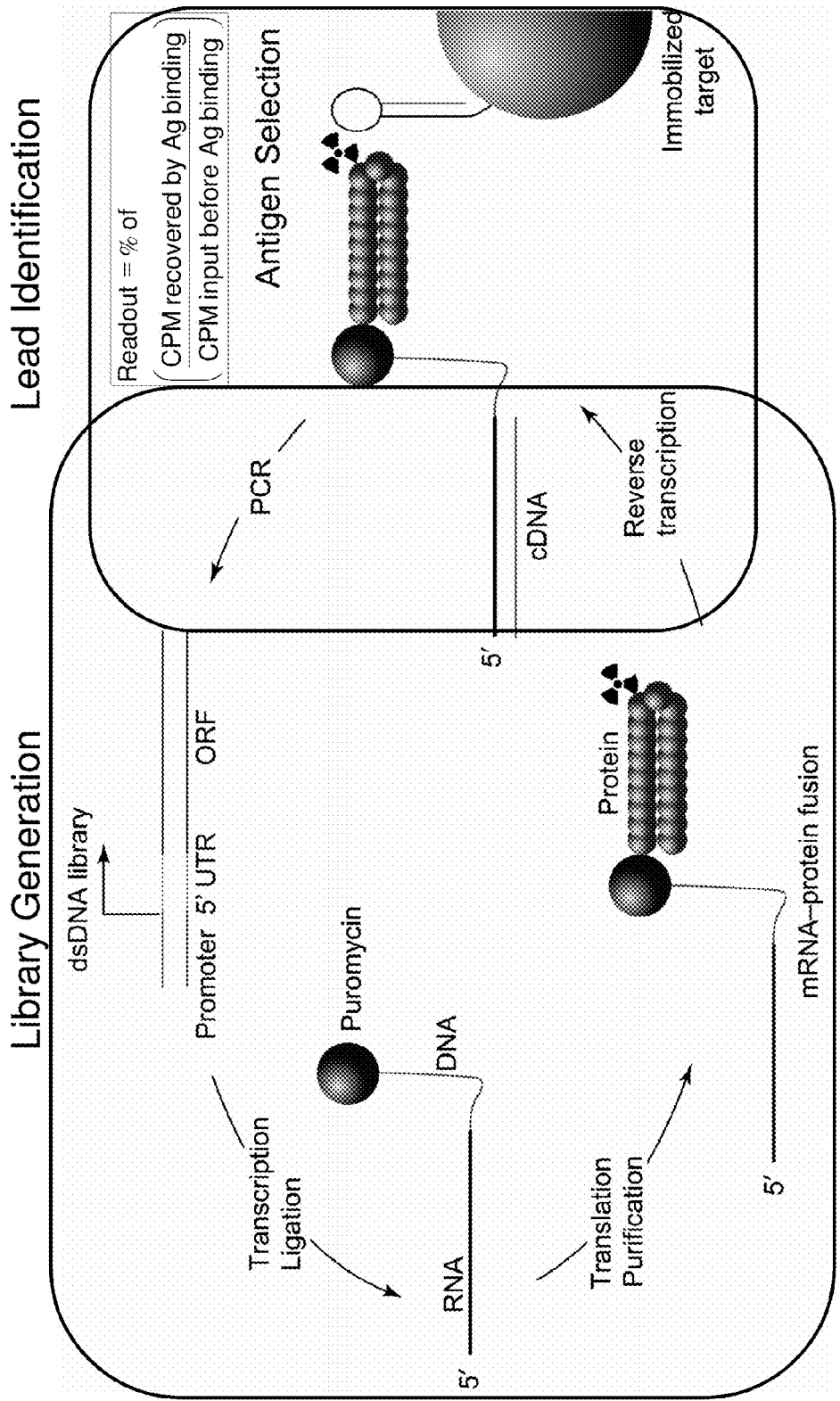
FIG. 1 depicts a general scheme for the mRNA-scFv display technology in some embodiments of the invention.

Nucleotide and amino acid sequences referred to in the specification have been given the following sequence identification numbers:

SEQ ID NO:1—Amino acid sequence of MAK195 scFv protein sequence.

SEQ ID NO:2—Amino acid sequence of Y61 scFv short protein sequence.

SEQ ID NO:3—Amino acid sequence of Y61 scFv long protein sequence.

SEQ ID NO:4—Amino acid sequence of Y61 scFv Gene3 protein sequence.

SEQ ID NO:5—Amino acid sequence of D2E7 scFv short protein sequence.

SEQ ID NO:6—Amino acid sequence of D2E7 scFv medium protein sequence.

SEQ ID NO:7—Amino acid sequence of D2E7 scFv long protein sequence.

SEQ ID NO:8—Amino acid sequence of 17/9 scFv short protein sequence.

SEQ ID NO:9—Amino acid sequence of 17/9 scFv long protein sequence.

SEQ ID NO:10—Nucleic acid sequence of MAK195 scFv nucleotide sequence.

SEQ ID NO:11—Nucleic acid sequence of Y61 scFv short nucleotide sequence.

SEQ ID NO:12—Nucleic acid sequence of Y61 scFv long nucleotide sequence.

SEQ ID NO:13—Nucleic acid sequence of Y61 scFv Gene3PA nucleotide sequence.

SEQ ID NO:14—Nucleic acid sequence of Y61 scFv Gene3 nucleotide sequence.

SEQ ID NO:15—Nucleic acid sequence of D2E7 scFv short nucleotide sequence.

SEQ ID NO:16—Nucleic acid sequence of D2E7 scFv medium nucleotide sequence.

SEQ ID NO:17—Nucleic acid sequence of D2E7 scFv long nucleotide sequence.

SEQ ID NO:18—Nucleic acid sequence of 17/9 scFv short nucleotide sequence.

SEQ ID NO:19—Nucleic acid sequence of 17/9 scFv long nucleotide sequence.

In order that the present invention may be more readily understood, certain terms are first defined.

Definitions

The term "antibody" includes monoclonal antibodies (including full length monoclonal antibodies), polyclonal antibodies, multispecific antibodies (e.g., bispecific antibodies), chimeric antibodies, CDR-grafted antibodies, humanized antibodies, human antibodies, murine antibodies and fragments thereof, for example, an antibody light chain (VL), an antibody heavy chain (VH), a single chain antibody (scFv), a F(ab')2 fragment, a Fab fragment, an Fd fragment, an Fv fragment, and a single domain antibody fragment (dAb).

The term "antibody library" refers to a plurality of DNA or RNA molecules containing an open reading frame (ORF) which encodes an antibody or fragment thereof. It also includes a plurality of antibody proteins and nucleic acid/antibody fusion molecules expressed from said DNA or RNA molecules.

The term "heavy chain variable domain" refers to the nucleic acid encoding an antibody heavy chain variable region and to the protein product of said nucleic acid.

The term "light chain variable domain" refers to the nucleic acid encoding an antibody light chain variable region and to the protein product of said nucleic acid.

The term "epitope tag" refers to a short amino acid sequence specifically recognized by an antibody that is attached chemically or genetically to a molecule to allow for its detection by said antibody, for example, FLAG tag, HA tag, Myc tag or T7 tag, The term "non-antibody sequences" refers to any nucleic acid or amino acid sequences that appear in the antibody libraries of the invention, which are not part of the original antibody sequence. Such sequences include, for example, epitope tags.

The term "control sequences" refers to DNA sequences or genetic elements necessary for the expression of an operably linked coding sequence in a particular host organism or in vitro expression system. Such sequences are well known in the art. The control sequences that are suitable for prokaryotes, for example, include a promoter, optionally an operator sequence, and a ribosome binding site. Eukaryotic cells are known to utilize promoters, polyadenylation signals, and enhancers. For example, nucleic acid is "operably linked" when it is placed into a functional relationship with another nucleic acid sequence. For example, a promoter or enhancer is operably linked to a coding sequence if it affects the transcription of the sequence, or a ribosome binding site is operably linked to a coding sequence if it is positioned so as to facilitate translation. Generally, "operably linked" means that the DNA sequences being linked are contiguous. However, enhancers do not have to be contiguous.

The term "specific binding" or "specifically binds to" refers to the ability of a binding molecule to bind to a target with an affinity of at least $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or less, and/or bind to a target with an affinity that is at least two-fold greater than its affinity for a nonspecific antigen.

The term "target" refers to an antigen or epitope recognized by an antibody. Targets include any peptide, proteins, saccharides, nucleic acids, or other molecule, including small molecules for which a specific antibody can be generated. In one embodiment, antibodies are against a human protein, for example, TNFα, IL-12, IL18, IL-1α or IL-1β.

A "conservative amino acid substitution" is one in which an amino acid residue is replaced with an amino acid residue having a similar side chain. Families of amino acid residues having similar side chains have been defined in the art.

The term "RNA display" or "mRNA display" refers to an in vitro technique wherein expressed proteins or peptides are linked covalently or by tight non-covalent interaction to their encoding mRNA to form "RNA/protein fusion" molecules. The protein or peptide component of an RNA/protein fusion can be selected for binding to a desired target and the identity of the protein or peptide determined by sequencing of the attached encoding mRNA component. Such methods are well known in the art and are described, for example, in U.S. Pat. Nos. 7,195,880; 6,951,725; 7,078,197; 7,022,479, 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315; each of which are herein incorporated by reference in their entirety.

The term "single chain antibody" or "scFv" refers to an antigen binding portion of a light chain variable region and an antigen binding portion of a heavy chain variable region, joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. U.S.A* 85:5879-5883).

The term "functional moiety" refers to any biological or chemical entity that imparts additional functionality to a molecule to which it is attached.

The term "selecting" refers to substantially partitioning a molecule from other molecules in a population. As used herein, a "selecting" step provides at least a 2-fold, preferably, a 30-fold, more preferably, a 100-fold, and, most preferably, a 1000-fold enrichment of a desired molecule relative to undesired molecules in a population following the selection step. As indicated herein, a selection step may be repeated any number of times, and different types of selection steps may be combined in a given approach.

The term "pause sequence" refers to a nucleic acid sequence that causes a ribosome to slow or stop its rate of translation.

The term "solid support" refers to, without limitation, any column (or column material), bead, test tube, microtiter dish, solid particle (for example, agarose or sepharose), microchip (for example, silicon, silicon-glass, or gold chip), or membrane (for example, the membrane of a liposome or vesicle) to which an affinity complex may be bound, either directly or indirectly (for example, through other binding partner intermediates such as other antibodies or Protein A), or in which an affinity complex may be embedded (for example, through a receptor or channel).

The term "linker region" refers to a region of nucleic acid connecting the nucleic acid sequences encoding antibody VH and VL domains in a scFv antibody gene. A linker region is in-frame with the nucleic acid sequences encoding antibody VH and VL such that a continuous open reading frame containing the VH, VL and linker regions is formed. The term also refers to the region connecting the VH and VL in an scFv protein.

The term "peptide acceptor" refers to any molecule capable of being added to the C-terminus of a growing protein chain by the catalytic activity of the ribosomal peptidyl transferase function. Typically, such molecules contain (i) a nucleotide or nucleotide-like moiety (for example, puromycin and analogues thereof), (ii) an amino acid or amino acid-like moiety (for example, any of the 20 D- or L-amino acids or any amino acid analog thereof (for example, O-methyl tyrosine or any of the analogs described by Ellman et al., Meth. Enzymol. 202:301, 1991), and (iii) a linkage between the two (for example, an ester, amide, or ketone linkage at the 3' position or, less preferably, the 2' position); preferably, this linkage does not significantly perturb the structure of the ring from the natural ribonucleotide conformation. In addition, this term encompasses, without limitation, a peptide acceptor molecule that is covalently bonded (either directly or indirectly through intervening nucleic acid sequence) to the protein coding sequence, as well as one that is joined to the protein coding sequence by some non-covalent means, for example, through hybridization using a second nucleic acid sequence that binds at or near the 3' end of the protein coding sequence and that itself is bound to a peptide acceptor molecule.

Overview

The present invention features improved methods of in vitro RNA display that allow reliable expression and selection of scFv antibody molecules from expression libraries.

RNA display methods generally involve expression of a library of proteins or peptides, wherein the expressed proteins or peptides are linked covalently or by tight non-covalent interaction to their encoding mRNA to form RNA/protein fusion molecules. The protein or peptide component of an RNA/protein fusion can be selected for binding to a desired target and the identity of the protein or peptide determined by sequencing of the attached encoding mRNA component. Current methods of RNA display are not optimal for scFv antibody expression since several of the steps are performed under reducing conditions which prevents formation of scFv intra-chain disulphide bond and thus correct folding of the scFv antibody molecules. Current methods additionally make use of either VH or VL antibody fragments in the selection process.

The present invention solves this technical problem by performing the in vitro RNA display assay under mildly reducing conditions that favor an scFv intra-chain disulphide bond and thus correct folding of the scFv antibody molecules. Using the scFv format rather than single variable domains (e.g., a single variable heavy (VH) domain) also eliminates the need to identify a compatible variable light (VL) domain necessary for the conversion of the selected VH domain into a full IgG antibody. Accordingly, although particularly suited to expression and selection of scFv antibody molecules, the methods of the invention are also expedient for in vitro RNA display of all classes of protein.

The methods of the invention also provide a shorter and simpler protocol for performing RNA display. This is achieved, in part, by avoiding the time consuming step of reverse transcribing the mRNA in an RNA-protein fusion into cDNA prior to selection with a target.

Improved in Vitro Rna-Display Screening Method

In one aspect, the invention features improved in vitro RNA-display screening methods. The general method is as follows:

1) Formation of RNA/Protein Fusions

One or more in vitro antibody DNA expression libraries are transcribed to generate mRNA. Any in vitro antibody expression library is suitable (e.g., VH, VL or scFv libraries), however, the methods of the invention are particularly well suited to scFv libraries. Any art recognized methods of transcription are suitable. After RNA transcription, the DNA library templates are removed. This may be accomplished using any art recognized methods, for example, by digestion with DNase I.

After DNA removal, a peptide acceptor is attached to the 3' end of the library mRNA. This may be accomplished using any art recognized methods. In one embodiment, a linker comprising 5' (Psoralen C6) 2'OMe(U AGC GGA UGC) XXX XXX CC (Puromycin) 3' (SEQ ID NO: 20), (where X is a Triethylene glycol or PEG-150 and CC is standard DNA backbone) is used. The linker is first allowed to bind to the 3' end of the library mRNA through complementary base pairing. The linker is then crosslinked to the mRNA by UV activation of the Psoralen C6 molecule.

After addition of the peptide acceptor, the library mRNA is then translated in an in vitro system. Any art recognized methods of in vitro translation are suitable, for example, rabbit reticulocyte lysate. However, to allow the proper intra-chain disulphide bond formation in scFv molecules a protein disulphide isomerase (PDI) is added to the in vitro translation reaction and/or the reaction is performed under mildly oxidizing conditions. In one embodiment, a mild oxidizing agent (for example, oxidized glutathione/reduced glutathione, for example 100 mM oxidized glutathione/10 mM reduced glutathione) is added to in vitro translation reaction. In another embodiment, reducing agents (for example, dithiothreitol (DTT)) are omitted from the in vitro translation reaction.

One or more labeled amino acids, or derivatives thereof, may be added to the in vitro translation system such that the labeled amino acid becomes incorporated into the resultant antibody. Any art recognized labeled amino acid is contemplated, for example, a radiolabelled amino acid, for example, $^{35}$S-labelled methionine or cysteine.

During the in vitro translation reaction the mRNA molecules become covalently linked to their protein products via the peptide acceptor (e.g., puromycin) fused at the 3' end. These RNA/protein fusion molecules are purified away from the in vitro translation reaction mixture. Any art recognized methods of separation of RNA/protein fusion molecules from a reaction mixture are contemplated. In one embodiment, the RNA/protein fusion proteins are separated by chromatography using a polydeoxythimidine (polydT) resin. In another embodiment, the RNA-antibody fusion proteins are separated by binding to an antibody specific for an epitope present in the antibody component of the RNA/protein fusion protein. The epitope may be an amino acid sequence tag, for example, FLAG or HA tags, incorporated into the amino acid sequence of the antibody component of the RNA-antibody fusion protein, for example, at the N-terminal, C-terminal or in the inter variable region linker.

The RNA/protein fusions of the invention, involve the use of naked RNA. In a preferred embodiment, all reagents that contact the RNA/protein fusions are treated with RNase inhibitor reagents, for example, RNaseOUT™, yeast tRNA, SUPERaseIn™, RNasin®, and other RNase inhibitors known in the art.

2) Screening for Antibodies to a Desired Target

The library of RNA/protein fusions is screened for in vitro binding to a desired target. In general the target molecules are bound to a solid support, for example, agarose beads. In one embodiment, the target molecule is directly linked to a solid substrate. In another embodiment, the target molecule is first modified, for example, biotinylated, then the modified target molecule is bound via the modification to a solid substrate, for example, streptavidin-M280, neutravidin-M280, SA-M270, NA-M270, SA-MyOne, NA-MyOne, SA-agarose, and NA-agarose. In other embodiments, the solid support further includes magnetic beads, for example Dynabeads. Such magnetic beads allow separation of the solid support, and any bound RNA/antibody fusion, from an assay mixture using a magnet.

After binding of RNA/protein fusions, the solid support is washed one or more times to remove unbound RNA/protein fusions and the RNA is then amplified. In one embodiment, mRNA that is physically associated with an antibody or plurality of antibodies is amplified to produce more mRNA. Any art recognized method of RNA replication is contemplated, for example, using an RNA replicase enzyme. In another embodiment, mRNA that is physically associated with an antibody or plurality of antibodies may be transcribed into cDNA before being amplified by PCR. The PCR amplified pool can be subject to one or more rounds of screening to enrich for the highest affinity antibodies.

Additionally or alternatively, the RNA/protein fusions may be eluted from the solid support prior to amplification of the nucleic acid component. Any art recognized method of elution is contemplated. In one embodiment, the RNA/protein fusions are eluted using alkaline conditions, for example, using a pH of about 8.0 to 10.0. In another embodiment, the RNA/protein fusions are eluted using acid conditions, for example, using a pH of about 3.0 to 6.0. In one embodiment, the RNA/protein fusions are not eluted prior to amplification of the nucleic acid component, but instead the RNA/protein fusions are added directly to the amplification reaction mixture.

Additionally or alternatively the PCR amplified pool of nucleic acids may be sequenced using single molecule sequencing methods to determine the nucleic sequences of every selected RNA/protein molecule. In one embodiment, PCR amplification may be accomplished using a high fidelity, proof-reading polymerase, for example, the KOD1 thermostable DNA polymerase from *Thermococcus kodakaraensis* or Platinum Taq DNA Polymerase High Fidelity (Invitrogen).

Additionally or alternatively, the nucleic acid sequences may be amplified under conditions that result in the introduction of mutations into amplified DNA, thereby introducing further diversity into the selected nucleic acid sequences. This mutated pool of DNA molecules may be subjected to further rounds of screening.

Library Construction

Libraries of the invention may be generated from any antibody fragment capable of binding to a target. In one embodiment, libraries of antibody variable domains are generated. These may be VH and/or VL domains. In another embodiment, scFv libraries are generated.

The libraries of the invention may also include antibody nucleic acid sequences encoding regions outside of the variable regions, for example, a constant region or fragment thereof, or a hinge region.

Nucleic acid libraries of the invention may comprise RNA, DNA or hydrids containing both RNA and DNA elements.

Linkage of Nucleic Acid to Peptide Acceptors

The antibody nucleic acid libraries may be modified to contain a peptide acceptor moiety. This may facilitate the covalent attachment of individual member of nucleic acid expression libraries to their cognate protein products. Any art recognized means of attachment of a peptide acceptor to a nucleic acid are contemplated, including the means described, for example, in U.S. Pat. No. 5,643,768, U.S. Pat. No. 5,658,754, U.S. Pat. No. 7,195,880, and U.S. Pat. No. 6,951,725, the contents of which are incorporated herein by reference.

In one aspect the invention features novel methods and compositions for the attachment of a peptide acceptor to nucleic acid libraries. In one embodiment, a linking molecule may be synthesized that comprises a Psoralen C6 molecule and a peptide acceptor molecule, wherein the Psoralen C6 molecule and a peptide acceptor molecule are fused to a nucleic acid sequence, wherein the nucleic acid sequence is complementary to sequences at the 3' end of the nucleic acid library. Such linking molecules can bind, via complementary base pairing, to the 3' end of nucleic acid library clones. Psoralen C6 is sensitive to ultraviolet (UV) light and will cross link the linker to the nucleic acid library clones, thus covalently linking the peptide acceptor to the nucleic acid library clones. In another embodiment, the nucleic acid portion of the linker molecule may contain modified nucleotides, for example, 2 prime methoxy (2'OMe) ribonucleotides. In another embodiment, the linker molecule further comprises a Triethylene glycol or PEG-150 linker separating the nucleic acid region containing the Psoralen C6 molecule and a peptide acceptor molecule. In one embodiment the linker may comprise, from 5' to 3': Psoralen C6, 2'OMe) ribonucleotides comprising the sequence UAGCGGAUGC (SEQ ID NO: 20), six Triethylene glycol or PEG-150 moeities, two cytidine residues, and Puromycin. Such linkers may be custom-synthesized by, for example, TriLink BioTechnologies, Inc.

General Screening Methods

In one aspect, the invention features methods of screening the expression libraries of the invention to identify antibodies capable of binding to a desired target. Any in vitro or in vivo screening method that allows for selection of an antibody from an expression library, based upon antibody binding to a target molecule, is contemplated.

In one embodiment, the expression libraries of the invention may be screened using an art recognized in vitro cell-free phenotype-genotype linked display. Such methods are well known in the art and are described, for example, in U.S. Pat. Nos. 7,195,880; 6,951,725; 7,078,197; 7,022,479, 6,518,018; 7,125,669; 6,846,655; 6,281,344; 6,207,446; 6,214,553; 6,258,558; 6,261,804; 6,429,300; 6,489,116; 6,436,665; 6,537,749; 6,602,685; 6,623,926; 6,416,950; 6,660,473; 6,312,927; 5,922,545; and 6,348,315. These methods involve transcription of protein in vitro from a nucleic acid in such a way that the protein is physically associated or bound to the nucleic acid from which it originated. By selecting for an expressed protein with a target molecule, the nucleic acid that codes for the protein is also selected.

To improve the expression of scFv proteins, the above referenced in vitro screening assays may require addition or removal of certain reagents. In one embodiment, protein disulphide isomerase enzymes may be added to the in vitro expression system to improve the production of functional scFv molecules. In another embodiment, a mild oxidizing agent (for example, oxidized glutathione/reduced glutathione, for example 100 mM oxidized glutathione/10 mM reduced glutathione) may be added to in vitro translation reaction mixture of the scFv proteins to allow intra-chain disulphide bond formation in the VH and VL regions of the scFv molecule. In another embodiment, reducing agents (for example, dithiothreitol (DTT)) may be removed from the in vitro translation reaction mixture of the scFv.

In another embodiment, one or more labeled amino acids, or derivatives thereof, may be added to the in vitro translation system such that the labeled amino acid becomes incorporated into the resultant antibody. Any art recognized labeled amino acid is contemplated, for example, a radiolabelled amino acid, for example, $^{35}$S-labelled methionine or cysteine.

In one embodiment, the in vitro screening assays of the invention require that after in vitro selection of an antibody or plurality of antibodies the mRNA that is physically associated with the antibody or plurality of antibodies may be reverse transcribed to generate cDNA encoding said antibody or plurality of antibodies. Any suitable method for reverse transcription is contemplated, for example, enzyme mediated reverse transcription, for example, Moloney murine leukemia virus reverse transcriptase.

Screening methods employed in the invention may require amplification of the nucleic acid that encodes antibodies that bind specifically to a desired target. In one embodiment, mRNA that is physically associated with an antibody or plurality of antibodies may be amplified to produce more mRNA. Any art recognized method of RNA replication is contemplated, for example, using an RNA replicase enzyme. In another embodiment, mRNA that is physically associated with an antibody or plurality of antibodies may be first reverse transcribed into cDNA before being amplified by PCR. In one embodiment, PCR amplification may be accomplished using a high fidelity, proof-reading polymerase, for example, the KOD1 thermostable DNA polymerase from *Thermococcus kodakaraensis* or Platinum Taq DNA Polymerase High Fidelity (Invitrogen). In another embodiment, PCR amplification may be performed under conditions that introduce mutations into the amplified DNA, e.g., error-prone PCR.

In another embodiment, the expression libraries of the invention may be screened by display on the surface of a cell, virus or bacteriophage and subject to selection using immobilized target molecules. Suitable methods of screening are described in U.S. Pat. Nos. 7,063,943; 6,699,658; 6,423,538; 6,696,251; 6,300,065; 6,399,763; 6,114,147 and 5,866,344.

Screening methods employed in the invention may require introduction of diversity into the antibody library by introducing nucleic substitutions and/or deletions that may result in one or more amino acid substitutions and/or deletions in the expressed antibodies molecules. Any art recognized methods of mutagenesis are contemplated, for example, random mutagenesis, "walk through" mutagenesis, and "look through" mutagenesis. Such mutagenesis of an antibody can be achieved using, for example, error-prone PCR, "mutator" strains of yeast or bacteria, or incorporation of random or defined nucleic acid changes during ab inito synthesis of all or part of an antibody. In one embodiment, a library of antibody molecules may be created in which one or more amino acids are randomly mutated. In another embodiment, a library of antibody molecules may be created in which one or more amino acids are mutated to one or more predetermined amino acids.

Screening methods employed in the invention may also require that the stringency of the target-binding screening assay be increased to select for antibodies with improved affinity for the target. Any art recognized methods of increasing the stringency of an antibody-target interaction assay may be considered. In one embodiment, one or more of the assay conditions may be varied (for example, the salt concentration of the assay buffer) to reduce the affinity of the antibody molecules for the desired target. In another embodiment, the length of time permitted for the antibodies to bind to the desired target may be reduced. In another embodiment, a competitive binding step may be added to the antibody-target interaction assay. For example, the antibodies may first be allowed to bind to a desired immobilized target. A specific concentration of non-immobilized target may then be added which serves to compete for binding with the immobilized target such that antibodies with the lowest affinity for antigen are eluted from the immobilized target resulting in an enrichment for antibodies with improved antigen binding affinity. The stringency of the assay conditions may be further increased by increasing the concentration of non-immobilized target that is added to the assay.

Screening methods of the invention may also require multiple rounds of selection to enrich for one or more antibodies with improved target binding. In one embodiment, at each round of selection further amino acid mutations may be introduced into the antibodies using art recognized methods. In another embodiment, at each round of selection the stringency of binding to the desired target may be increased to select for antibodies with increased affinity for a desired target.

Screening methods of the invention may require purification of RNA-antibody fusion proteins from the components of an in vitro translation system. This may be accomplished using any art recognized method of separation. In one embodiment, the RNA-antibody fusion proteins may be separated by chromatography using a polydeoxythimidine (polydT) resin. In another embodiment, the RNA-antibody fusion proteins may be separated by chromatography using an antibody specific for an epitope present in the antibody component of the RNA-antibody fusion protein. The epitope may be an amino acid sequence tag, for example, FLAG, Myc, or HA tags, incorporated into the amino acid sequence of the antibody component of the RNA-antibody fusion protein, for example, at the N-terminal, C-terminal or in the inter variable region linker.

Selection of antibodies from the libraries of the invention may require the use of immobilized target molecules. In one embodiment, the target molecule is directly linked to a solid substrate for example, agarose beads. In another embodiment, the target molecule is first modified, for example, biotinylated, then the modified target molecule is bound via the modification to a solid support, for example, streptavidin-M280, neutravidin-M280, SA-M270, NA-M270, SA-MyOne, NA-MyOne, SA-agarose, and NA-agarose.

EXEMPLIFICATION OF THE INVENTION

Figure 2:
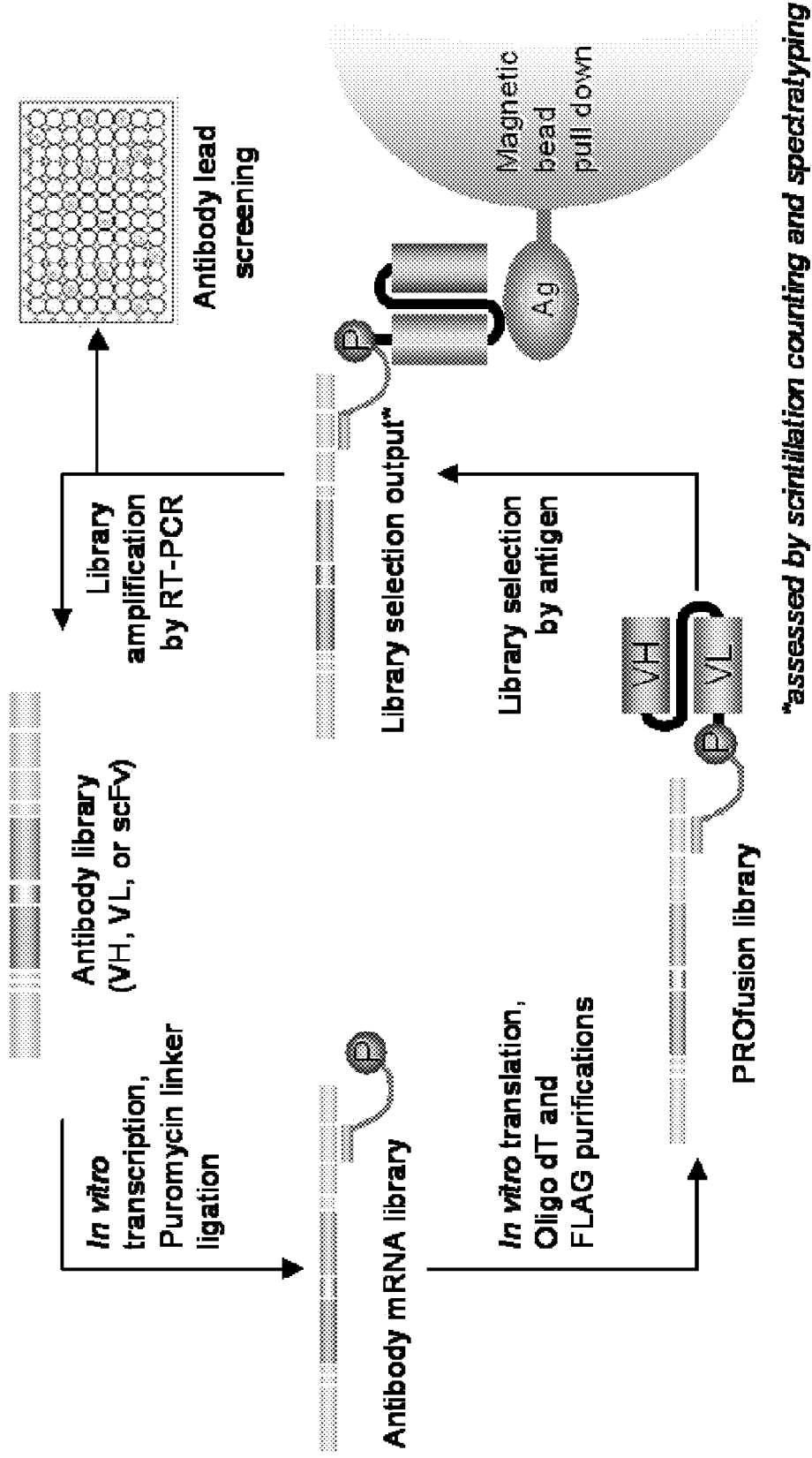
FIG. 2 depicts a general scheme for the mRNA-scFv display technology in other embodiments of the invention.

Throughout the examples, the following materials and methods were used unless otherwise stated.
Materials and Methods In general, the practice of the present invention employs, unless otherwise indicated, conventional techniques of chemistry, molecular biology, recombinant DNA technology, immunology (especially, e.g., immunoglobulin technology), and animal husbandry. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); Current Protocols in Molecular Biology, eds. Ausubel et al., John Wiley & Sons (1992).
mRNA Display Protocol for scFv mRNA display may be conducted according to the method shown in FIG. 2. Particular embodiments of this method are described in greater detail below. These embodiments are intended to illustrate the methods of the invention, and should not be construed as limiting.
1. Design of Antibody Library Templates Library DNA constructs may be designed according to methods of antibody library generation known in the art. In one embodiment, the library constructs may encode antibody fragments, i.e., antibody light chain fragments (VL) or antibody heavy chain fragments (VH). In an exemplary embodiment, the library constructs may encode single chain variable fragments (scFv).
2. Preparation of Target Antigen Generally the mRNA display antibody library may be selected against biotinylated antigen. While the best antigen for each target should be determined on a case-by-case basis, the following considerations may be used as a general guideline. A target antigen is typically well characterized, and is the relevant or dominant genetic isotype, as determined by polymorphism (SNP and haplotype) and/or pharmacogenetic analysis. A target antigen additionally may have reasonable bioactivity (comparable to native antigen), good solubility and good chemical and physical properties, and may be prepared in sufficient quantities for library selections or screenings and downstream bioassays.

3. Preparation of Library DNA

Library DNA and its selection outputs may be amplified by PCR. PCR amplification may be performed using methods known in the art. PCR reactions typically contain DNA template, reaction buffer, dNTP, primers used for amplification, DNA polymerase, and water. Multiple reaction tubes may be set up simultaneously from a master mix to increased amplified DNA yield. 25 cycles of PCR typically give sufficient amplification, but as many as 35 cycles may be used to gain more products.

4. Library DNA Purification

If products are the correct size (~850 bp for scFv, ~500 bp for VH or VL library) and contain minimal non-specific products, the products may be used directly in the transcription reaction. Alternatively, the products may be purified on a preparative agarose gel by cutting out the specific band of the correct size. DNA concentration may be measured on a spectrophotometer.

5. RNA Transcription

RNA transcription from library DNA may be performed using standard methods known in the art. A large reaction volume may be used to transcribe sufficient DNA templates to sample the entire library diversity. In an exemplary embodiment, $1 \times 10^{13}$ copies of library templates may be used in the RNA transcription reaction. An RNA transcription typically contains 5-10 µg of PCR product, reaction buffer, ATP, CTP, GTP, UTP, and T7 RNA polymerase. The RNA transcription reaction may be run at 37° C. for between 2 hours to overnight. Shorter times may be used following initial rounds of selection, however, overnight incubations may maximize the RNA yield of the reaction. Following RNA transcription, DNA templates may be removed from the reaction mixture by DNase I digestion.

6. RNA Purification by NAP Column Chromatography

Following transcription, RNA may be fractionated using a NAP-10 column. Up to about 1 mL of transcription reaction may be loaded onto a NAP-10 column for RNA purification. The column may be equilibrated using DEPC-treated $dH_2O$ prior to fractionation. RNA may be eluted from the column using about 1.5× the reaction volume DEPC-treated $dH_2O$ (e.g. 750 µL per 500 µL transcription reaction). The total elution volume may be less than about 150% of the transcription reaction volume. RNA may be additionally or alternatively fractionated using a NAP-25 column 7. RNA Quality Control and Quantitation The size and yield of RNA samples may be analyzed using gel electrophoresis, or alternatively by measuring the OD at 260 nm ($OD_{260}$) of RNA concentration in collected fractions. For example, molar concentration of scFv RNA may be calculated as follows:

$$[RNA](\mu M) = [RNA](mg/mL) \times 10^6 / (850 \times 330)$$
$$= OD_{260} \times \text{dilution factor} \times 40(\mu g/mL) \times 1000/(850 \times 330).$$

$$RNA \text{ yield (nmol)} = [RNA](\mu M) \times \text{Volume}(\mu L)/1000$$

The RNA yield typically reaches a maximum at about 20 nmol/mL per 500 µL transcription reaction.

8. RNA Ligation to Linker

A DNA linker that contains a peptide acceptor molecule at its 3' end may be covalently ligated to the 3' ends of each RNA molecule by UV crosslinking. The peptide acceptor, which may enter the ribosomal A site and covalently couple to the carboxyl terminus of the nascent polypeptide chain, may ultimately enable the covalent association of the mRNA (genotype) to the protein encoded by this mRNA (phenotype). An exemplary PEG6/10 linker may be used which has the following formula:

```
                                        (SEQ ID NO: 20)
5' (Psoralen C6) 2'OMe(U AGC GGA UGC) XXX XXX CC (Puromycin) 3'
```

The Psoralen C6 5' modification is light sensitive and functions to create a covalent bond between the linker and the mRNA by UV crosslinking. A 2'OMe(U AGC GGA UGC) (SEQ ID NO: 20) backbone region anneals to the linker annealing site 3' to the FLAG sequence on mRNA (see FIG. 1). In the sequence above, X denotes "Spacer 9", alternatively known as Triethylene glycol or PEG-150. This spacer has been optimized to provide flexibility for puromycin insertion into the eukaryotic ribosome A site. CC comprises a standard DNA backbone. A puromycin 3' modification inserts into the ribosome A site to create a stable link between the linker and the nascent peptide. The extinction coefficient for the linker described herein may be about 147.7 $OD_{260}$/µmole. Since this linker is light sensitive, solutions containing this linker should be protected from light.

For initial rounds of library selections, a large-scale ligation reaction (about 5 nmol or about $3.1 \times 10^{15}$ transcribed RNA molecules) may be recommended to sample the entire diversity of a naïve antibody library with an estimated diversity of about $10^{12}$-$10^{13}$. This RNA quantity may ensure enough templates are incorporated into translation reactions to produce ~10 pmol functional mRNA display molecules. In later rounds, RNA input may be reduced to about 0.5 nmol per selection. In an exemplary embodiment, an RNA ligation reaction may contain the following components: RNA, water, chemical ligation buffer, and the PEG6/puromycin linker (1 mM). In an exemplary embodiment, the total reaction volume is about 100 µL. In a preferred embodiment, the linker/RNA molar ratio may be greater than about 1.5. In one embodiment, the final linker concentration in the reaction is about 15 µM, and the RNA concentration in the reaction may range from about 3-10 µM (=0.3-1 nmol RNA input). As a reference, an 850 nt scFv RNA at 1 mg/mL=3.56 µM, and the attainable maximal ligation concentration would be about 3.16 µM (about 0.32 nmol).

The annealing reaction (which anneals the linker to the transcribed RNA) may be performed in a thermal cycler. In a preferred embodiment, the annealing reaction may be conducted by incubating samples at about 85° C. for about 30 seconds, then at about 4° C., using a ramp rate of about 0.3° C. per second. Reactions may then be held at about 4° C.

Ligation of the annealed linker/RNA may be accomplished by UV crosslinking. This may be conducted using any method known to one of skill in the art. In one embodiment, reaction tubes may be placed on top of a frozen freezer pack and placed directly under a handheld long wavelength (about 365 nm) UV lamp and crosslinked for about 15 minutes in the dark. Typical ligation efficiency is about 50-90%. Generally purification is not required. The ligation products may be stored at −80° C.

9. Translation Reaction

In an exemplary embodiment, about ~0.1% of input RNA may be made into mRNA display molecules after all reactions and purifications. In vitro translation is conducted using methods and reagents known to one of skill in the art. In one embodiment, the translation reaction using the scFv library uses about 5 nmol of RNA template with about 10 mL of reticulocyte lysate in a reaction volume of about 15 mL.

In preparation for the translation reaction, solutions of oxidized glutathione/reduced glutathione may be prepared at a final concentration of about 100 mM oxidized glutathione/10 mM reduced glutathione. PDI is prepared by dissolving PDI powder into dH$_2$O to reach a concentration of about 1 Unit/µL. The PDI solution may be stored at −20° C.

An exemplary translation reaction may be set up as follows:

| | | | |
|---|---|---|---|
| RNA (100-120 pmol/300 µL or 500-600 pmol/1.5 ml) | X | X | µL |
| dH$_2$O | to 73.7 | to 370 | µL |
| Amino acid master mix (Met⁻) | 15 | 75 | µL |
| 100 mM oxidized glutahione/ 10 mM reduced glutatione | 3.3 | 16.5 | µL |
| PDI (1 U/µL) | 6 | 30 | µL |
| [$^{35}$S]Methionine | 2 | 10 | µL |
| Reticulocyte lysate | 200 | 1000 | µL |
| Total volume | 300 | 1500 | µL |

Translation reactions may be incubated in 30° C. water bath for 1-2 hours, and the to RNA/protein fusion formation should be performed without delay. A significant decrease in RNA/protein fusion yield may be observed when the translation volume exceeds 3 mL; consequently, a master mix of the translation reaction may be prepared if the reaction volume is larger than 3 mL, and then divided into smaller aliquots.

10. RNA/Protein Fusion Formation

After the translation reaction, about 100 µL 2M KCl and about 20 µL 1M MgCl$_2$ may be added for every 300-µL of translation reaction mixture, and incubated for about 1 hour at room temperature, or at −20° C. overnight. Alternatively, about 500 µL 2M KCl and about 100 µL 1M MgCl$_2$ may be added for every 1.5 ml of translation reaction mixture, and incubated for about 1 hour at room temperature, or at −20° C. overnight. This stabilizes the paused ribosomes at the end of mRNA templates and allows puromycin at the end of the DNA linker to enter the A sites of paused ribosomes, which permanently links the translated scFv proteins to their mRNA templates. The room temperature incubation may be shortened if the reaction is stored at −20° C. overnight. The reaction may be terminated by adding about 50 µL or about 250 µL 0.5 M EDTA per 300 µL or 1.5 ml translation reaction, respectively, to disrupt the ribosomes. Reactions may be stored at −20° C. A 5-10 µL aliquot may be removed for scintillation counting later.

11. RNA/Protein Fusion Purification by Oligo-dT Cellulose

This step is included to purify mRNA display molecules and remaining RNA templates from the translation/fusion reaction. For oligo-dT binding, the amount of pre-washed oligo-dT cellulose needed to capture all RNA templates should be estimated. A sufficient volume of oligo-dT binding buffer may be added to the fusion reaction to reach about a 1× final concentration. Pre-washed oligo-dT cellulose may then be added, and the reactions are rotated for 1 hour at 4° C. Reactions may optionally be spun down at about 1500 rpm for 5 min at 4° C., and the supernatant is discarded. Oligo-dT cellulose beads may be transferred and washed about 6 times with 1× Oligo-dT binding buffer using spin columns, and buffer is typically removed by spinning columns at about 1000 rpm for 10 seconds. The flow-through may be discarded, but the last wash may be saved for scintillation counting. To reduce salt concentration and facilitate elution, 1/10 of the initial slurry volume of dH$_2$O may be added to the dry oligo-dT beads, which may be centrifuged immediately for 10 seconds and the flow through may be discarded. mRNA display molecules (and free RNA templates) may be eluted by adding dH$_2$O to beads and incubating for 5 minutes at room temperature. Eluate is collected by spinning at about 4000 rpm (or higher) for 20 seconds. The elution is typically repeated once, and the eluates are combined. 5 µL of eluate may be removed for scintillation counting. Optionally, the efficiency of oligo-dT purification may also be assessed by OD at 260 nm (OD$_{260}$) on a NanoDrop spectrophotometer machine. All remaining RNA templates and mRNA display molecules are theoretically recovered by the oligo-dT beads. 5×FLAG binding buffer is added to the eluates to reach about a 1× final concentration. Samples may be stored at −80° C. if not proceeding to the next FLAG purification step.

Oligo-dT recovery may be calculated as follows. About 5 µL of input (from fusion reaction), about 100 µL from the last wash, and about 5 µL of output (eluate from oligo-dT purification). The last wash is used to assess extent of washing, and the other two counts are used to calculate RNA/protein fusion recovery from original RNA template input. RNA/protein fusion yield (pmol)=(CPM$_{output}$×Volume$_{output}$×5 µM×Volume$_{lysate}$)/[CPM$_{input}$×Volume$_{input}$×(# of methionine in product)]. This formula assumes a 5-µM methionine concentration in the reticulocyte lysate, and all volumes used in calculation expressed as µL. For earlier rounds of selection the yield of mRNA display molecules is typically 0.5-2%, but may increase to 10% in later rounds. For example, early rounds number of methionine in PROfusion library may be:

About 3 µM for VH-Vκ scFv,
About 2 to 3 µM for VH-VλscFv,
About 2 µM for VH,
About 2 µM for Vκ, and
About 1 µM for Vλ.

These numbers are averages and are based on germline sequences, and one of skill in the art will appreciate that they may change over selection rounds as the library is enriched toward specific sequences.

12. RNA/Protein Fusion Purification by Anti-FLAG M2 Agarose

This step is designed to purify mRNA display molecules from remaining RNA templates. It is not necessary to proceed to this step if the library will be selected by antigen off-rate competition or by antigen-expressing cells. The amount of pre-washed anti-FLAG M2 agarose beads needed to capture all mRNA display molecules may be estimated. In one embodiment, the binding capacity of the beads may be about 6 nmol fusion protein per mL of 50% slurry. To have sufficient bead volume for manipulation during binding and washing, it is recommended to use at least about 200 µL of pre-washed beads. The example given below is for an initial 300-µL translation reaction.

FLAG purification: a wide-bore pipette tip may be used to transfer 300 µL pre-washed anti-FLAG M2 agarose to the oligo-dT purified output, which may then be rotated for 1 hour at 4° C. Incubation with anti-FLAG M2 agarose may continue overnight. Anti-FLAG M2 agarose may optionally be spun at about 1500 rpm in a centrifuge for about 1 minute at 4° C., and the supernatant may be discarded. Anti-FLAG beads may be washed about 5-6 times with about 500-700 μL 1×FLAG binding buffer, using spin columns (e.g. Invitrogen™ Microcentrifuge Spin Column) and centrifuged at about 1000 rpm for 10 seconds for each wash (note that the Invitrogen™ column may be spun at higher speeds, e.g. about 10,000 rpm). The flow-through may be discarded. The beads may additionally be washed 2 times with 700 μL Selection Buffer (see below) by centrifugation at about 1000 rpm for 10 seconds. The last wash may be saved for scintillation counting. mRNA display molecules may be eluted by adding about 400 μL 100 μg/mL FLAG peptide (in Selection Buffer) and incubating for 5 minutes at room temperature. Elute may be collected by spinning at about 3000 rpm (or higher if possible) for 20 seconds. The elution step may be repeated one more time by adding about 400 μL 100 μg/mL FLAG peptide. Both eluates may be combined, and about 5 μL may be removed for scintillation counting. This volume of FLAG peptide may be sufficient for elution from up to about 1 mL of 50% slurry and may be cut in half (200 μL) if less slurry is used and/or higher RNA/protein fusion concentration is desired. To prevent RNA degradation during storage and antigen selection, an appropriate amount of RNase inhibitor known in the art (i.e., 1-2 U/μL RNaseOUT and 0.02 μg/mL yeast tRNA) may be added to the purified mRNA display library. Store samples at −80° C. if not proceeding to the next antigen selection step.

To quantitate the FLAG recovery, about 5 μL elution output and about 100 μL from the last wash are counted on a beta counter. A recovery of 10-30% or higher may be expected, and may be calculated according to the following formula:

$$\text{PROfusion molecule recovery \%} = (\text{CPM}_{output} \times \text{Volume}_{output})/(\text{CPM}_{input} \times \text{Volume}_{input})$$

13. Library Selection by Biotinylated Antigens

Selection is designed to enrich for molecules that specifically bind to a target of interest when library binding to an antigen reaches equilibrium. A negative selection (pre-clear) may be necessary to remove non-specific and matrix binders from a naïve scFv library, but may be omitted if using a library made from a single template, e.g., but not limited to, libraries made for affinity maturation doing affinity maturation based on a single scFv template. Depending on the target format, the selection protocol varies. The following is an exemplary selection protocol for use with biotinylated targets. This protocol may be modified to accommodate target antigens in other formats, and may be scaled up or down depending on the desired output.

A. Preparations Before Selection

Streptavidin (SA) magnetic beads may be used for capture, and are typically pre-blocked prior to use. SA beads may be transferred from the original bottle to 1.5 or 2 mL tubes, and washed twice with 2 mL of 1×FLAG binding buffer. Beads may be blocked with 2 mL of Selection buffer (2 hours to overnight) at 4° C. with rotation. It is important to prepare enough beads for both, the pre-clear and selection captures. Pre-blocked beads may be stored at 4° C. About 100 μL of beads are typically used for every 10 pmol of biotinylated antigen, but one of skill in the art will appreciate that capture bead volume should be calculated in view of the binding capacity of free biotin (e.g. 650-900 pmoles/mg beads, where the bead concentration is typically 10 mg/ml) relative to the reaction yield.

1.5 mL or 2 mL microfuge tubes may be pre-blocked with 1×FLAG binding buffer for about 1 hour to overnight. Pre-blocked tubes may be used for all pre-clear and selection steps. Typically four tubes are needed for each sample: 2 for pre-clearing, 1 for the beads, and 1 for selection.

Optimal results may be obtained by pre-clearing the library. FLAG purified mRNA display library may be added to beads (separated from buffer), using SA bead volume equal to half of the capture volume. Beads may be rotated at 30° C. for about 30 minutes. Pre-cleared mRNA display library may be separated from beads using a magnet, and the pre-clear may be repeated one more time. The second pre-clear SA beads may be washed and counted as described in above to determine if background is high. This may also serve as a 'No antigen' negative control.

B. Library Selection: Binding

For first rounds of selection, biotinylated target (100 nM) may be added to the whole pre-cleared library, and rotated at 30° C. for 1 hour. For later selection rounds when recovery of antigen-binding molecules is expected to exceed 1%, the pre-cleared library may be divided into 2 equal aliquots. Biotinylated antigen may be added to one aliquot, and the other may serve as the 'No antigen' negative control. Alternatively, the washed second pre-clear beads may also be considered as a 'No antigen' control, as noted above, although these beads will have one less 'pre-clear'. The antigen concentration in later rounds may be dropped when recovery of antigen-binding molecules exceeds 5%. In particular, antigen concentration should be reduced if the antigen appears to be 'sticky' and significant recovery was observed in early rounds. Antigen concentration may be reduced in later rounds when recovery of antigen-binding molecules becomes significantly higher than background (e.g. relative to a no antigen control). It is important to pay attention to the stoichiometry between library and antigen to ensure that there is at least a 5-fold molar excess of antigen over library PROfusion molecules, especially at lower antigen concentration C. Library Selection: Capture The selection buffer used for blocking the SA beads for library capture may be removed by centrifugation and magnetic separation. The antigen-bound library may be transferred to pre-blocked SA beads (separated from buffer), and then to the binding reaction, and rotated at 30° C. for 5 to 10 minutes. The amount of SA beads for capture should be calculated based on the capacity and the target concentration used in selection (see above). The amount of SA beads should be lowered when lowering the target concentration to avoid the SA bead binders, but typically not less than 50 μL of beads is used.

D. Library Selection: Washing

The SA beads may be collected using a magnet, and washed with about 1 mL of Selection buffer for 1 minute. This step may be repeated about 5 times (about 6 times total). The wash time may be increased in later rounds to incorporate off rate selection strategy to some targets. The beads may be washed one last time with about 1 mL of 1× buffer suitable for reverse transcription, collected with a magnet, and re-suspended in water (one fourth of the capture bead volume calculated above).

As another example, Dynabeads™ (Invitrogen) may be used, but one of skill in the art will appreciate that other beads may be equally suitable. The Dynabeads™ may be separated from the unbound library by centrifugation and magnetic separation. The supernatant may be removed with a 1 mL tip, using one new filtered tip for each library selection tube to eliminate cross-contamination. The Dynabeads™ may be washed with 1 mL of Selection buffer, and re-suspended by gentle pipetting or by inverting tubes multiple times. The tubes may be put back onto the magnetic holder for bead separation while the next library is processed. After all libraries are washed, supernatant may be removed by 1 mL tip using one new filtered tip for each library selection tube to eliminate cross-contamination. Repeat for five washes. Dynabeads™ may be washed two times with 1 mL of 1× First Strand buffer (SuperScript II, Invitrogen) as described above. At the last wash, removed 1/10 of the library to a separate tube for counting to determine library recovery if so desired. Dynabeads™ may be captured by magnetic separation and about 100 µl wash buffer may be saved for background count. Dynabeads™ may be re-suspended in water, using ¼ of the capture bead volume as calculated above).

E. Library Selection: Counting and Recovery Calculation

Starting from Round 3, count about 10-20% of the last wash and the beads. It is not advisable to count more than 100 µL of beads, as this may quench the counts. Library selection recovery may be calculated according to the following formula:

$$\text{Selection recovery \%} = 100 \times \text{CPM}_{Total\ Beads} / \text{CPM}_{Total\ Input}$$

14. Equilibrium Library Selection by Fc Fusion Proteins

In another embodiment, library selection may be performed for target antigens that have been fused to an antibody Fc domain (e.g. Fc fusion proteins). A negative selection (pre-clear) may be necessary to remove non-specific and matrix binders from naïve antibody library but may be omitted for affinity maturation. Selection specificity may be improved by fusing target antigens to both human IgG1 and mouse IgG2a. By having different Fc domains in the Fc fusion proteins during library selection, the risk of identifying library binders specific to the Fc region may be minimized. This will also enable the library binder to be pulled down by two different magnetic beads (protein G and anti-mouse IgG), thereby further reducing the chance of recovering anti-protein G or anti-anti-mouse IgG binders. The target Fc fusion protein may also be biotinylated, and selected either by the method described here or by the method described above in section 13. It should be noted that protein A magnetic beads may not be suitable for selecting against Fc fusion protein targets because of cross-reactivity to certain portions of the antibody VH domain (e.g. VH originated from human VH3 family germline sequences). Suitable magnetic beads for pulling down antigen binding scFv-PROfusion molecules include, but are not limited to, Dynabeads Protein G, Dynabeads Pan mouse IgG, and other available Dynabeads M-280 to human or to mouse IgGs. In general, protein G beads capacity is considered to be about 25 µg of human IgG1 (~167 pmol) per 100 µL of protein A/G magnetic beads.

A. Preparations Before Selection

Dynabeads Protein G or Dynabeads Pan mouse IgG (if target antigen is a mouse Fc fusion protein) may be used for capture, and are typically pre-blocked prior to use. The amount of Dynabeads needed for library pre-clear and selection may be calculated. Dynabeads may be transferred from the original bottle to 1.5 or 2 mL microfuge tubes and remove buffer. Beads may be blocked with 1 mL selection buffer (2 hours to overnight) at 4° C., or 1 hour at room temperature. It is important to prepare enough beads for both the pre-clear and selection captures.

1.5 mL or 2 mL microfuge tubes may be pre-blocked with selection buffer for 1 hour to overnight, and pre-blocked tubes should be used for all pre-clear and library selection steps.

FLAG purified scFv PROfusion library may be added to pre-blocked beads (separated from buffer), Dynabead (protein G or pan mouse IgG) volume equal to half of the capture volume (as calculated above) may be used and the reaction rotated at 30° C. for 30 minutes. The pre-cleared fusion library may be separated from beads with magnet, and the pre-clear repeated one more time. The second pre-cleared Dynabeads may be washed and counted as described above to determine if background is high. This may also serve as a 'No antigen' negative control.

B. Library Selection: Binding

For the first rounds of selection, biotinylated target (100 nM) may be added to the whole pre-cleared library, and rotated at 30° C. for 1 hour. For later selection rounds when recovery of antigen-binding molecules is expected to exceed 1%, the pre-cleared library may be divided into two aliquots (from 50/50 to 80/20 depending on the library counts). Biotinylated antigen may be added to one aliquot (50 to 80% of whole), while the other aliquots may serve as the 'no antigen' negative control. Alternatively, the washed second pre-clear beads may also be considered as a 'No antigen' control, as noted above, except that it will have one less 'pre-clear'. The antigen concentration may be reduced if the antigen appears to be 'sticky' and significant recovery was observed in early rounds. Additionally, antigen concentration may be reduced in later rounds when recovery of antigen-binding molecules becomes significantly higher than background (no antigen control). It is important to pay attention to the stoichiometry between library and antigen to ensure that there is at least a 5-fold molar excess of antigen over library PROfusion molecules, especially at lower antigen concentration.

C. Library Selection: Capture

The selection buffer used for blocking the Dynabeads for library capture may be removed by centrifugation and magnetic separation. The antigen-bound library may be transferred to pre-blocked Dynabeads (separated from buffer), and then to binding reaction, and rotated at 30° C. for 20 minutes. The amount of Dynabeads used for capture may be calculated as described above based on the bead capacity, and the target antigen concentration used in the selection. To avoid pulling down bead binders, the amount of Dynabeads should be reduced (but not to less than 500 µg or 50 µl) when the target antigen concentration is reduced.

D. Library Selection: Washing

The Dynabeads™ may be separated from the unbound library by centrifugation and magnetic separation. The supernatant may be removed with a 1 mL tip, and one new filtered tip may be used for each library selection tube to eliminate cross-contamination. New pipette tips may be used to wash the Dynabeads™ with about 1 mL of Selection buffer, and the Dynabeads™ may be re-suspended by gentle pipetting or by inverting tubes multiple times. The tubes may be placed back onto magnetic holder for bead separation while the next library is processed. After all libraries are washed, supernatant may be removed with a 1 mL tip (use one new filtered tip for each library selection tube to eliminate cross-contamination). This step may be repeated for five washes. Dynabeads™ may be washed two times with 1 mL of 1× First Strand buffer (SuperScript II, Invitrogen) as described above. At the last wash, 1/10 of library may be removed to a separate tube for counting to determine library recovery if so desired. Dynabeads™ may be captured by magnetic separation and about 100 µl of wash buffer may be saved for background count. Dynabeads™ may be re-suspended in water, using ¼ of the capture bead volume as calculated above).

E. Library Selection: Counting

May be performed as described in section 13 (E) above.

15. Off-Rate Library Selection by Antigen Competition

The major difference between off-rate selections and equilibrium selections is that the library binds to the selecting antigen first before FLAG purification. After FLAG purification the library may be incubated with an excess amount of competitor antigens or antibodies (e.g. when competitor antigens are not available) such that any pre-bound antigen that becomes unbound from the PROfusion molecules during off-rate competition is replaced by the competitors. The competitor is distinct from the pre-bound antigen in that competitor-bound PROfusion molecules may not be recovered in the subsequent recovery step. They may be un-modified antigens or antigens in a different format. Although antibodies may also be competitors, typically they are not as efficient competitors as antigen, and their efficiency decreases as the library's affinity to antigen increases. It is advantageous for the off-rate of the library to be determined just prior to selection in order to identify the proper duration of competition. This duration may range from several hours to several weeks.

A: Preload Library with Biotinylated Antigen or Antigen-Fc Fusion Protein

PROfusion molecules may be translated and purified by oligo-dT as described above. The oligo-dT purified library may be equilibrated by adding 5×FLAG binding buffer to a final concentration of 1× (simply add 25% of the library volume). Antigens (biotinylated or Fc-fusion) may be added to a sufficiently high concentration and rotated at 30° C. for 30 minutes to saturate antigen-antibody binding. PROfusion molecules may be purified by anti-FLAG M2 agarose as described above. It is important to note that a FLAG-purified PROfusion library should be kept on ice, but not frozen. It is important to pre-block sufficient amounts of capture beads as described above.

B: Determine Competitor Concentration and Library Baseline Recovery

The amount of recovered library from the above step may be calculated to determine its molar concentration. This represents the maximal amount of library-bound antigen, and may be used to calculate the amounts needed (500× to 1000×) for off-rate competition.

10% pre-blocked beads may be added to a 10% aliquot from antigen-bound PROfusion library and rotated for about 20 min at about 4° C. The beads may be washed 5 times with 1 mL of Selection Buffer as described above. The beads may be counted to determine the percentage of PROfusion library bound by antigen before off-rate selection as follows:

Recovery %=100×($CPM_{Beads}$/$CPM_{Input}$)×10

C: Library Selection: Competition 1000-fold molar excess of competitor (e.g. unmodified antigen or antibody) may be added to FLAG-purified PROfusion library and rotated at about 30° C. for a predetermined duration that will apply sufficient selection pressure to select for clones with better off-rates. Chill library on ice for about 1 to 2 minutes to slow down off-rate before bead capture.

D: Library Selection: Capture

The selection buffer used for blocking the Dynabeads for library capture may be removed by centrifugation and magnetic separation. The antigen-bound library may be transferred to pre-blocked Dynabeads (separated from buffer), and rotated at 4° C. for about 20 minutes.

E: Library Selection: Washing

The Dynabeads may be collected by centrifugation and magnetic separation from library. The supernatant may be removed with a 1 mL tip (use one new filtered tip for each library selection tube to eliminate cross-contamination, as described above).

Beads may be washed two times with about 1 mL of 1× First Strand buffer (SuperScript II, Invitrogen) as described above. At the last wash, 10 to 20% of library may be removed to a separate tube for counting to determine library recovery if so desired. Dynabeads may be captured by magnetic separation and 100 µl wash buffer may be saved for background count. Beads may be re-suspended in water (¼ of the capture bead volume as calculated above).

F: Library Selection: Counting and Recovery Calculation 10-20% of the last wash and the beads may be counted. It is advisable to avoid using more than 100 µL beads, as it may quench the counts. Library selection recovery may be calculated using the following formula:

Selection recovery %=100×$CPM_{Total\ Beads}$/$CPM_{Total\ Input}$

16. Reverse Transcription of Library Selection Outputs

Reverse transcription may be done with SuperScript II Reverse Transcriptase (Invitrogen™). The volume of each reaction may be scaled up according to the bead volume after selection. Outputs may be analyzed by reverse transcription (RT) with appropriate primer pairs. For example, 'Ck Reverse' or 'Ck5-FLAGA20 Rev' primers may be used for kappa libraries, 'CJL Reverse' or 'CL5FLAGA20 Rev' primers may be used for lambda libraries, and 'Lib-GS-Rev' or 'VH-GSFLAGA20-Rev' primers may be used for the human PBMC VH library.

The reverse transcription primer should have at least the same 5' end sequence as the subsequent PCR reverse primer, to avoid residual primers left over from the reverse transcription reaction creating amplification products that have different 3' end sequences. This is especially important if the shorter 'Ck Reverse', 'CJL Reverse', or 'Lib-GS-Rev' primers are used for RT because any residual amount of these primers may participate in the following PCR and create products that lack the poly-A tail.

TABLE 1

| \multicolumn{2}{c}{Oligonucleotide primers used for amplification of library selection outputs} | |
|---|---|
| Ck Reverse | GTCGTCGTCGTCCTTGTAGTCGAAGACAGA TGGTGCAGCCACAGTTCG |
| Ck5-FlagA20 Rev | TTTTTTTTTTTTTTTTTTTAAATAGCGGATG CCTTGTCGTCGTCGTCCTTGTAGTCGAAGACA GATGGTGCAGCCACA |
| CJL Reverse | GTCGTCGTCGTCCTTGTAGTCAGTGACAGT GGGGTTGGCCTTGGGCTGACCKAGGACGGT |
| CL5FLAG A20 Rev | TTTTTTTTTTTTTTTTTTTAAATAGCGGATG CCTTGTCGTCGTCGTCCTTGTAGTCAGTGACA GTGGGGTTGGCCTTG |
| Lib-GS-Rev (VH, PBMC) | CGCTACCTCCGCCGCCAGAC |
| VH-GSFLAGA20-Rev | TTTTTTTTTTTTTTTTTTTAAATAGCGGATG CTTTGTCATCATCATCTTTATAATCGCTACCT CCGCCGCCAGAC |

Exemplary RT Reaction Conditions

For a reaction of a 200 µL final volume, a RT reaction may be set up as follows:

| Beads (in water) | X µL |
|---|---|
| $dH_2O$ | to 108 µL |
| 10 µM reverse primer | 2 µL |
| 10 mM dNTP | 10 µL |

Incubate at 65° C. for 5 min, chill on ice. Add:

| | |
|---|---|
| 5x First Strand Buffer | 40 µL |
| 0.1 M DTT | 20 µL |
| RNase OUT | 10 µL |

The reaction may be incubated at 42° C. for 2 minutes prior to adding 10 µL SuperScript II reverse transcriptase. The reaction may be divided into 100 µL aliquots and incubated at 42° C. for 50 minutes with occasional agitation. Tubes may then be incubated at 95° C. for 5 min after the reaction. Beads may be isolated and the supernatant transferred to new tubes. Typically samples may be pooled if they are from same selection output. Re-suspend beads in water (half of RT volume). Tubes may be incubated at 95° C. for 5 minutes after reaction, and the beads may be captured by magnet, and the supernatant may be pooled with previously transferred supernatant. This represents the cDNA template for PCR amplification of selection outputs.

17. Library Selection Against Cell Surface Antigen

The major distinctions between selecting PROfusion library against cell surface antigens and soluble biotinylated antigens are that the mRNA moieties in the PROfusion molecules are protected from cellular RNase degradations by cDNA complementation, and thus need to be reverse-transcribed into cDNA before library selections. The reverse transcription reaction may be carried out before or after the FLAG purification depending on the volume of library after oligo-dT purification. It is important to note that the reducing agent DTT should not be included in the reverse transcription, or any step prior to library selection, in order to preserve the intrachain disulfide bonds of the scFv molecule.

A: Library Preparation After Oligo dT Purification

In one embodiment, an initial 10 ml translation volume appropriate for first round selection may be used, but it should be noted that the following methodology may be easily adapted for smaller translation reactions.

PROfusion molecules may be translated and purified by oligo dT as described above. The purified library should be recovered in a dH$_2$O volume equal to or less than the reticulate lysate volume used for translation. Input, last wash buffer, and 10 µl of library may be counted to determine yield and percent recovery as described above.

B: FLAG Binding

The oligo dT-purified library may be equilibrated to a final concentration of 1×PBS by adding ¼ library volume 5×PBS. The amount of anti-FLAG M2 agarose beads needed to capture all PROfusion molecules may be estimated (e.g. estimating the binding capacity of the beads at approximately 6 nmol fusion protein per mL of 50% slurry). In order to have sufficient bead volume for manipulation during binding and washing, it is inadvisable to use less than 200 µL of the pre-washed beads. A wide-bore pipette tip may be used to transfer anti-FLAG M2 agarose to a new tube. The beads may be spun down (1500 rpm for 1 minute) and the buffer removed. The beads may be washed two to three times with 1 ml PBS to remove any trace amount of detergent present in the storage buffer. The oligo-dT purified library may be transferred in 1×PBS to the washed anti-FLAG M2 agarose beads, and rotated at 4° C. for 1 hour to overnight.

C: FLAG Washing

As an optional step, the anti-FLAG M2 agarose beads may be spun down at 1500 rpm for 1 minute, 4° C. and the supernatant discarded. 1×PBS may be used to transfer beads onto a Bio-Rad™ Mini-spin column or Invitrogen™ Microcentrifuge Spin Column, and then the buffer may be removed by spinning at 1000 rpm for 10 seconds. The Invitrogen™ column may be spun at higher speed (e.g. 10,000 RPM is possible). Beads may be washed 4× by 500-600 µL 1×PBS and the PBS spun through the column Beads may be washed 2× by 500-600 1×RT first strand buffer (without DTT). The flow-through may be discarded, but it is advisable to save the last wash for scintillation counting.

D: FLAG Elution

PROfusion molecules may be eluted by adding 450 µL (note that 230 µL may be used for smaller M2 agarose volumes) of 100 µg/mL FLAG peptide in First Strand Buffer (without DDT) that contains RNaseOUT at a 1:20 dilution, and then incubating the mixture for 10 minutes at room temperature. Eluate may be collected by spinning at 3000 rpm or faster for 20 seconds. This step may be repeated once, and then the libraries from both elutions may be pooled.

E: FLAG Recovery Calculation

Count 5-10 µL of elution output and 100 µL from the last wash on a beta counter. PROfusion molecule recovery % may be calculated as follows (note that 10-30%, or higher, recovery is expected):

$$=(CPM_{output} \times Volume_{output})/(CPM_{input} \times Volume_{input})$$

F: Reverse Transcription

Primers described in section 16 above may be used.

RT Reaction Conditions

| | | |
|---|---|---|
| Purified PROfusion library | 445 µL | 890 µL |
| 10 µM reverse primer | 5 µL | 10 µL |
| 10 mM dNTP | 25 µL | 50 µL |
| Superscript II | 25 µL | 50 µL |
| Total volume | 500 µL | 1000 µL |

Reaction may be incubated at 37° C. for 1 hour, with or without agitation.

The library may be equilibrated for selection against cell surface antigens as follows. After the reverse transcription reaction has been completed, 5 M NaCl may be added to the reaction mixture to 75 mM (15.3 µL to 1 mL and 7.6 to 500 µL reaction). An additional 1×PBS may be added to the library if there is a need to increase volume. The following blocking reagent may be added to library before selection.

| | | Final concentration |
|---|---|---|
| BSA, 50 mg/ml | 21 µL | 1 mg/ml |
| Salmon sperm DNA, 10 mg/ml | 10.5 µL | 0.1 mg/ml |

A pre-clear step may be required for naïve library selection, but may be omitted if using a library made from a single template, e.g. a library made for affinity maturation.

Cells used for library pre-clearing (antigen-naïve cells) should be confirmed not to have target antigen expression on cell surface by flow-cytometry or Western blot analysis. For example, this could be the parental cells used for generating the antigen-expressing stable cell lines, which present a situation where the only know surface protein difference between the cells used for pre-clearing and for selection should be the target antigen itself.

The cell numbers needed for pre-clearing library should be calculated. This is the number of antigen-naïve cells needed for pre-clearing library and is the same number as for library selection. The cell number (X) is calculated from several numbers: copies of antigens on antigen-expressing cell surface (C), library size for selection (S=moles×6×10$^{23}$), and fraction of library that will bind to the target antigen (F). It can be roughly calculated by this formula to allow for 10 fold excess of target antigen or pre-clear power:

$$X=10 \times S \times F/C$$

For instance, assume one particular antigen has an estimated cell surface copy number of $1 \times 10^4$, and in a 10 pmol naïve antibody library less than 0.05% ($5 \times 10^{-4}$) of the library can be recovered by antigen binding or background sticking. The number of cells needed for pre-clear and selection is $$X=10 \times (10 \times 10^{-12} \times 6 \times 10^{23}) \times (5 \times 10^{-4})/(1 \times 10^4) = 3 \times 10^6$$

In practice, the number of cells should be $5 \times 10^6$ or more to ensure cell pellet can be seen after pelleting.

G: Pre-Clear the Library

Cell density may be counted by hemocytometer or Coulter counter and sufficient cells may be transferred to a centrifuge tube. Cells may be spun down at 1500 rpm at 4° C., and very gently re-suspended in 1 mL ice-chilled PBS. The cell suspension may be transferred to a 1.7 mL screw-top microfuge tube. Be careful not to shear cells by pipetting. Cells may be spun down at 1500 rpm and the PBS removed. The wash step with PBS may be repeated once more. The library from step 13.3.3 should be immediately added to gently re-suspended cells. The tubes may then be immersed into an ice-water bath, and agitated for about 60 minutes. Cells may be spun down at 1500 rpm and the library transferred to a new tube of cells for second pre-clear or for antigen selection.

H: Library Selection Against Antigen-Expressing Cells

Calculate the number of cells needed for antigen selection. This is the same number as for pre-clearing library as calculated above. The cell number (X) is calculated from several numbers: copies of antigens on antigen-expressing cell surface (C), library size for selection (S=moles$\times 6 \times 10^{23}$), and fraction of library that will bind to the target antigen (F). It can be roughly calculated by this formula to allow for 10 fold excess of target antigen or pre-clear power:

$$X=10 \times S \times F/C$$

I: Library Selection

Antigen-expressing cell density may be counted by hemocytometer or Coulter counter and sufficient antigen-expressing cells may be transferred to a centrifuge tube. Cells may be spun down at 1500 rpm at 4° C., and very gently re-suspend cells in 1 mL ice-chilled PBS. The cell suspension may be transferred to a 1.7 mL screw-top microfuge tube. Be careful not to shear cells by pipetting. Spin cells down at 1500 rpm and remove PBS and repeat wash with PBS once more. The purified and/or pre-cleared library may be immediately used to gently resuspend cells. The tubes may be immersed into ice-water bath, and rotated for 2 hours. Spun down at 1500 rpm and the supernatant discarded. Cells may be washed 4 times with 1 mL PBS, spun down at 1500 rpm and the supernatant discarded. Cells may be re-suspended in 500 µL of PBS. If desired, count up to 20% of cells and last wash.

J: Library Output Recovery

5 µL RNase H (2 U/µL) may be added to the re-suspended cells and incubated at 37° C. for 20 minutes. This will digest the RNA and release cDNA from the cell surface. Cells may be spun down at 1500 rpm for 30 seconds and the supernatant transferred to a new tube. Cells may now be discarded. 5 µL of RNase A (20 mg/ml) may be added to the supernatant and incubated at 37° C. for 30 minutes. This degrades any cellular RNA that may have come from broken cells during the selection process. The degraded RNA may be removed by dialysis later and thereby prevented from interfering with library amplification by PCR. To the supernatant add equal volume of phenol/$CHCl_3$/isoamylalcohol (25:24:1) and vortex for 30 seconds. The bottom organic phase may be separated from top aqueous phase by centrifugation in Phase Lock Gel Heavy 2 ml tube (Eppendorf) at maximal speed for 5 minutes. The top aqueous phase may be transferred to a new tube and the extraction repeated once with phenol/$CHCl_3$/isoamylalcohol (25:24:1) and once by $CHCl_3$. The top aqueous phase after the $CHCl_3$ extraction may be transferred to Mini Dialysis Kit, 8 kDa cut-off, 2 mL (GE healthcare) and dialyzed overnight at 4° C. against 4 liter of $dH_2O$.

K: Counting and Library Selection Recovery Calculation

Starting from Round 3 count 10-20% of the last wash and the cells.

$$\text{Selection recovery \%} = 100 \times CPM_{Total\ Cells}/CPM_{Total\ Input}$$

18. Reamplification of Library DNA by RT-PCR

Reverse transcription may be performed using the material captured from the library. Reagents and protocols known in the art are suitable for performing the reverse transcription reaction. The volume of the reaction may be scaled up or down according to the bead volume after selection.

Primers used for reverse transcription may be any suitable reverse-complementary sequences located at the 3' end invariable region of the antibody library and may be the same or further 3' to the reverse primer to be used in a subsequent amplifying PCR.

An exemplary reverse transcription reaction contains the beads from the library selection (in water), reverse primer, and dNTP. Reactions are incubated at 65° C. for about 5 minutes and chilled on ice. First strand synthesis buffer, about 0.1M DTT, and RNase inhibitor are then typically added to the reaction. The reverse transcription reactions are incubated at about 42° C. for 2 minutes before adding reverse transcriptase enzyme. Reactions are incubated at about 42° C. for 50 minutes with occasional agitation. Reactions are then incubated at 95° C. for 5 min. Beads are then collected by magnet, and the supernatant is transferred to new tubes, which is pooled if it is from same selection output. Beads are resuspended in water (half of RT volume), and incubated in tubes at 95° C. for 5 minutes. Beads are again collected using a magnet, and the supernatant is pooled with the previously transferred supernatant. This contains the cDNA template for PCR amplification of selection output. After PCR, 10-□L of PCR product is loaded onto a 2% agarose gel to confirm that the reaction was successful.

19. PCR for Library DNA Template Amplification

For selection outputs from the first and second rounds, cDNA (supernatants from RT reactions) may be dialyzed against water using an 8 kDa cut-off, and the entire amount of cDNA may be used as PCR template. For selection outputs from later rounds, 10% of cDNA may typically be used as template for PCR, and dialysis is typically not necessary. Reactions may be performed in 1 mL PCR volumes for round 1 and 2 outputs (using all RT products), while reaction volumes may be scaled down for outputs from later rounds. Aliquots for 100-µL reactions should be made from a master mix. An exemplary PCR reaction for library DNA template amplification is shown in Table 7 below.

TABLE 2

Exemplary PCR reaction for library DNA template amplification

| DNA template | X µL |
|---|---|
| dH$_2$O add to | 740 µL |
| 10X KOD buffer | 100 µL |
| MgSO$_4$ (25 mM) | 60 µL |

TABLE 2-continued

Exemplary PCR reaction for library DNA template amplification

| DNA template | X μL |
|---|---|
| 10 mM dNTP | 20 μL |
| 5' forward primer (10 μM) | 30 μL |
| 3' reverse primer (10 μM) | 30 μL |
| KOD Hot Start DNA Polymerase | 20 μL |
| Total volume | 1000 μL* |

In an exemplary embodiment, 1 mL PCR reactions are used for round 1 and 2 outputs, and 0.5 mL reactions are used for outputs from later rounds. Aliquots of 100-μL reactions should be made from a master mix. Exemplary thermal cycling conditions for library DNA template amplification are shown in Table 8 below.

TABLE 3

Exemplary alternative PCR reaction for library DNA template amplification

| cDNA template | X μL |
|---|---|
| dH₂O | add to 790 μL |
| 10X High Fidelity Taq DNA Polymerase buffer | 100 μL |
| MgSO₄ (50 mM) | 40 μL |
| 10 mM dNTP | 20 μL |
| 5' forward primer (10 μM) | 20 μL |
| 3' reverse primer (10 μM) | 20 μL |
| High Fidelity Taq DNA Polymerase | 10 μL |
| Total volume | 1000 μL |

In an exemplary embodiment, 1 mL PCR reactions are used for round 1 and 2 outputs, and 0.5 mL reactions are used for outputs from later rounds. Aliquots of 100-□L reactions should be made from a master mix. Exemplary thermal cycling conditions for library DNA template amplification are shown in Table 8 below.

TABLE 4

Another exemplary alternative PCR reaction for library DNA template amplification

| DNA template | X μL |
|---|---|
| dH₂O | add to 660 μL |
| 10X KOD buffer | 100 μL |
| MgSO₄ (25 mM) | 60 μL |
| 2 mM dNTP | 100 μL |
| 5' forward primer (10 μM) | 30 μL |
| 3' reverse primer (10 μM) | 30 μL |
| KOD Hot Start DNA Polymerase | 20 μL |
| Total volume | 1000 μL* |

Thermal Cycling Conditions for Library DNA Template Amplification

| 95° C. | 2 minutes |
|---|---|
| 95° C. | 20 seconds |
| 55° C. | 10 seconds |
| 70° C. | 15 seconds |

} 20 cycles*

| 70° C. | 30 seconds |
|---|---|
| 4° C. | Hold forever |

*Note: 18 to 20 cycles of amplification may typically be used with KOD Hot Start DNA Polymerase, however, as few as 13 cycles may be successful in amplifying a sufficient quantity of library DNA. Non-specific products of various sizes may become more apparent with additional amplification cycles, and the product may need to be gel purified. If possible, it may be helpful to increase the DNA template input rather than the number of amplification cycles.

TABLE 5

Thermal cycling conditions for library DNA template amplification

| 94° C. | 2 minutes |
|---|---|
| 94° C. | 20 seconds |
| 55° C. | 20 seconds |
| 68° C. | 1 minute |

} 25 cycles*

| 68° C. | 5 minute |
|---|---|
| 4° C. | Hold forever |

*Note: 25 cycles typically give sufficient amplification but it may be increased to as many as 35 cycles to gain more products. Non-specific products of various sizes may become more apparent with additional amplification cycles, and the product may need to be gel purified. If possible, it may be helpful to increase the DNA template input rather than the number of amplification cycles.

After PCR, the size of the PCR product is confirmed by, e.g., agarose gel electrophoresis. If products are the correct size (~850 bp for scFv, ~500 bp for VH or VL library) and minimal non-specific products are present, the products can generally be used either directly in transcription reaction of the next round, or after purification with a spin column (e.g. Qiagen™ QIAquick PCR Purification Kit). In some cases, the PCR products may need to be gel purified. If gel purification is to be used for PCR products, separate all remaining products on a preparative agarose gel and cut out the specific band for gel extraction. Quantitation of gel purified DNA may be misleading, as residual EtBr in the DNA tends to interfere with the UV absorbance. A more extensive wash step during gel extraction may help alleviate this interference. If possible, DNA concentration should be measured on a spectrophotometer, as the UV scanning traces are quite different between a clean DNA sample and a DNA with residual EtBr. This protocol is subsequently repeated to conduct multiple rounds of selection.

A: VH CDR3 Spectratyping PCR

Spectratyping PCR may be used to analyze the VH CDR3 size distributions in the library, or its selection outputs. It is a useful tool to assess the library diversity, as well as the progression of the selections. The initial few rounds of library selection outputs and the library before selection should be very diverse and the CDR3 size distribution approximates a Gaussian distribution.

TABLE 6

Spectratyping PCR primers

| 6-FAM-PanVHFR3-Fwd | GACACGGCCGTGTATTACTGT |
|---|---|
| PanJH-Rev | GCTGAGGAGACGGTGACC |

Spectratyping PCR Setup

| cDNA template | 2.0 μL |
|---|---|
| dH₂O | 18.1 μL |
| 5X GoTaq Flexi reaction buffer | 6.0 μL |

-continued

| | |
|---|---|
| 25 mM MgCl$_2$ | 1.8 μL |
| 10 mM dNTP | 0.6 μL |
| 5' forward primer (10 μM) | 0.6 μL |
| 3' reverse primer (10 μM) | 0.6 μL |
| GoTaq Flexi DNA polymerase | 0.3 μL |
| Total volume | 30.0 μL |

Promega GoTaq DNA polymerase is used in this setup but may be substituted by thermal stable DNA polymerases from other sources. The final Mg$^{2+}$ concentration is 1.5 mM.

| Theraml cycling program | | |
|---|---|---|
| 94° C. | 2 minutes | |
| ↓ | | |
| 94° C. | 20 seconds | |
| 55° C. | 20 seconds | 30 cycles |
| 72° C. | 30 seconds | |
| ↓ | | |
| 72° C. | 5 minute | |
| ↓ | | |
| 4° C. | Hold forever | |

B: Spectratyping Electrophoresis and Analysis

After the PCR, 10-μL product may be loaded onto a 2% agarose gel to confirm successful reaction and the remaining product may be submitted to sequencing core facility for spectratyping electrophoresis on a sequencing machine, along with a ROX-labeled DNA size marker, which in generally underestimates the size of the DNA product by 3-bp, possibly due to the difference in the labeling dyes.

The amplified DNA product has the following organization:

5'-FR3 (27 bp)-VH CDR3-FR4 (35 bp)-3'

The VH CDR3 size is deduced from the apparent DNA produce size as determined by the Rox dye size marker by the following calculation:

$$\text{Size}_{VH\ CDR3} = (\text{Size}_{Apparent\ DNA\ product\ size} - 60)/3$$

Where $60 = (62_{Frameworks\ on\ both\ ends} - 1_{3'\ A\ overhang} + 3_{DNA\ marker\ underestimation})$ 16. Exemplary Reagents and Buffer Compositions

| 10X Chemical Ligation Buffer | |
|---|---|
| Tris, pH 7 | 250 mM |
| NaCl | 1 M |

| Oligo-dT Binding Buffer | 1X | 2X | 3X |
|---|---|---|---|
| Tris, pH 8 | 100 | 200 | 300 mM |
| NaCl | 1 | 2 | 3 M |
| Triton X-100 | 0.05 | 0.1 | 0.15% |

| FLAG Binding Buffer | 1X | 5X |
|---|---|---|
| Phosphate-based buffer | | |
| PBS | 1X | 5X |
| Triton X-100 | 0.025 | 0.125% |
| Alternative HEPES-based buffer | | |
| HEPES | 50 | 250 mM |

| FLAG Binding Buffer | 1X | 5X |
|---|---|---|
| NaCl | 150 | 750 mM |
| Triton X-100 | 0.025 | 0.125% |

| Selection Buffer | |
|---|---|
| Phosphate-based buffer | |
| PBS | 1X |
| BSA | 1 mg/mL |
| Salmon sperm DNA | 0.1 mg/mL |
| Triton X-100 | 0.025% |
| Yeast tRNA (optional, add before use) | 20 ng/mL |

| Alternative HEPES-based buffer | |
|---|---|
| HEPES | 50 mM |
| NaCl | 150 mM |
| BSA | 1 mg/mL |
| Salmon sperm DNA | 0.1 mg/mL |
| Triton X-100 | 0.025% |
| Yeast tRNA (optional, add before use) | 20 ng/mL |

| First strand buffer | |
|---|---|
| Tris-HCl, pH 8.3 | 250 mM |
| KCl | 375 mM |
| MgCl$_2$ | 15 mM |

| 50X FLAG stock solution | |
|---|---|
| FLAG peptide | 25 mg |
| Selection buffer | 5 mL |

Make 1 mL aliquots and store at −20° C.

| FLAG elution solution | |
|---|---|
| 50X FLAG stock solution | 1 mL |
| Selection buffer | 49 mL |

Make 1 mL aliquots and store at −20° C.

Oligo-dT Cellulose Preparation

Weigh 2.5 g of oligo-dT cellulose in a 50 mL tube.
Add 25 mL of 0.1 N NaOH and mix.
Spin down at 1500 rpm for 3 minutes, discard the supernatant.
Wash the oligo-dT cellulose with 25 mL of 1× Oligo-dT binding buffer.
Spin down at 1500 rpm for 3 minutes, discard the supernatant.
Repeat the wash 3 more times and measure the pH of the supernatant.
The pH should be the same as wash buffer (~pH 8.5).
Re-suspend the oligo-dT cellulose to a final volume of 25 mL by adding
1× Oligo-dT binding buffer. This may be an approximately 50% slurry.
Store the pre-washed cellulose beads at 4° C.
Final concentration=100 mg/mL=1 nmol RNA capacity.

Anti-FLAG M2 Agarose Preparation
Transfer 25 mL of M2 agarose beads into a 50 mL of tube.
Spin down beads for 5 minutes at 1000 rpm in a Beckman centrifuge and remove supernatant by aspiration.
Wash by re-suspending beads in equal volume of 10 mM glycine, pH 3.5.
Spin down beads for 5 minutes at 1000 rpm in a Beckman centrifuge and remove supernatant by aspiration.
Re-suspend with one column volume of 1×FLAG binding buffer.
Spin down slurry for 5 minutes at 1000 rpm in a Beckman centrifuge and remove supernatant by aspiration.
Repeat the wash 3 times.
Re-suspend with one column volume of 1× binding buffer (containing 1 mg/mL BSA and 100 mg/mL salmon sperm DNA).
Tumble 1 hour or overnight at 4° C.
Aliquot in 2 mL fractions if desired and keep at 4° C.

Example 1

Demonstration of Functional mRNA-scFv Molecules

Four known antibodies were used to demonstrate that functional mRNA-scFv molecules can be displayed and bind to their respective antigen: D2E7 (human anti-hTNF), Y61 (human anti-hIL-12), 17/9 (mouse anti-HA), and MAK195 (mouse anti-hTNF). The MAK-195 scFv was generated by PCR from plasmid DNA using the primers shown in Table 9 below.

TABLE 7

Oligonucleotide Primers Used For The Construction Of MAK195 mRNA-scFv Constructs

| Primers | Sequences |
|---|---|
| T7-MAK195VH-Fwd | TAATACGACTCACTATAGGGACAATTACTATTT ACAATTACACCATGGAGGTGCAGCTGAAGGAG TCAGG (SEQ ID NO: 22) |
| MAK195VhGS-Rev | CGATCCGCCACCGCCAGAGCCACCTCCGCCTGA ACCGCCTCCACCTGCAGAGACAGTGACCAGAGT CC (SEQ ID NO: 23) |
| MAK195VLGS-Fwd | GGTGGAGGCGGTTCAGGCGGAGGTGGCTCTGG CGGTGGCGGATCGGACATTGTGATGACCCAGTC TC (SEQ ID NO: 24) |
| MAK195VL-Rev | GATGGTGCAGCCACCGTACGTTTTATTTCCAAC TTTGTCCCCGAG (SEQ ID NO: 25) |

An anti-HA 17/9 scFv (see Schulze-Gahmen et al. (1993) J. Mol. Biol. 234(4): 1098-118) was generated by PCR using the following primers based on protein sequences A31790 and B31790 downloaded from NCBI's database (see Table 10 below).

TABLE 8

Oligonucleotide Primers Used For The Construction Of 17/9 mRNA-Scfv Constructs

| Primers | Sequences |
|---|---|
| T7TMVUTR-17/9 VH-1 Fwd | GGACAATTACTATTTACAATTACACCATGGAAG TGCAGCTGGTGGAAAGCGGCGGCGATCTGGTG AAACC (SEQ ID NO: 26) |

TABLE 8-continued

Oligonucleotide Primers Used For The Construction Of 17/9 mRNA-Scfv Constructs

| Primers | Sequences |
|---|---|
| 17/9 VH-2 Rev | GCTGCTAAAGCTAAAGCCGCTCGCCGCGCAGCT CAGTTTCAGGCTGCCGCCCGGTTTCACCAGATC GCCG (SEQ ID NO: 27) |
| 17/9 VH-3 Fwd | GGCTTTAGCTTTAGCAGCTATGGCATGAGCTGG GTGCGCCAGACCCCGGATAAACGCCTGGAATG GGTGG (SEQ ID NO: 28) |
| 17/9 VH-4 Rev | GCCTTTCACGCTATCCGGATAATAGGTATAGCC GCCGCCGTTGCTAATGGTCGCCACCCATTCCAG GCGT (SEQ ID NO: 29) |
| 17/9 VH-5 Fwd | CCGGATAGCGTGAAAGGCCGCTTTACCATTAGC CGCGATAACGCGAAAAACACCCTGTATCTGCAG ATG (SEQ ID NO: 30) |
| 17/9 VH-6 Rev | GTTCGCGGCGCGCGCAATAATACATCGCGCTAT CTTCGCTTTTCAGGCTGCTCATCTGCAGATACA GGGT (SEQ ID NO: 31) |
| 17/9 VH-7 Fwd | ATTGCGCGCGCCGCGAACGCTATGATGAAAAC GGCTTTGCGTATTGGGGCCAGGGCACCCTGGT GACCGT (SEQ ID NO: 32) |
| 17/9 VH-8 GS Rev | CGATCCGCCACCGCCGCTGCCACCTCCGCCTGA ACCGCCTCCACCCGCGCTCACGGTCACCAGGGT GCCC (SEQ ID NO: 33) |
| GS-17/9 VL-1 Fwd | AGCGGCGGTGGCGGATCGGATATTGTGATGACC CAGAGCCCGAGCAGCCTGACCGTGACCGCGGG CGAAA (SEQ ID NO: 34) |
| 17/9 VL-2 Rev | TGTTTGCCGCTGTTAAACAGGCTCTGGCTGCTG GTGCAGCTCATGGTCACTTTTTCGCCCGCGGTC ACGG (SEQ ID NO: 35) |
| 17/9 VL-3 Fwd | GTTTAACAGCGGCAAACAGAAAAACTATCTGA CCTGGTATCAGCAGAAACCGGGCCAGCCGCCG AAAGTG (SEQ ID NO: 36) |
| 17/9 VL-4 Rev | CGGTAAAGCGATCCGGCACGCCGCTTTCGCGGG TGCTCGCCCAATAAATCAGCACTTTCGGCGGCT GGCC (SEQ ID NO: 37) |
| 17/9 VL-5 Fwd | TGCCGGATCGCTTTACCGGCAGCGGCAGCGGCA CCGATTTTACCCTGACCATTAGCAGCGTGCAGG CGGA (SEQ ID NO: 38) |
| 17/9 VL-6 Rev | AAAGGTCAGCGGGTTGCTATAATCGTTCTGGCA ATAATACACCGCCAGATCTTCCGCCTGCACGCT GCTA (SEQ ID NO: 39) |
| 17/9 VL-7 Fwd | AGCAACCCGCTGACCTTTGGCGGCGGCACCAAA CTGGAACTGAAACGTACGGTGGCTGCACCATCT GTCT (SEQ ID NO: 40) |

TABLE 8-continued

Oligonucleotide Primers Used For The Construction Of 17/9 mRNA-Scfv Constructs

| Primers | Sequences |
|---|---|
| 17/9 VL-8 FLAG Rev | TTAAATAGCGGATGCCTTGTCGTCGTCGTCCTT GTAGTCGATGAAGACAGATGGTGCAGCCACC (SEQ ID NO: 41) |

17/9 antibody sequence was retrieved from NCBI database using the accession numbers A31790 and B31790.

DNA constructs for these scFv were transcribed in vitro and then translated by rabbit reticulocyte lysate either as mRNA-scFv (protein was attached to mRNA via linker with puromycin modification) or as free scFv (protein was not attached to mRNA). Both types of molecules were purified and subjected to pull-down assays by corresponding biotinylated antigens (see FIG. 4).

Figures 4A, 4B:
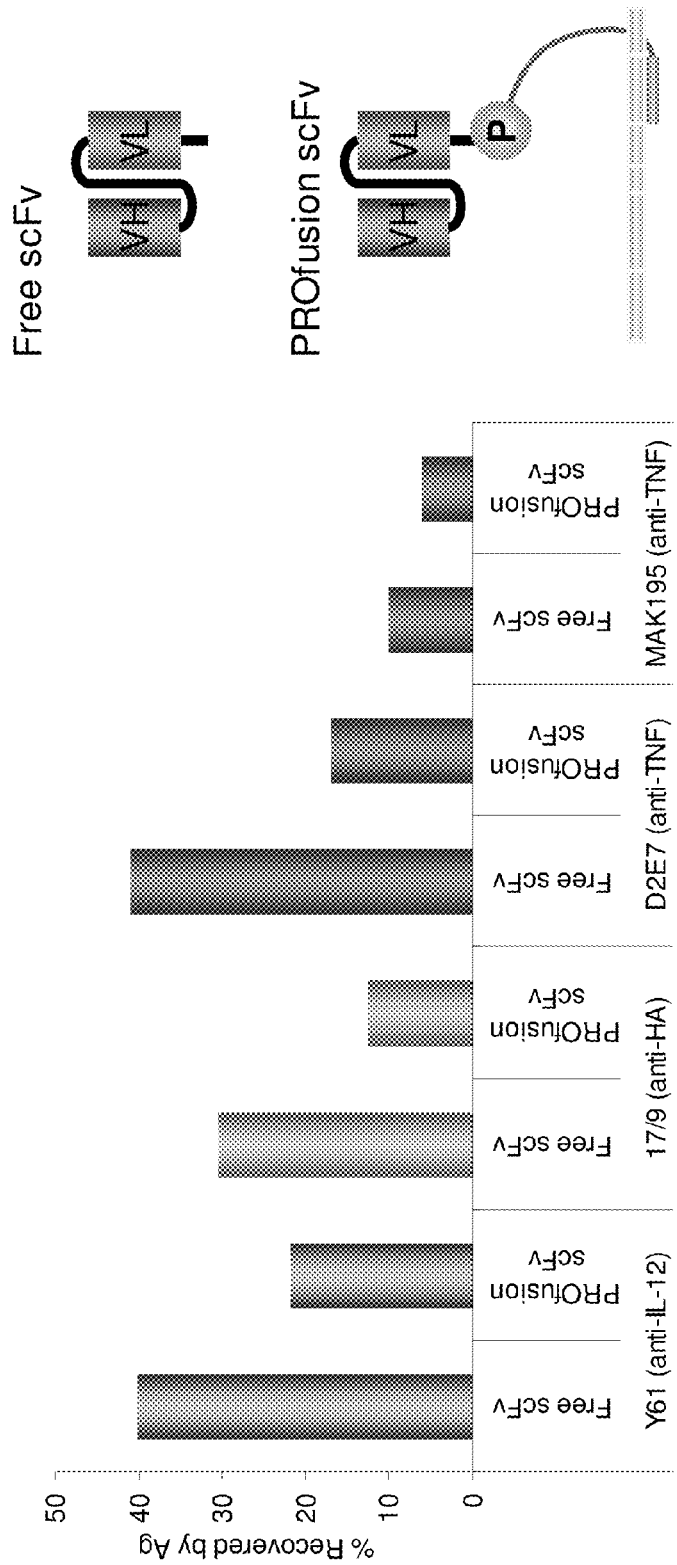
FIG. 4a depicts results showing that functional scFv can be generated as mRNA-scFv molecules.
FIG. 4b depicts models of free scFv molecules and mRNA-scFv molecules.
Figure 5:
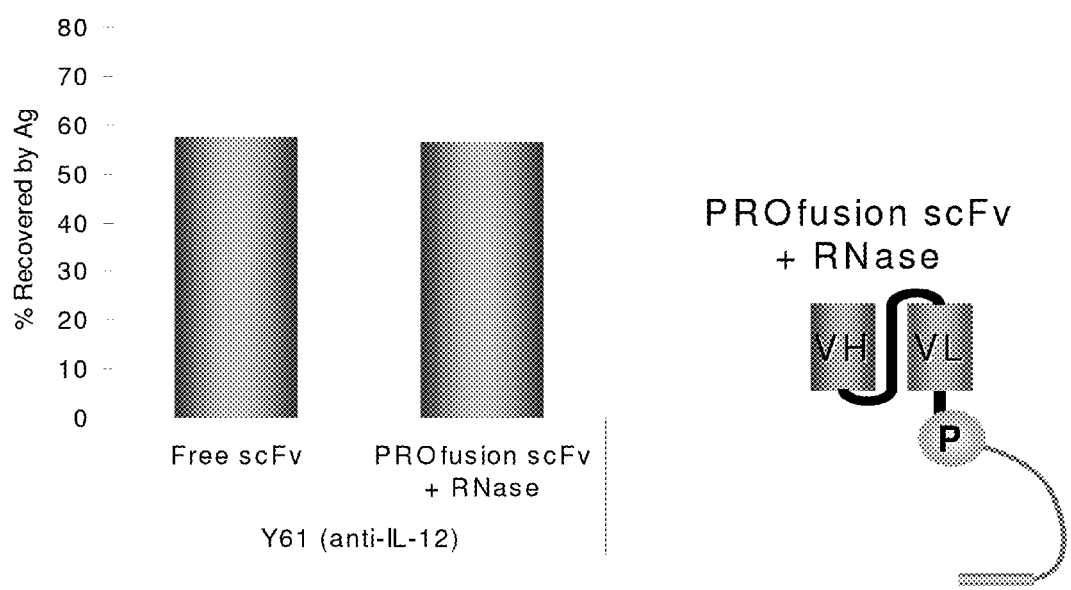
FIG. 5 depicts results showing that the scFv attached in the mRNA-scFv molecule format is functionally equivalent to the free scFv molecule.

The data in FIG. 4 shows that functional m-RNA-scFv (bound to biotinylated antigen) can be pulled down by streptavidin-magnetic beads, albeit at lower percent recovery than free scFv. Further experiments showed that this difference is simply due to the heavy RNA tethered to the scFv. RNase degradation of the RNA portion from the mRNA-scFv molecule restored the scFv recovery by antigen to the same level as that of free scFv (see FIG. 5).

Example 2

Optimization of the mRNA Display Technology to Improve the Translation Reaction

In a preferred embodiment, the library size is $1 \times 10^{12}$. About 20 pmol of the fused protein (e.g., $1.2 \times 10^{13}$) is required for the selection in order to cover the library size 12 times. Recovery following FLAG-purification is typically about 30%. Therefore, about 60 pmol of the fused protein is needed following Oligo-dT purification to input into FLAG purification. In one embodiment, about 1.2 pmol fused protein is obtained per 100 pmol RNA following Oligo-dT purification. In this embodiment, about 5 nmol RNA (which covers the library size 3000 times) is necessary to obtain 60 pmol of the fused protein. Note that this calculation does not take into account the observation that only about 20-30% of fused mRNA display molecules are functional (can be recovered after selection).

Due to the aforementioned quantity of the fused protein needed for subsequent steps of the mRNA display method, the translation reaction was optimized to maximize protein recovery. Varying the initial amount of RNA input into the translation reaction was evaluated following FLAG purification. Protein recovery was assessed by measuring the percentage of $S^{35}$ methionine incorporated during the translation reaction, and by calculating the ratio of pmol protein (output) to pmol RNA (input). The starting amounts of input RNA tested, as well as the resulting protein recovery, are shown in Table 12. As demonstrated by this analysis, a lower RNA input surprisingly leads to a higher percentage of protein recovery.

TABLE 9

Relationship Between RNA Input And Protein Recovery

| RNA input | After FLAG purification | |
|---|---|---|
| into translation (for 1 vial of lysate) | % incorporated $S^{35}$ Met | pmol Protein/pmol RNA |
| 400 pmol | 0.40% | 1/400 = 0.25% |
| 200 pmol | 0.67% | 1.7/200 = 0.85% |
| 100 pmol | 0.99% | 2.5/100 = 2.5% |
| 50 pmol | 0.76% | 1.9/50 = 3.8% |
| 25 pmol | 0.73% | 1.8/25 = 7.2% |

The translation reaction was also performed using different amounts of the free amino acid mixture to determine the effect on protein recovery. The relative starting amounts of the amino acid mixture tested, as well as the resulting protein recovery, are shown in Table 13. The RNA input in each case was 50 pmol. As demonstrated by this analysis, increasing the amino acid pool leads to a decrease in translation efficiency.

TABLE 10

Relationship Between Amino Acid Concentration And Protein Recovery

| | After FLAG purification | |
|---|---|---|
| Amino Acid Mixture | % incorporated $S^{35}$ Met | pmol Protein/ pmol RNA |
| 1x | 1.60% | 2/50 = 4% |
| 2x | 0.42% | 0.5/50 = 1% |
| 3x | 0.13% | 0.77/50 = 0.3% |
| 4x | 0.03% | 0.04/50 = 0.07% |

Different amounts of "cold" (i.e., non-radioactive) methionine were also tested for their effect on translation efficiency. The different concentrations of cold methionine that were tested, as well as the resulting protein recovery, are shown in Table 14. The RNA input in each case was 50 pmol. As demonstrated by this analysis, increasing the input of cold methionine does not lead to an increase in translation efficiency.

TABLE 11

Relationship Between Cold Methionine Concentration And Protein Recovery

| Cold Methionine | After FLAG purification | |
|---|---|---|
| Concentration | % incorporated $S^{35}$ Met | pmol Protein/pmol RNA |
| 5 µM | 1.00% | 1.31/50 = 2.6% |
| 17.5 µM | 0.23% | 1.15/50 = 2.3% |
| 30 µM | 0.20% | 1.52/50 = 3.0% |
| 42.5 µM | 0.15% | 1.58/50 = 3.2% |

The RNA input and amino acid concentration should therefore be taken into consideration when planning the translation reaction for mRNA display. While decreasing the RNA input in each reaction may improve protein recovery, it may also impact library size. An exemplary RNA translation reaction that may be useful in practicing the mRNA display method of the invention is shown in Table 15.

TABLE 12

Exemplary RNA Translation Reaction

| | |
|---|---|
| In vitro transcribed RNA | 100 pmol = 29-36 μg |
| Translation Mixture (including amino acid mixture, not including methionine) | 15 μl |
| $^{35}$S Methionine | 2 μl |
| Reticulocyte Lysate | 200 μl |
| 100 mM oxidized glutathione/ 10 m reduced glutathione | 3.3 μl |
| PDI (1 U/μL) | 6 μl |
| H$_2$O | to 300 μL |
| Reaction conditions | 30° C. for 60-90 minutes |

Example 3

Optimization of the mRNA Display Technology for scFv Selection

Spacer Length

Figure 6:
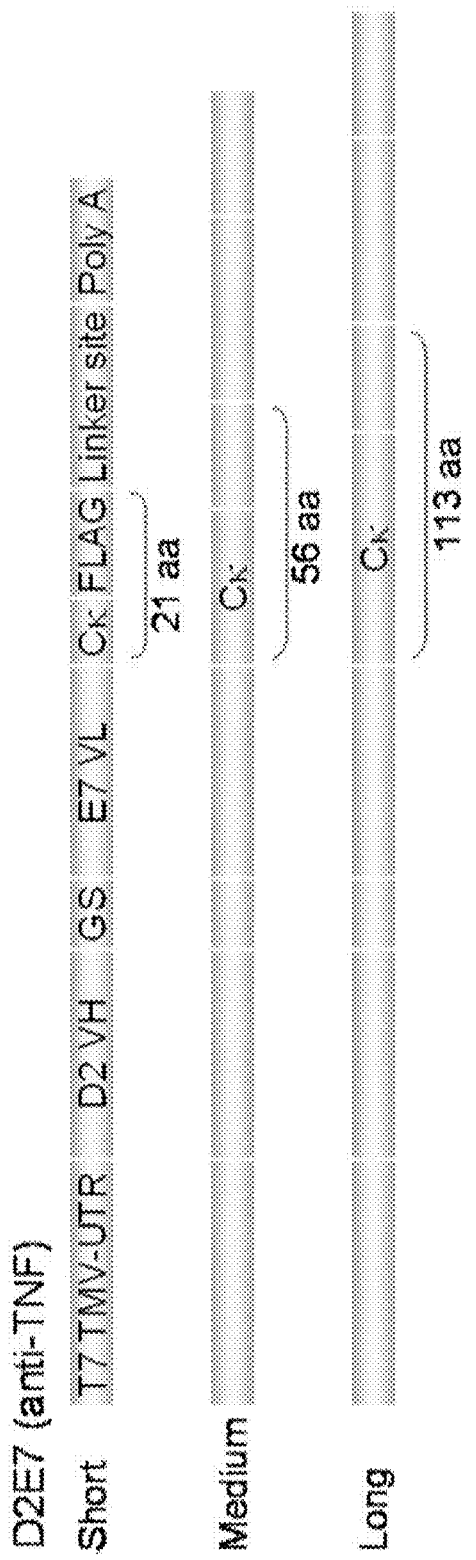
FIG. 6 depicts the three D2E7 mRNA-scFv constructs with different 3' spacer lengths.
Figure 7:
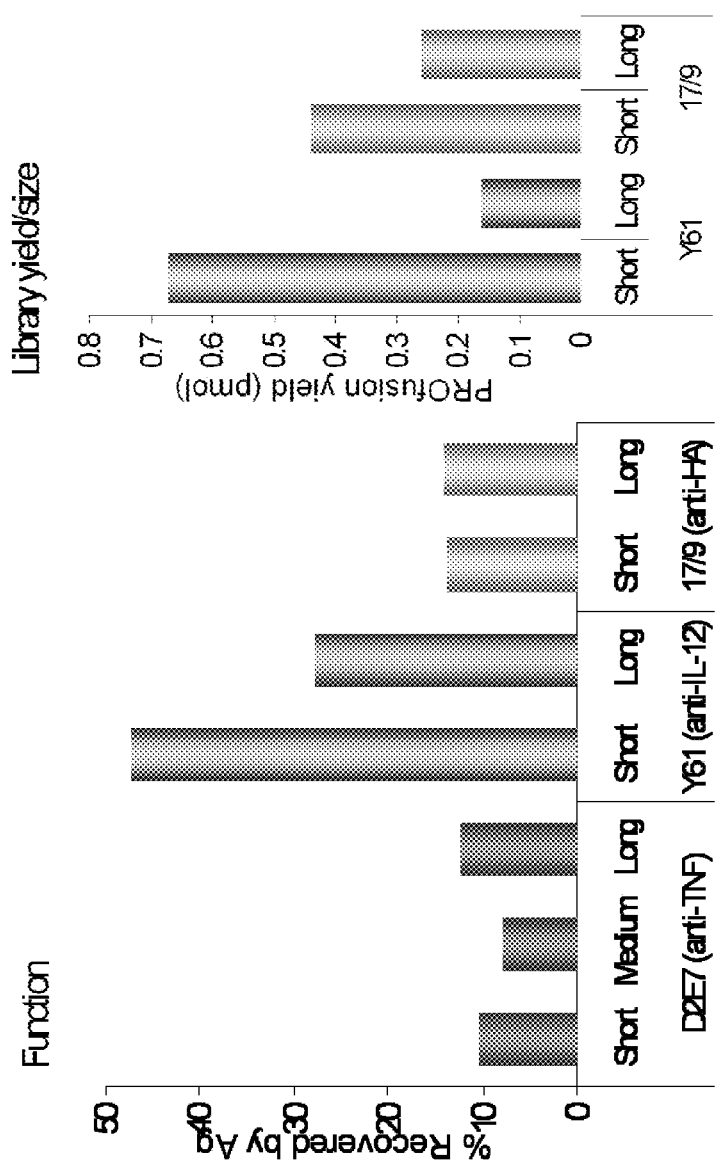
FIG. 7 depicts results showing that shorter spacer length improved mRNA-scFv binding to antigens and the yield of mRNA-scFv antibody molecules.
Figure 8:
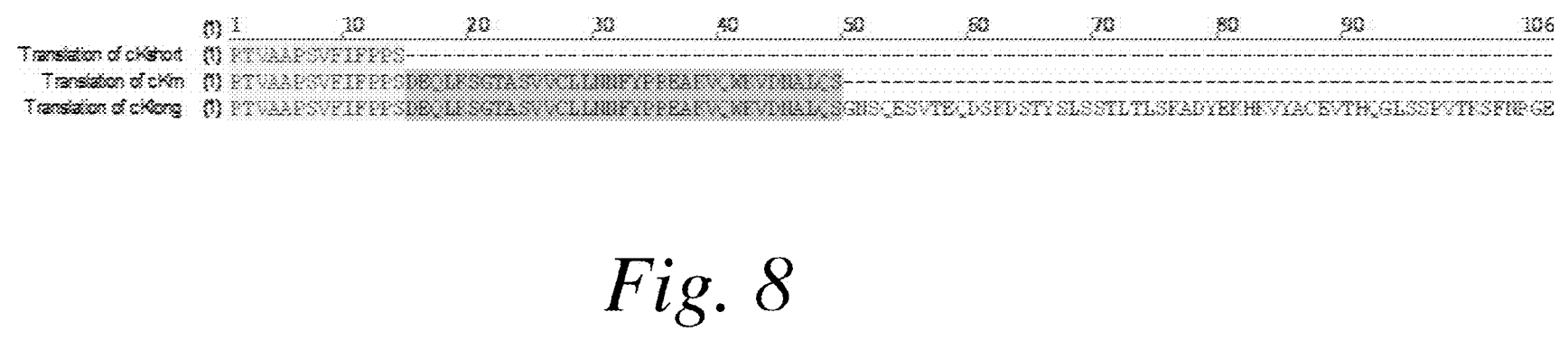

It has been previously proposed that a long spacer length between the scFv protein and the end of mRNA improved scFv folding and function (see Hanes et al. (1997) Proc. Natl. Acad. Sci. USA 94 (10):4937-42). Therefore, the effect of the spacer length between the scFv and the linker annealing site on the mRNA-scFv molecule function and yield was investigated (see FIG. 6). Three different D2E7 scFv constructs with short, medium and long 3' spacers and two short and long spacer constructs for Y61 and 17/9 scFv were made (see FIG. 8 for D2E7 spacer constructs). The results, depicted in FIG. 7, show that a longer spacer does not provide measurable advantage in the mRNA-scFV molecule's function as assessed by antigen binding. Moreover, longer spacer length significantly reduced the mRNA-scFv yield (see FIG. 7). RNA yields were also lower with a longer spacer: short spacer yielded 6 nmol RNA; medium spacer yielded 3.4 nmol RNA; and long spacer yielded 1.7 nmol. Thus, in one embodiment, a short spacer is preferred for scFv library construction.

Figure 23:
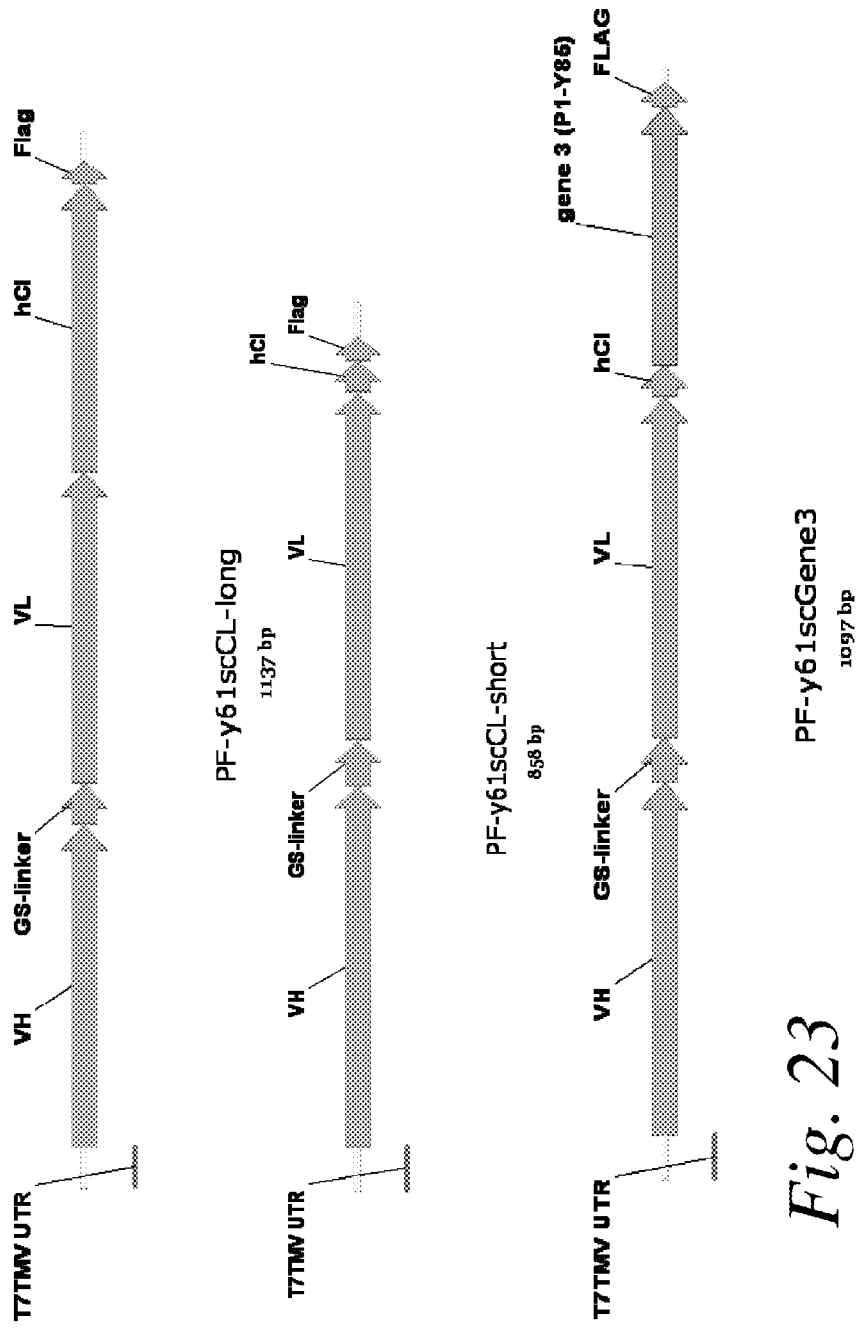
FIG. 23 depicts the mRNA-scFv Y61 constructs with short and long spacer lengths as well as the PF-y61scGene3 construct comprising a poly-A tail at the DNA linker between the mRNA and scFv protein.
Figure 24:
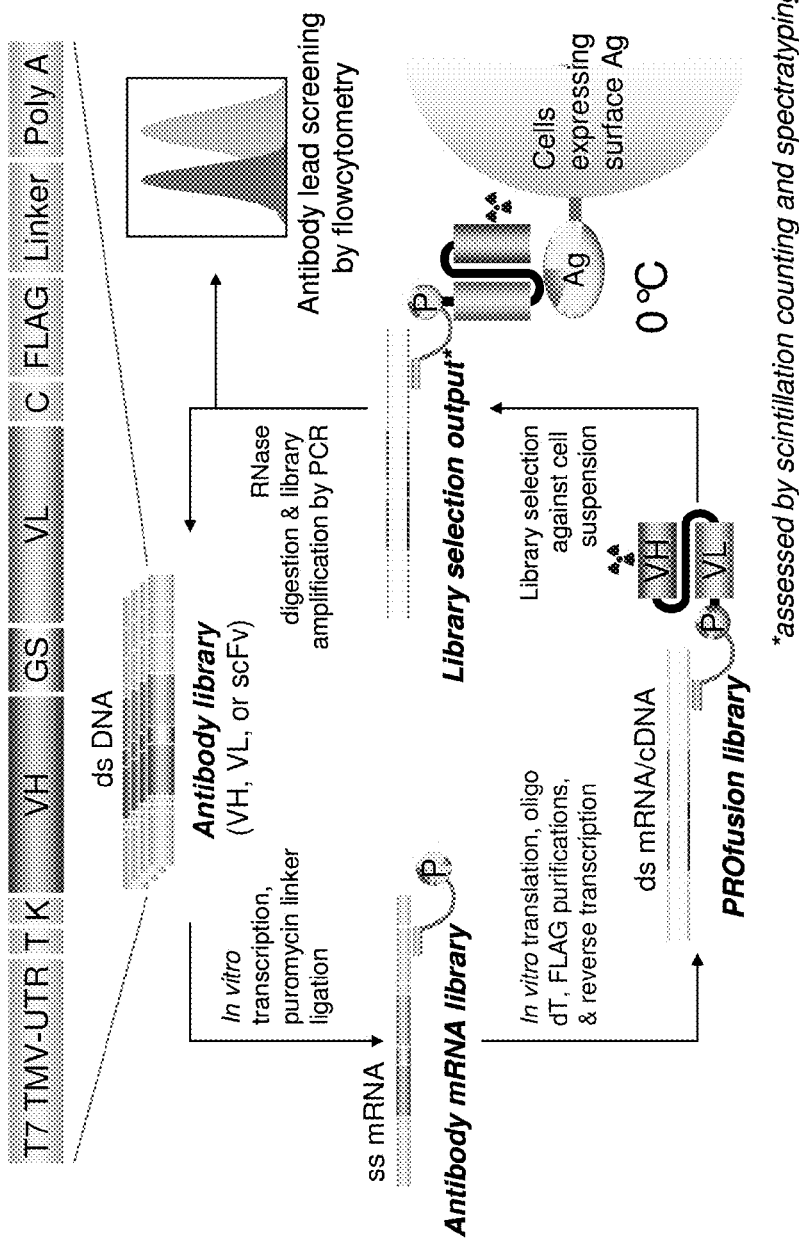
FIG. 24 depicts a general scheme for the mRNA-scFv display technology in other embodiments of the invention.

Comparison of different spacers and linkers was also performed using three different Y61 constructs (see FIG. 23). The results, shown below in Table 16, show that RNA yields were also lower with a longer spacer. In addition, there was no difference in mRNA molecule purifications nor antigen binding by moving the poly-A tail from the mRNA itself (Y61-scGene3pA) to the DNA linker between mRNA and scFv protein (Y61-scGene3) as the scFv protein are identical between these two constructs as shown in SEQ ID NO:10 and SEQ ID NO:4, respectively.

TABLE 13

Comparison of Different Spacers and Linkers

| | Percent of Recovery | | |
|---|---|---|---|
| Construct | Oligo dT purification | FLAG purification | IL-12 (50 nM selection) |
| Y61-scCL-short | 1.00% | 51.3% | 21.1% |
| Y61-scGene3 | 0.46% | 50.3% | 8.0% |
| Y61-scGene3pA | 0.45% | 47.4% | 6.1% |

As shown below, 17/9 requires PDI during translation to be functional, and DTT in the reverse transcription reaction before selection was shown to affect its antigen binding. As these results indicate, disulfide bonds are essential for 17/9 function, and this makes 17/9 a good candidate to investigate spacer length requirements. FIG. 9 shows that although longer spacer length does not improve mRNA-scFv molecule binding to antigen, it reduces its yield.

Example 4

Optimization of the mRNA Display Technology to Improve scFv Protein Folding and Function Omission of Chemical Modification on Cysteine Residues Messenger RNA display technology in the art includes a chemical capping reaction on free cysteine residues to prevent formation of undesirable cysteine disulfide bonds by 2-nitro-5-thiocyanatobenzoic acid, which resulted in cyanylation, or by N-ethylmaleimide, which covalently links to the sulfhydryl group. While this capping reaction eliminates potential protein misfolding caused by random crosslinking of free cysteine residues, the present invention eliminates the artificial preservation of free cysteine within an antibody which can be a detriment to its future manufacturability due to unpredictable physical or chemical properties. The step of chemical capping was eliminated such that any extra free cysteine beyond the four cysteines required for scFv Ig domain folding are not actively preserved during the library selection.

Example 5

Optimization of the mRNA Display Technology to Improve scFv Protein Folding and Function Requirement of a Co-Translational Protein Disulfide Isomerase Activity It has been suggested that PDI contributes to better protein function and secretion by either isomerase or chaperone activity or both (see Shusta et al. Nat Biotechnol 16 (8):773-7; Smith et al. Biotechnol Bioeng 85 (3): 340-50). Two Ig intra-domain disulfide bonds are encoded by every scFv sequence, one in the VH and the other in the VL domain. It has been suggested that a co-translational protein disulfide isomerase (PDI) activity is crucial for proper disulfide bond formation in vitro (see Ryabova et al. Nat Biotechnol 15 (1): 79-84). mRNA display protocols in the art have stipulated the inclusion of (PDI) in the translation reaction.

Figure 10:
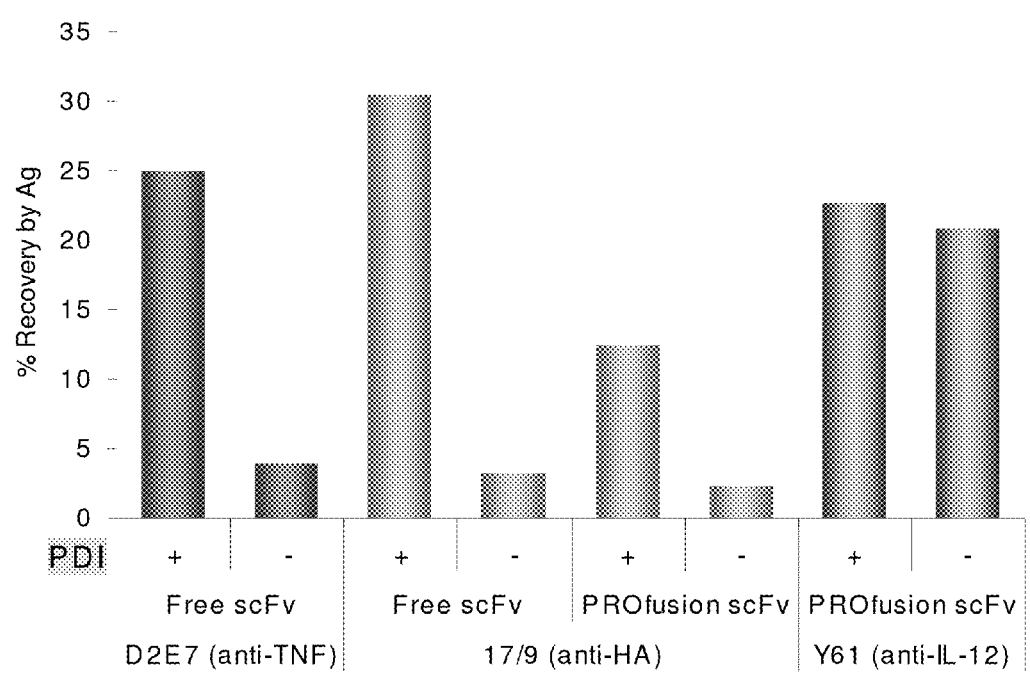
FIG. 10 depicts results showing that PDI activity was required for some scFv function.

D2E7, Y61, and 17/9 scFv were used to test their requirement of PDI activity in the mRNA display system. The results showed that two of the scFv (D2E7 and 17/9) would not bind to their cognate antigen without PDI during their generation whereas Y61 appeared to be unaffected (see FIG. 10). It was concluded that at a large antibody library level, the high diversity would require PDI activity to ensure maximal scFv function.

The recovery and functionality of D2E7 scFv translated with or without additional PDI added was also tested. The translation reaction included 1 tube lysate (200 μl), 100 pmol D2E7 short spacer RNA and PDI and oxidized glutathione/reduced glutathione. Translation without PDI excluded PDI and oxidized glutathione/reduced glutathione. The translated protein was recovered with FLAG purification, and the recovery amount was quantified. Antigen binding/recovery was then performed with 50 mM biotinylated TNFα and equal inputs for each, 100000 cpm. The results are shown in below in Table 17.

TABLE 14

Testing D2E7 scFv +/− PDI

| Translation | FLAG Recovery (cpm) | FLAG Recovery (% input) | Antigen Binding Recovery |
|---|---|---|---|
| D2E7 + PDI | 290000 cpm | 1.6% | 25% |
| D2E7 − PDI | 460000 cpm | 2.5% | 4% |

The results showing that Y61 does not require PDI during translation for functionality are shown below in Table 18.

TABLE 15

Y61-Sccl-Short Does Not Require
PDI During Translation For Functionality

| | | % of Recovery | | |
|---|---|---|---|---|
| PDI | RT | Oligo dT purification | FLAG purification | IL-12 (50 nM) selection |
| No | No | 0.57% | 34.0% | 18.9% |
| No | Yes | | 9.2% | 20.8% |
| Yes | No | 0.50% | 31.9% | 24.3% |
| Yes | Yes | | 9.8% | 22.7% |

The results showing that 17/9 requires PDI during translation for functionality are shown below in Table 19.

TABLE 16

17/9 Requires PDI During Translation For Functionality

| | | % of Recovery | | | |
|---|---|---|---|---|---|
| | PDI | Oligo dT purification | FLAG purification | HA (50 nM) selection | No Ag selection |
| Free protein | No | N/A | N/A | 3.3% | N/A |
| | Yes | | 30.5% | 0.7% | |
| Ligated protein | No | 3.4% | 27.6% | 2.3% | N/A |
| | Yes | 2.5% | 39.3% | 12.4% | 0.8% |

Example 6

Optimization of the mRNA Display Technology to Improve scFv Protein Folding and Function Removal of Dithiothreitol from Reaction Dithiothreitol (DTT) is a reducing agent commonly introduced to enzymatic reactions to minimize protein aggregation and reduced protein oxidation. It is also typically used in the reverse transcription (RT) reaction following in vitro translation step of the mRNA scFv molecules. Since its inclusion may reduce the two intrachain disulfide bonds in a scFv molecule that are produced by PDI activity, the potential effect of DTT on the scFv antigen binding function was investigated (see FIG. 11). The presence of DTT significantly abolished the antigen binding activity of 17/9 scFv after RT, which is consistent with the dependence of PDI activity for 17/9 function shown in FIG. 11. This loss of antigen binding activity was not due to the RT reaction itself, since most antigen binding activity of 17/9 was preserved if DTT was omitted from the RT. Furthermore, the results show that the 17/9 scFv cDNA was indeed reverse transcribed from the mRNA in the absence of DTT by PCR, suggesting that DTT is dispensable from the RT reaction (data not shown).

Figure 12:
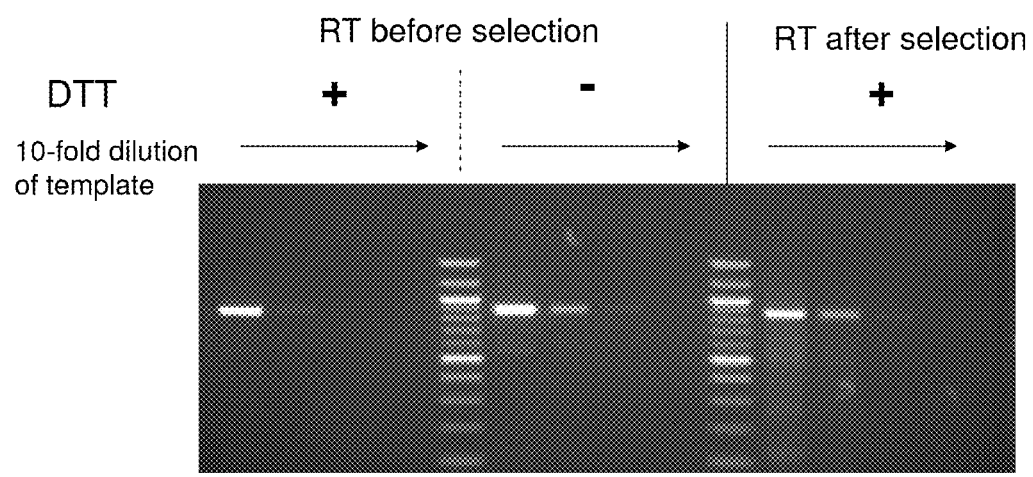
FIG. 12 depicts agarose gel electrophoresis results showing that DTT did not significantly alter the reverse transcription process.

The results showing that DTT in the RT reaction before selection impacts 17/9 functionality are shown below in Table 20. As shown in FIG. 12, however, DTT does not impact the RT process.

TABLE 17

DTT in RT reaction before selection impacts 17/9 functionality

| | | % of Recovery | | | |
|---|---|---|---|---|---|
| PDI | RT | Oligo dT purification | FLAG purification | HA (50 nM) selection | No Ag selection |
| No | No | 3.4% | 27.6% | 2.3% | N/A |
| Yes | No | 2.5% | 39.3% | 12.4% | 0.8% |
| | Yes, w/o DTT | | 14.2% | 9.4% | N/A |
| | Yes, with DTT | | 9.9% | 2.0% | N/A |

Figure 11:
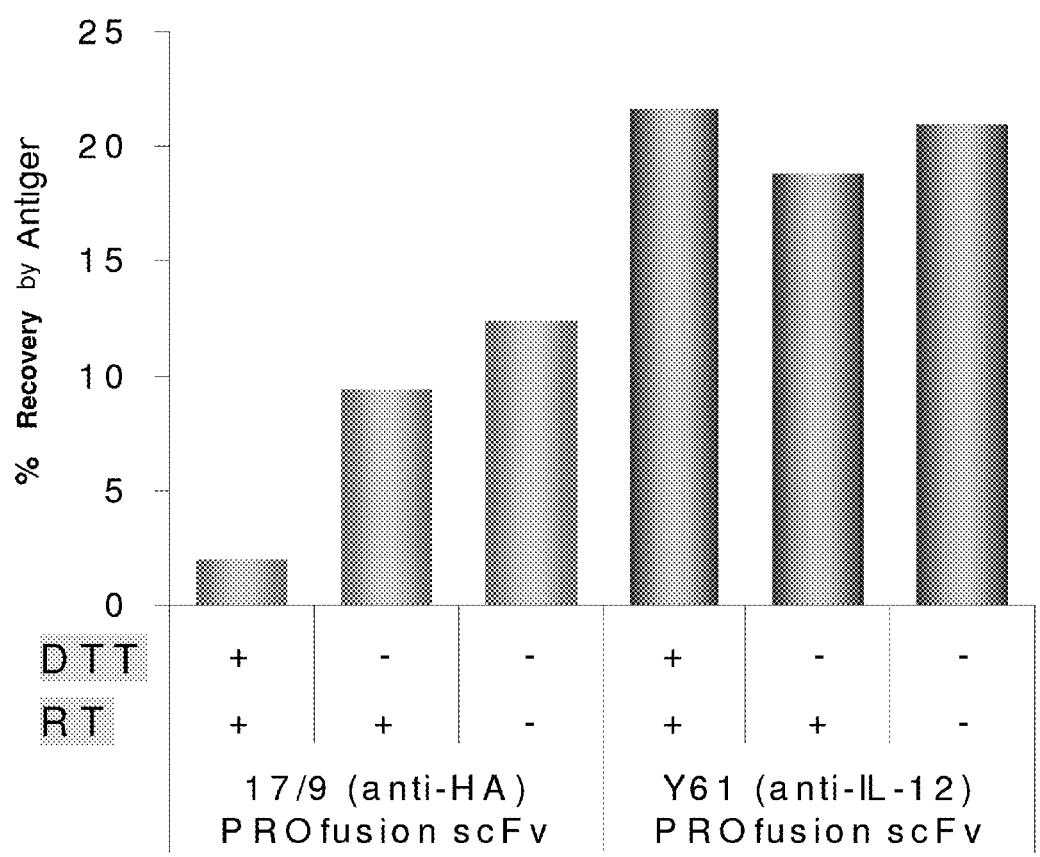
FIG. 11 depicts results showing that the presence of DTT during reverse transcription inhibited 17/9 scFv binding to hemaglutinin (HA) antigen.
Figure 13:
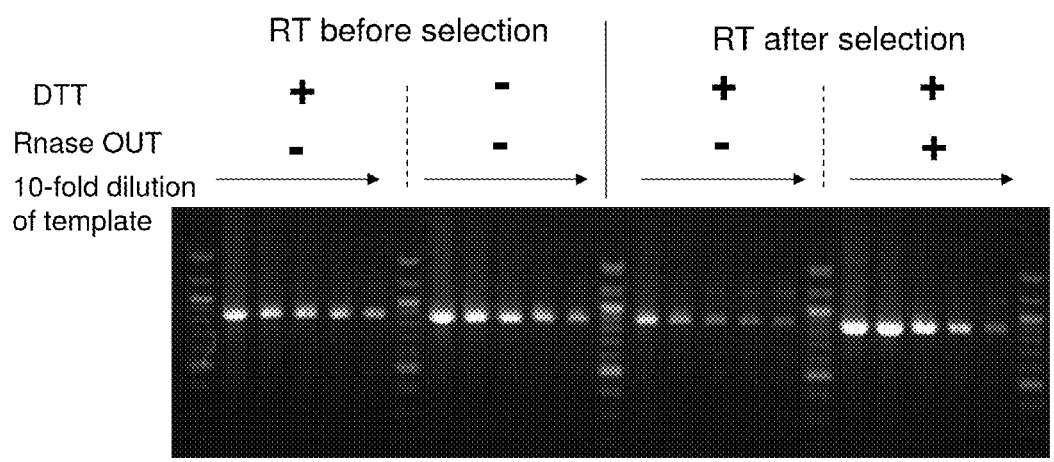
FIG. 13 depicts agarose gel electrophoresis results from different RT conditions with or without DTT and RNase-OUT™ both before and after selection.

In contrast to the 17/9 scFv, the anti-IL-12 Y61 scFv function was not affected by DTT (see FIG. 11). This is consistent with its aforementioned insensitivity to PDI activity, and suggests that not all antibody scFv will require disulfide bonds for function. The different RT conditions explored for Y61-scCL-short and corresponding results are shown below in Table 21 and also in FIG. 13.

TABLE 18

Different RT conditions for Y61-scCL-short

| | | | % of Recovery | | |
|---|---|---|---|---|---|
| RT | DTT in RT reaction | RNase OUT in selection | Oligo dT purification | FLAG purification | IL-12 (50 nM) selection |
| Before selection | Yes | No | 1.6% | 25.9% | 21.6% |
| Before selection | No | No | | 29.3% | 18.8% |
| After selection | Yes | No | | 56.1% | 22.2% |
| After selection | Yes | Yes | | | 21.0% |

In one embodiment, DTT is not present in the RT or alternatively the RT is delayed until after antigen selection to maximize production of functional scFv yield from the mRNA-scFv library. Tables 22 and 23 below show the results of delaying the RT step until after the antigen selection step for Y61-ScCL-long and Y61-ScCL-short, respectively.

TABLE 19

Comparing Y61-ScCL-long with or without RT step

| | | % of Recovery | | | |
|---|---|---|---|---|---|
| | RNA Yield | Oligo dT purification | FLAG purification | IL-12 (50 nM) selection | No Ag Selection |
| Free Protein | 3.2 nmoles | N/A | | 49.5% | 0.3% |
| Ligated Protein | | 13% | 57.6% | 31% | 0.2% |
| No RT step | | | | | |
| RT step | | | 15% | 28.6% | 0.3% |

TABLE 20

Comparing Y61-ScCL-short with or without RT step

| | | % of Recovery | | | |
|---|---|---|---|---|---|
| | RNA Yield | Oligo dT purification | FLAG purification | IL-12 (50 nM) selection | No Ag Selection |
| Free Protein | 4.7 nmoles | N/A | N/A | 40.2% | 0.2% |
| Ligated Protein No RT step | | 0.55% | 47.6% | 20.8% | 0.1% |
| RT step | | | 19.3% | 21.8% | 0.1% |

Example 7

Optimization of the mRNA Display Technology to Improve scFv Protein Folding and Function Inclusion of RNase Inhibitor During Antigen Selection The production of double-stranded mRNA-cDNA by RT was thought to prepare the mRNA-scFv molecules for antigen binding to prevent RNA degradation and reduce RNA secondary structures. After selection by antigen the cDNA can be recovered by alkaline hydrolysis of the mRNA and serves as amplification template by PCR. To avoid the potential impact of DTT on scFv function by RT prior to antigen selection, alternative methods need to be employed to protect the mRNA for amplification after selection.

Figure 14:
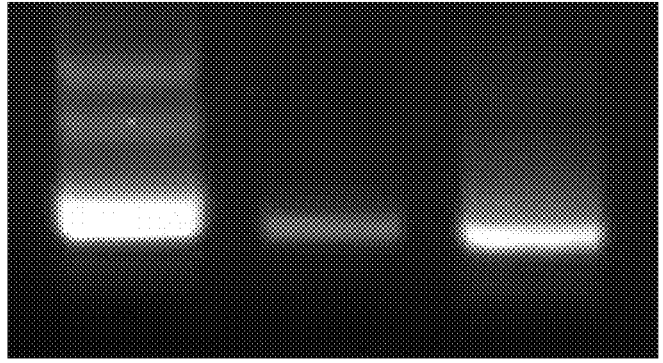
FIG. 14 depicts agarose gel electrophoresis results showing recovery of the Phylos 40 VH sequence when reverse transcribed either before or after selection compared with pre-selection RT and alkaline elution of cDNA (left lane).

Therefore, it was investigated whether the mRNA in an mRNA-VH molecule lacking its protective cDNA strand would be sufficiently stable and accessible for amplification by RT-PCR after antigen selection. A previously validated IL-1α binding mRNA-VH molecule was used as a model molecule. Recovery of the Phylos40 VH sequence was compared when RT was done before or after antigen selection (see FIG. 14). Compared to the method in the art (pre-selection RT and alkaline elution of cDNA, left lane), recovery of mRNA by RT-PCR after antigen selection appeared to be significantly reduced when the mRNA-IL-1α complex were captured on SA-magnetic beads and used directly for RT (right lane). This might be due to partial RNA degradation during antigen selection or poor mRNA accessibility on beads for RT. Attempts to interrupt IL-1α-Phylos40 VH interaction and dissociate the mRNA-VH molecule from SA beads by acid elution (at pH 3) for better mRNA accessibility appeared to worsen its recovery, possibly due to lowered mRNA stability or poor dissociation of the mRNA-VH molecule from its antigen into elution buffer before the complexes were removed with the SA beads. FIG. 14 shows results of reverse transcription following antigen selection comparing the standard method of RT-PCR following oligoDT with acid elution followed by RT-PCR and RT-PCR directly off of beads following capture. Dilution with free beads at 1:10, 1:100 and 1:1000 showed that strong re-amplification was achieved at a dilution of 1:1000.

Figure 15:
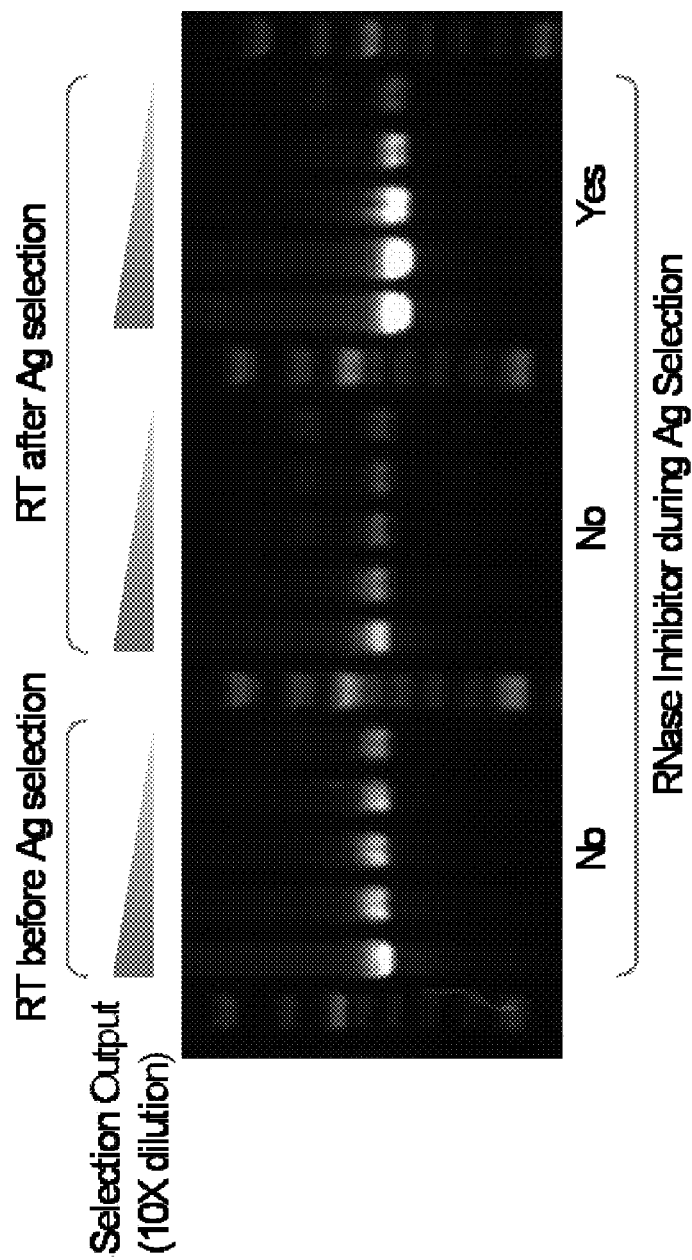
FIG. 15 depicts agarose gel electrophoresis results showing that an RNase inhibitor preserved RNA template recovery by reverse transcription after antigen selection.

Since it is possible to omit the RT prior to antigen selection and subsequently recover the mRNA by RT-PCR, it was investigated whether the reduced recovery of mRNA template can be restored or enhanced by protecting the RNA from contaminating RNase activity by RNase inhibitor. RNase-OUT™ (Invitrogen, cat. #10777-019) was included at 1:20 dilution during the antigen selection step and followed by RT-PCR to compare the mRNA recovery (see FIG. 15). Compare to performing RT before antigen selection, the mRNA template recovery again was reduced if RT was carried out after antigen selection without RNase inhibitor. Interestingly, the inclusion of RNase inhibitor to the antigen selection not only restored but also significantly enhanced mRNA recovery. Thus, it appears this enhancement is at least partly due to a better efficiency of capturing a lighter ~280 kDa mRNA-scFv molecule than that of a heavier ~560 kDa mRNA-scFv molecule with the additional cDNA.

Figure 16:
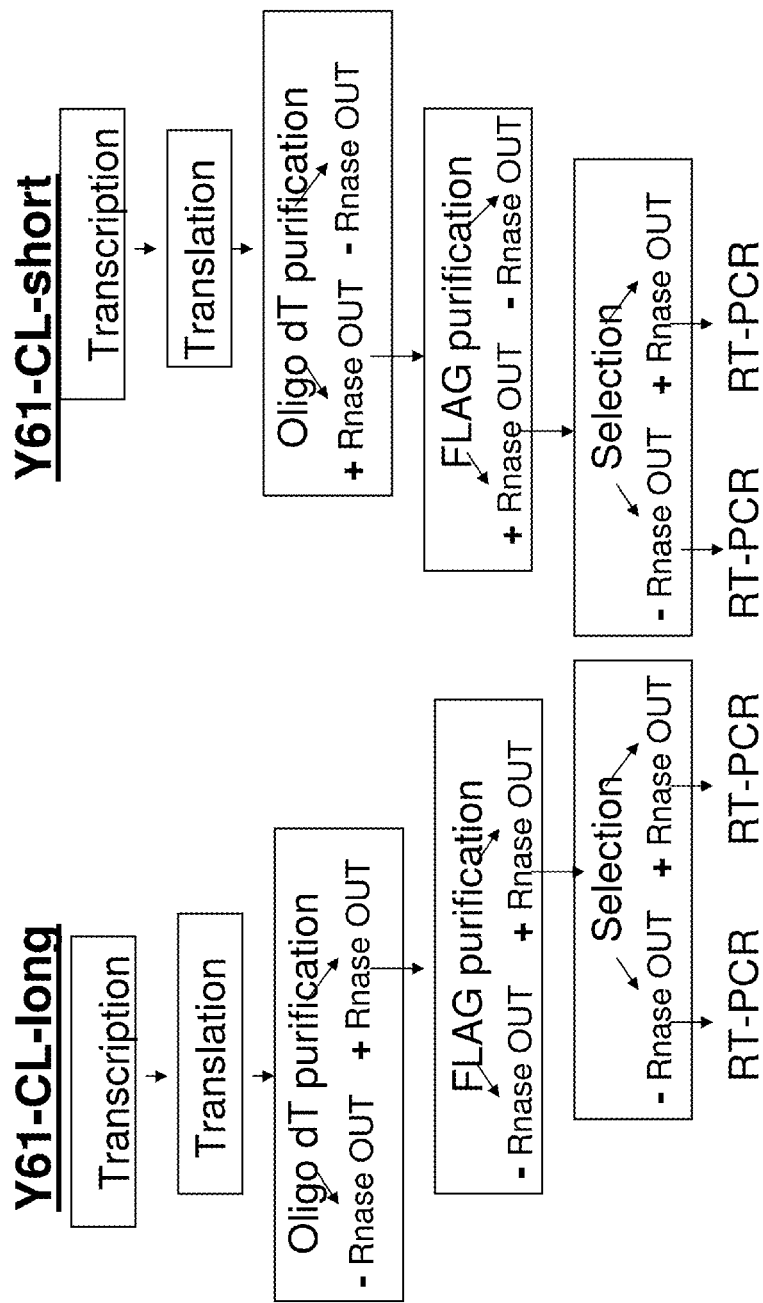
FIG. 16 depicts results of a side-by-side comparison of a CL-long and a CL-short spacer in the presence or absence of RNaseOUT™.
Figure 17:
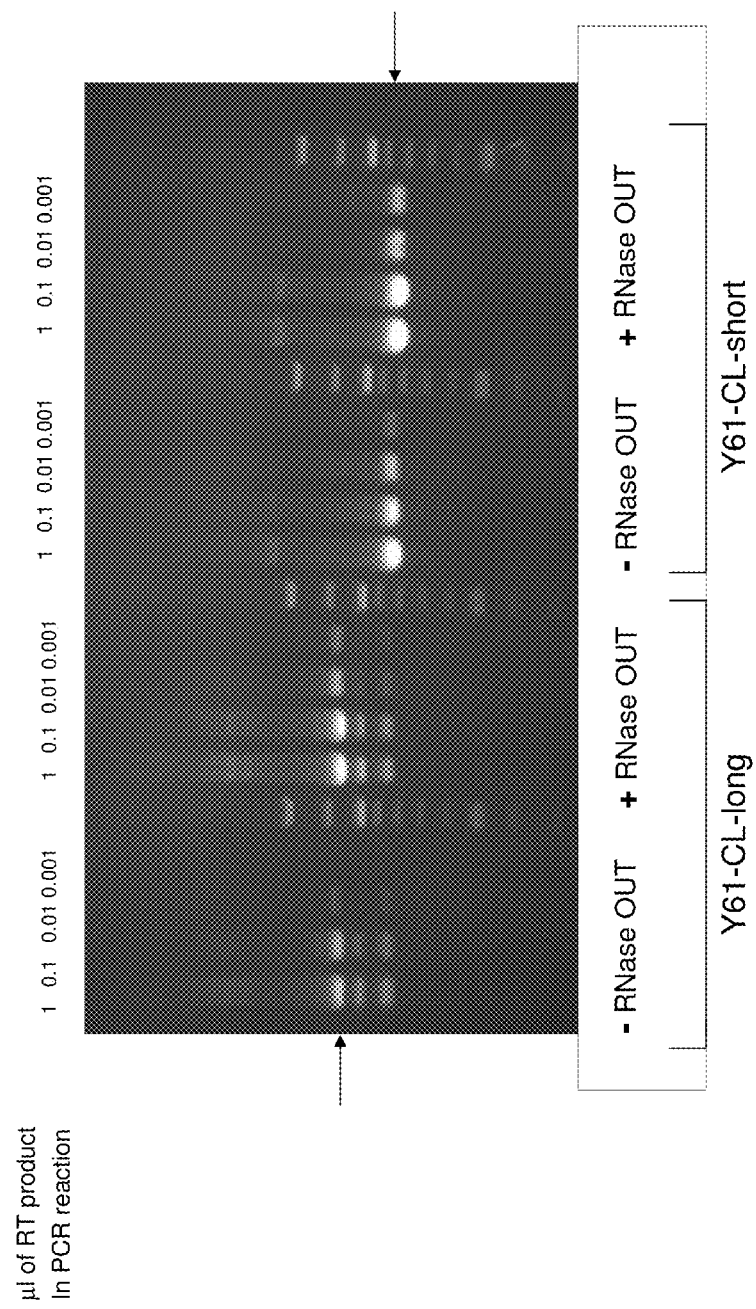
FIG. 17 depicts agarose gel electrophoresis results showing side-by-side comparison of recovery of a CL-long and CL-short spacer in the presence or absence of RNaseOUT™.

Inclusion of RNase OUT was also tested with an mRNA-scFv molecule. FIG. 16 depicts the experiment performed to compare Y61-CL-long with Y61-CL-short in the presence or absence of RNase OUT. The results can be seen in Table 24 below as well as in FIG. 17.

TABLE 21

Comparison Of CL-Long And CL-Short Spacer In The Presence Or Absence Of RNAseOUT

| | | % of Recovery | | |
|---|---|---|---|---|
| Construct | RNase OUT | Oligo dT purification | FLAG purification | IL-12 (50 nM) selection |
| Y61-scCL-long | No | 0.22% | 29.3% | 27.7% |
| | Yes | 0.25% | 30.5% | 33.8% |
| Y61-scCL-short | No | 0.64% | 42.2% | 47.2% |
| | Yes | 0.59% | 46.2% | 49.4% |

Example 8

Library Selection for 17/9 scFv

Figure 18:
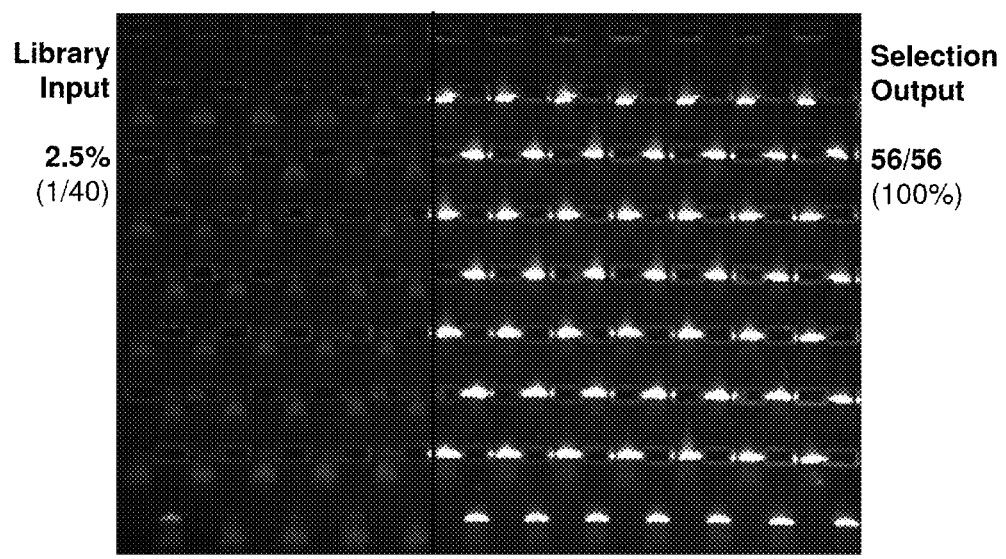
FIG. 18 depicts agarose gel electrophoresis results quantifying 17/9 scFv before and after one round of mRNA-scFv selection.

To demonstrate that an mRNA-scFv molecule can be enriched by several rounds of selection using the mRNA display methods described here, a scFv library with a diversity of 25 was constructed by overlapping PCR. To create the scFv library, equal amounts of the VH and VL fragments of 17/9, D2E7, 2SD4, Y61 and MAK195 were mixed and combined into a scFv library with a maximal diversity of 25 and used as described above. The 17/9 scFv was then selected from this library by biotinylated HA tag peptide. After selection, 17/9 enrichment was examined by cloning and colony PCR. The results quantifying 17/9 scFv before and after one round of mRNA-scFv selection are shown in FIG. 18. After one round of selection against HA peptide all scFv sequences recovered from the selection output were that of 17/9 scFv.

Example 9 mRNA Display Technology can be Used to Discriminate scFv Binders with Different Affinity To determine whether mRNA display technology, i.e., as described above, can be used to discriminate scFv binders with different affinity, chimeras between D2E7 and 2SD4 were made. 2SD4 is the D2E7 scFv precursor which exhibits low affinity (KD~200 nM as free protein) for TNFα. FIG. 19 depicts the chimeras.

Figure 20B:
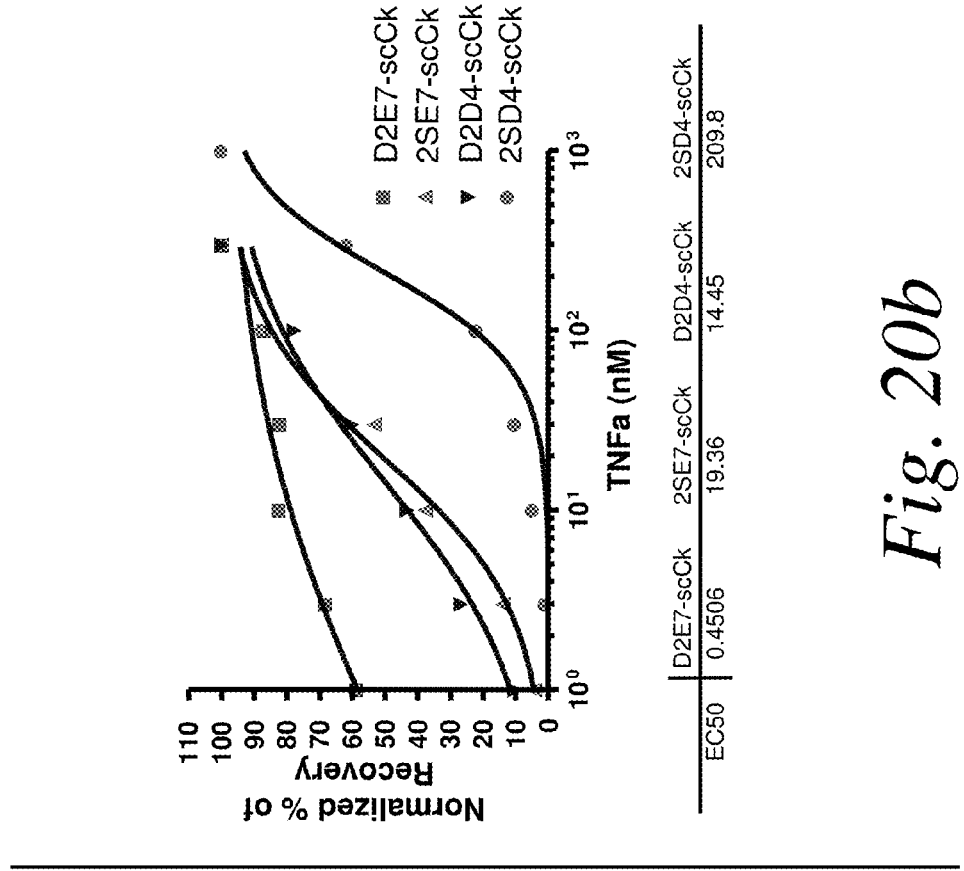
FIG. 20b depicts normalized percent of recovery after antigen selection, showing that mRNA display technology can be used to discriminate binders with different affinity.
Figure 20A:
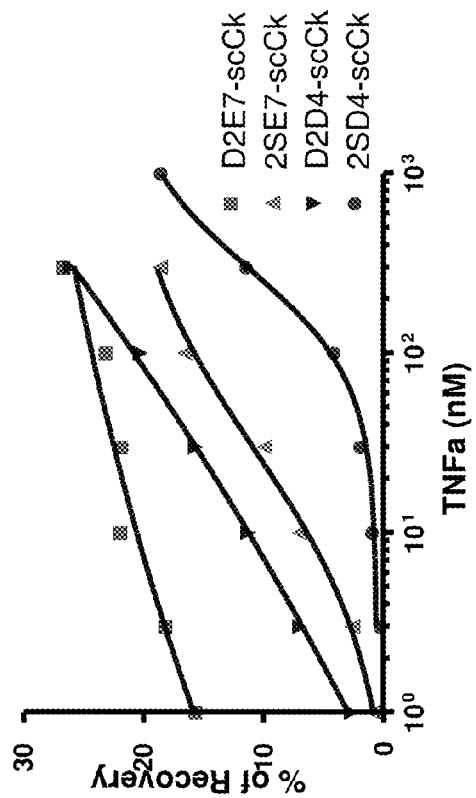
FIG. 20a depicts the percent of recovery after antigen binding between the different chimeras, showing that mRNA display technology can be used to discriminate binders with different affinity.

Titration was performed for free proteins. FIG. 20a shows the percent of recovery after antigen binding between the different chimeras, while FIG. 20b depicts the normalized percent of recovery after antigen selection. The above results show that mRNA display technology as described herein can be used to discriminate binders with different affinity.

Example 10

Thermostability of mRNA-scFv Molecules

Figure 21:
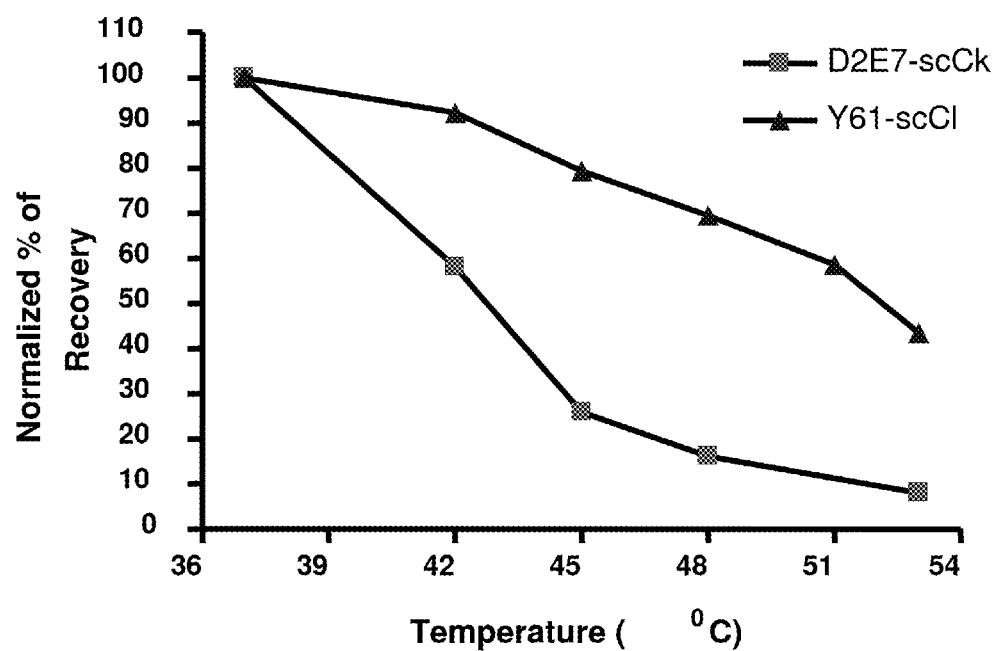
FIG. 21 depicts the thermostability of mRNA-scFv molecules.

To determine the thermostability of mRNA-scFv molecules, D2E7-scCk and Y61-scCk were translated and purified in mRNA-scFv format, as described herein. The mRNA-scFv molecules were then incubated at different temperatures for 30 minutes prior to antigen selection. The normalized percent of recovery after antigen selection is shown in FIG. 21.

Figure 22:
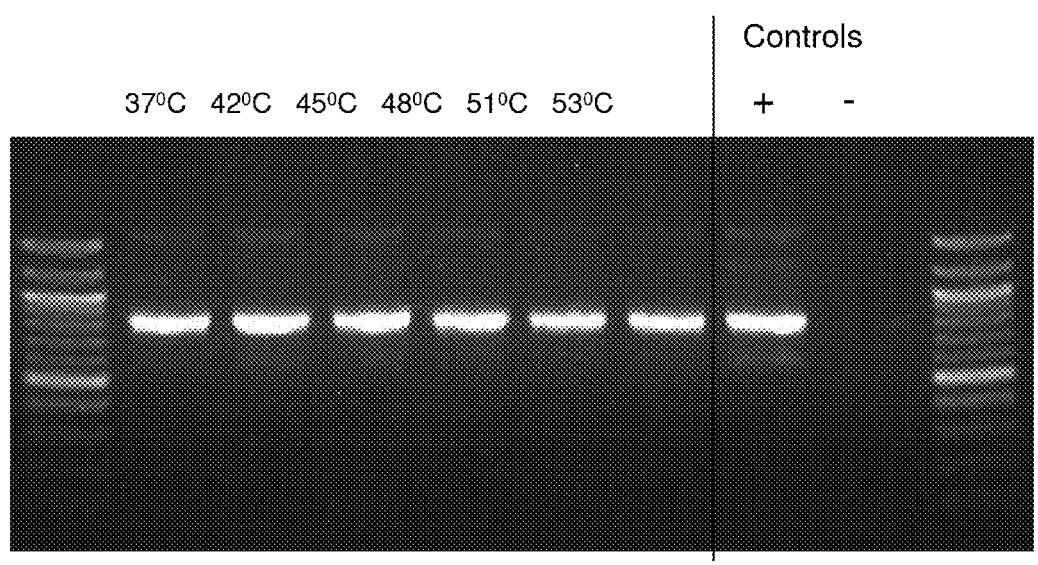
FIG. 22 depicts agarose gel electrophoresis results showing that RNA can be recovered after high temperature treatment of mRNA-scFv molecules.

FIG. 22 shows that RNA can be recovered after high temperature treatment of mRNA-scFv molecules. Here, RT-PCR was performed on the beads with recovered Y61-scCl mRNA-scFv molecules.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The practice of the present invention may employ, unless otherwise indicated, conventional techniques of cell culture and molecular biology, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

---

The invention claimed is:

1. A method of screening an scFv antibody RNA display library, the method comprising the steps of:
   (a) providing a library of puromycin or analogue thereof crosslinked single chain Fv (scFv) mRNA molecules, said molecules comprising an mRNA encoding a 5' scFv and a 3' spacer sequence, which molecules are crosslinked to a single stranded nucleic acid linker, the linker comprising a puromycin, or analogue thereof, at a 3' end and a Psoralen C6 at a 5' end;
   (b) in vitro translating the puromycin-crosslinked scFv mRNAs in the presence of a label under mildly oxidizing conditions using oxidized glutathione/reduced glutathione such that labeled puromycin-crosslinked scFv mRNA/protein molecules are formed;
   (c) purifying the labeled puromycin-crosslinked scFv mRNA/protein molecules;
   (d) screening the purified labeled puromycin-crosslinked scFv mRNA/protein molecules with at least one antigen; and
   (e) recovering the purified labeled puromycin-crosslinked scFv mRNA/protein molecules using magnetic beads; and optionally
   (f) reverse transcribing the scFv mRNA after antigen selection to make a cDNA that is complementary to the scFV mRNA.

2. The method of claim 1, further comprising the step of (g) amplifying the cDNA.

3. The method of claim 1, wherein the label is a radioactive label.

4. The method of claim 3, wherein the label is $^{35}$S methionine or cysteine.

5. The method of claim 1, wherein the 3' spacer sequence comprises about 200 amino acids.

6. The method of claim 1, wherein the 3' spacer sequence comprises about 16 amino acids.

7. The method of claim 1, wherein the 3' spacer sequence comprises an affinity tag.

8. The method of claim 1, wherein the nucleic acid linker comprises, from 5' to 3':
   Psoralen C6;
   2'OMe ribonucleotides comprising the sequence UAGCG-GAUGC (SEQ ID NO: 20);
   six Triethylene glycol or PEG-150 moieties;
   two deoxycytidine residues; and,
   Puromycin.

9. The method of claim 1, wherein the scFv mRNA molecules are photocrosslinked to the nucleic acid linker by UVA.

10. The method of claim 1, wherein the scFv mRNA molecules comprise a 5' promoter selected from the group consisting of T7, SP6, and T3.

11. The method of claim 1, wherein the scFv mRNA molecules comprise a tobacco mosaic virus 5' untranslated region.

12. The method of claim 1, wherein the labeled puromycin-crosslinked scFv mRNA/protein molecules are purified by oligodT chromatography.

13. The method of claim 1, wherein the labeled puromycin-crosslinked scFv mRNA/protein molecules are purified using anti-FLAG M2 monoclonal antibody agarose beads.

14. The method of claim 1, wherein the labeled puromycin-crosslinked scFv mRNA/protein molecules are purified by oligodT chromatography and anti-FLAG M2 monoclonal antibody agarose beads.

15. The method of claim 1, wherein the antigen is a biotinylated peptide, protein, or hapten.

16. The method of claim 1, wherein the antigen is a fusion protein with human immunoglobulin fragment crystallizable (Fc).

17. The method of claim 1, wherein the antigen is a fusion protein with murine immunoglobulin fragment crystallizable (Fc).

18. The method of claim 1, wherein the antigen is a population of cells.

19. The method of claim 1, wherein the antibody is an anti-IL-12 antibody.

20. The method of claim 1, wherein the antibody is an anti-HA antibody.

21. The method of claim 1, wherein the antibody is a murine antibody.

22. The method of claim 1, wherein the antibody is a human antibody.

23. The method of claim 1, wherein the antibody is a humanized antibody.

24. The method of claim 1, wherein in vitro translation of the puromycin-crosslinked scFv mRNA is additionally performed in the presence of protein disulphide isomerase (PDI).

25. The method of claim 1, wherein in vitro translation of the puromycin-crosslinked scFv mRNA is additionally performed in the absence of dithiothreitol.

26. The method of claim 1, wherein the method does not comprise an mRNA capping step.

27. The method of claim 1, wherein the method does not comprise an in vitro reverse transcription step prior to the purification step.

28. The method of claim 1, wherein an RNase inhibitor is added before, during, or after any of steps (a) through (g).

29. The method of claim 1, wherein said purification step comprises reverse transcription of the mRNA in the absence of dithiothreitol to produce a cDNA.

30. The method of claim 1 or 29, wherein the cDNA is eluted by alkaline hydrolysis at about pH=8.0 to about pH=10.0.

31. The method of claim 1 or 29, wherein the cDNA is eluted by heat.

32. The method of claim 1 or 29, wherein the cDNA is eluted by acid at about pH=3.0 to about pH=6.0.

33. The method of claim 29, wherein the cDNA is amplified by polymerase chain reaction.

34. The method of claim 33, wherein the polymerase chain reaction employs a thermostable DNA polymerase.

35. The method of claim 1, wherein the magnetic beads are selected from the group consisting of streptavidin beads and neutravidin beads.

* * * * *

SEQUENCE LISTING

```
<160> NUMBER OF SEQ ID NOS: 52

<210> SEQ ID NO 1
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Val Gln Leu Lys Glu Ser Gly Pro Gly Leu Val Ala Pro Ser
1               5                   10                  15

Gln Ser Leu Ser Ile Thr Cys Thr Val Ser Gly Phe Ser Leu Thr Asp
            20                  25                  30

Tyr Gly Val Asn Trp Val Arg Gln Pro Pro Gly Lys Gly Leu Glu Trp
        35                  40                  45

Leu Gly Met Ile Trp Gly Asp Gly Ser Thr Asp Tyr Asp Ser Thr Leu
    50                  55                  60

Lys Ser Arg Leu Ser Ile Ser Lys Asp Asn Ser Lys Ser Gln Ile Phe
65                  70                  75                  80

Leu Lys Met Asn Ser Leu Gln Thr Asp Asp Thr Ala Arg Tyr Tyr Cys
                85                  90                  95

Ala Arg Glu Trp His His Gly Pro Val Ala Tyr Trp Gly Gln Gly Thr
            100                 105                 110

Leu Val Thr Val Ser Ala Gly Gly Gly Ser Gly Gly Gly Gly Ser
        115                 120                 125

Gly Gly Gly Gly Ser Asp Ile Val Met Thr Gln Ser His Lys Phe Met
    130                 135                 140

Ser Thr Thr Val Gly Asp Arg Val Ser Ile Thr Cys Lys Ala Ser Gln
145                 150                 155                 160

Ala Val Ser Ser Ala Val Ala Trp Tyr Gln Gln Lys Pro Gly Gln Ser
                165                 170                 175

Pro Lys Leu Leu Ile Tyr Trp Ala Ser Thr Arg His Thr Gly Val Pro
            180                 185                 190

Asp Arg Phe Thr Gly Ser Gly Ser Val Thr Asp Phe Thr Leu Thr Ile
        195                 200                 205

His Asn Leu Gln Ala Glu Asp Leu Ala Leu Tyr Tyr Cys Gln Gln His
    210                 215                 220
```

```
Tyr Ser Thr Pro Phe Thr Phe Gly Ser Gly Thr Lys Leu Glu Ile Lys
225                 230                 235                 240

Arg Thr Val Ala Ala Pro Ser Val Phe Ile Phe Pro Pro Ser Asp Tyr
                245                 250                 255

Lys Asp Asp Asp Asp Lys Ala Ser Ala Ile
                260                 265

<210> SEQ ID NO 2
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gln Val Gln Leu Val Gln Ser Gly Gly Gly Val Val Gln Pro Gly
1               5                   10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Gly Lys Gly Leu Glu Trp
        35                  40                  45

Val Ala Phe Ile Arg Tyr Asp Gly Ser Asn Lys Tyr Tyr Ala Asp Ser
50                  55                  60

Val Lys Gly Arg Phe Thr Ile Ser Arg Asp Asn Ser Lys Asn Thr Leu
65                  70                  75                  80

Tyr Leu Gln Met Lys Ser Leu Arg Ala Glu Asp Thr Ala Val Tyr Tyr
                85                  90                  95

Cys Lys Thr His Gly Ser His Asp Asn Trp Gly Gln Gly Thr Met Val
            100                 105                 110

Thr Val Ser Ser Gly Gly Gly Ser Gly Gly Gly Gly Ser Gly Gly Gly
        115                 120                 125

Gly Gly Ser Ser Tyr Val Leu Thr Gln Pro Pro Ser Val Ser Gly Thr
    130                 135                 140

Pro Gly Gln Arg Val Thr Ile Ser Cys Ser Gly Gly Arg Ser Asn Ile
145                 150                 155                 160

Gly Ser Asn Thr Val Lys Trp Tyr Gln Gln Leu Pro Gly Thr Ala Pro
                165                 170                 175

Lys Leu Leu Ile Tyr Gly Asn Asp Gln Arg Pro Ser Gly Val Pro Asp
            180                 185                 190

Arg Phe Ser Gly Ser Lys Ser Gly Thr Ser Ala Ser Leu Ala Ile Thr
        195                 200                 205

Gly Val Gln Ala Glu Asp Glu Ala Asp Tyr Tyr Cys Gln Ser Tyr Asp
    210                 215                 220

Arg Gly Thr His Pro Ala Leu Leu Phe Gly Thr Gly Thr Lys Leu Thr
225                 230                 235                 240

Val Leu Gly Gln Pro Lys Ala Ala Pro Ser Val Thr Leu Asp Tyr Lys
                245                 250                 255

Asp Asp Asp Asp Lys Ala Ser Ala Ile
            260                 265

<210> SEQ ID NO 3
<211> LENGTH: 358
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 3

Met Gln Val Gln Leu Val Gln Ser Gly Gly Gly Val Gln Pro Gly
1               5                   10                  15

Arg Ser Leu Arg Leu Ser Cys Ala Ala Ser Gly Phe Thr Phe Ser
            20                  25                  30

Ser Tyr Gly Met His Trp Val Arg Gln Ala Pro Gly Lys Gly Leu Glu Trp
        35                  40                  45

Val Ala Phe Ile Arg Tyr Asp Gly Ser Asn Lys Tyr Tyr Ala Asp Ser
65  50                  55                  60

Val Lys Gly Arg Phe Thr Ile Ser Arg Asp Asn Ser Lys Asn Thr Leu
65                  70                  75                  80

Tyr Leu Gln Met Lys Ser Leu Arg Ala Glu Asp Thr Ala Val Tyr Tyr
                85                  90                  95

Cys Lys Thr His Gly Ser His Asp Asn Trp Gly Gln Gly Thr Met Val
                100                 105                 110

Thr Val Ser Ser Gly Gly Gly Ser Gly Gly Gly Ser Gly Gly
            115                 120                 125

Gly Gly Ser Ser Tyr Val Leu Thr Gln Pro Pro Ser Val Ser Gly Thr
130                 135                 140

Pro Gly Gln Arg Val Thr Ile Ser Cys Ser Gly Gly Arg Ser Asn Ile
145                 150                 155                 160

Gly Ser Asn Thr Val Lys Trp Tyr Gln Gln Leu Pro Gly Thr Ala Pro
                165                 170                 175

Lys Leu Leu Ile Tyr Gly Asn Asp Gln Arg Pro Ser Gly Val Pro Asp
                180                 185                 190

Arg Phe Ser Gly Ser Lys Ser Gly Thr Ser Ala Ser Leu Ala Ile Thr
                195                 200                 205

Gly Val Gln Ala Glu Asp Glu Ala Asp Tyr Tyr Cys Gln Ser Tyr Asp
210                 215                 220

Arg Gly Thr His Pro Ala Leu Leu Phe Gly Thr Gly Thr Lys Leu Thr
225                 230                 235                 240

Val Leu Gly Gln Pro Lys Ala Ala Pro Ser Val Thr Leu Phe Pro Pro
                245                 250                 255

Ser Ser Glu Glu Leu Gln Ala Asn Lys Ala Thr Leu Val Cys Leu Ile
                260                 265                 270

Ser Asp Phe Tyr Pro Gly Ala Val Thr Val Ala Trp Lys Ala Asp Ser
            275                 280                 285

Ser Pro Val Lys Ala Gly Val Glu Thr Thr Thr Pro Ser Lys Gln Ser
            290                 295                 300

Asn Asn Lys Tyr Ala Ala Ser Ser Tyr Leu Ser Leu Thr Pro Glu Gln
305                 310                 315                 320

Trp Lys Ser His Arg Ser Tyr Ser Cys Gln Val Thr His Glu Gly Ser
                325                 330                 335

Thr Val Glu Lys Thr Val Ala Pro Thr Glu Asp Tyr Lys Asp Asp Asp
                340                 345                 350

Asp Lys Ala Ser Ala Ile
            355

<210> SEQ ID NO 4
<211> LENGTH: 350
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 4

```
Met Gln Val Gln Leu Val Gln Ser Gly Gly Val Val Gln Pro Gly
1               5                   10                  15

Arg Ser Leu Arg Leu Ser Cys Ala Ala Ser Gly Phe Thr Phe Ser Ser
            20                  25                  30

Tyr Gly Met His Trp Val Arg Gln Ala Pro Gly Lys Gly Leu Glu Trp
        35                  40                  45

Val Ala Phe Ile Arg Tyr Asp Gly Ser Asn Lys Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Lys Ser Leu Arg Ala Glu Asp Thr Ala Val Tyr Tyr
                85                  90                  95

Cys Lys Thr His Gly Ser His Asp Asn Trp Gly Gln Gly Thr Met Val
            100                 105                 110

Thr Val Ser Ser Gly Gly Gly Ser Gly Gly Gly Ser Gly Gly
        115                 120                 125

Gly Gly Ser Ser Tyr Val Leu Thr Gln Pro Pro Ser Val Ser Gly Thr
130                 135                 140

Pro Gly Gln Arg Val Thr Ile Ser Cys Ser Gly Arg Ser Asn Ile
145                 150                 155                 160

Gly Ser Asn Thr Val Lys Trp Tyr Gln Gln Leu Pro Gly Thr Ala Pro
                165                 170                 175

Lys Leu Leu Ile Tyr Gly Asn Asp Gln Arg Pro Ser Gly Val Pro Asp
            180                 185                 190

Arg Phe Ser Gly Ser Lys Ser Gly Thr Ser Ala Ser Leu Ala Ile Thr
        195                 200                 205

Gly Val Gln Ala Glu Asp Glu Ala Asp Tyr Tyr Cys Gln Ser Tyr Asp
    210                 215                 220

Arg Gly Thr His Pro Ala Leu Leu Phe Gly Thr Gly Thr Lys Leu Thr
225                 230                 235                 240

Val Leu Gly Gln Pro Lys Ala Ala Pro Ser Val Thr Leu Pro Gln Pro
                245                 250                 255

Pro Val Asn Ala Gly Gly Gly Ser Gly Gly Gly Ser Gly Gly Gly Ser
            260                 265                 270

Glu Gly Gly Gly Ser Glu Gly Gly Ser Glu Gly Gly Ser Glu
        275                 280                 285

Gly Gly Gly Ser Gly Gly Ser Gly Ser Gly Asp Phe Asp Tyr Glu
    290                 295                 300

Lys Met Ala Asn Ala Asn Lys Gly Ala Met Thr Glu Asn Ala Asp Glu
305                 310                 315                 320

Asn Ala Leu Gln Ser Asp Ala Lys Gly Lys Leu Asp Ser Val Ala Thr
                325                 330                 335

Asp Tyr Asp Tyr Lys Asp Asp Asp Lys Ala Ser Ala Ile
            340                 345                 350
```

<210> SEQ ID NO 5
<211> LENGTH: 270
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 5

```
Met Glu Val Gln Leu Val Glu Ser Gly Gly Leu Val Gln Pro Gly
1               5                   10                  15

Arg Ser Leu Arg Leu Ser Cys Ala Ala Ser Gly Phe Thr Phe Asp Asp
            20                  25                  30

Tyr Ala Met His Trp Val Arg Gln Ala Pro Gly Lys Gly Leu Asp Trp
        35                  40                  45

Val Ser Ala Ile Thr Trp Asn Ser Gly His Ile Asp Tyr Ala Asp Ser
    50                  55                  60

Val Glu Gly Arg Phe Ala Val Ser Arg Asp Asn Ala Lys Asn Ala Leu
65                  70                  75                  80

Tyr Leu Gln Met Asn Ser Leu Arg Pro Glu Asp Thr Ala Val Tyr Tyr
                85                  90                  95

Cys Ala Lys Val Ser Tyr Leu Ser Thr Ala Ser Ser Leu Asp Tyr Trp
            100                 105                 110

Gly Gln Gly Thr Leu Val Thr Val Ser Ser Gly Gly Gly Ser Gly
            115                 120                 125

Gly Gly Gly Ser Gly Gly Gly Ser Asp Ile Gln Met Thr Gln Ser
130                 135                 140

Pro Ser Ser Leu Ser Ala Ser Ile Gly Asp Arg Val Thr Ile Thr Cys
145                 150                 155                 160

Arg Ala Ser Gln Gly Ile Arg Asn Tyr Leu Ala Trp Tyr Gln Gln Lys
                165                 170                 175

Pro Gly Lys Ala Pro Lys Leu Leu Ile Tyr Ala Ala Ser Thr Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Arg Tyr Asn Arg Ala Pro Tyr Thr Phe Gly Gln Gly Thr Lys
225                 230                 235                 240

Val Glu Ile Lys Arg Thr Val Ala Ala Pro Ser Val Phe Ile Phe Pro
                245                 250                 255

Pro Ser Asp Tyr Lys Asp Asp Asp Lys Ala Ser Ala Ile
            260                 265                 270
```

<210> SEQ ID NO 6
<211> LENGTH: 305
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 6

```
Met Glu Val Gln Leu Val Glu Ser Gly Gly Leu Val Gln Pro Gly
1               5                   10                  15

Arg Ser Leu Arg Leu Ser Cys Ala Ala Ser Gly Phe Thr Phe Asp Asp
            20                  25                  30

Tyr Ala Met His Trp Val Arg Gln Ala Pro Gly Lys Gly Leu Asp Trp
        35                  40                  45

Val Ser Ala Ile Thr Trp Asn Ser Gly His Ile Asp Tyr Ala Asp Ser
    50                  55                  60

Val Glu Gly Arg Phe Ala Val Ser Arg Asp Asn Ala Lys Asn Ala Leu
65                  70                  75                  80
```

```
Tyr Leu Gln Met Asn Ser Leu Arg Pro Glu Asp Thr Ala Val Tyr Tyr
                85                  90                  95

Cys Ala Lys Val Ser Tyr Leu Ser Thr Ala Ser Ser Leu Asp Tyr Trp
            100                 105                 110

Gly Gln Gly Thr Leu Val Thr Val Ser Ser Gly Gly Gly Gly Ser Gly
        115                 120                 125

Gly Gly Ser Gly Gly Gly Gly Ser Asp Ile Gln Met Thr Gln Ser
130                 135                 140

Pro Ser Ser Leu Ser Ala Ser Ile Gly Asp Arg Val Thr Ile Thr Cys
145                 150                 155                 160

Arg Ala Ser Gln Gly Ile Arg Asn Tyr Leu Ala Trp Tyr Gln Gln Lys
                165                 170                 175

Pro Gly Lys Ala Pro Lys Leu Leu Ile Tyr Ala Ala Ser Thr Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Arg Tyr Asn Arg Ala Pro Tyr Thr Phe Gly Gln Gly Thr Lys
225                 230                 235                 240

Val Glu Ile Lys Arg Thr Val Ala Ala Pro Ser Val Phe Ile Phe Pro
                245                 250                 255

Pro Ser Asp Glu Gln Leu Lys Ser Gly Thr Ala Ser Val Val Cys Leu
            260                 265                 270

Leu Asn Asn Phe Tyr Pro Arg Glu Ala Lys Val Gln Trp Lys Val Asp
        275                 280                 285

Asn Ala Leu Gln Ser Asp Tyr Lys Asp Asp Asp Lys Ala Ser Ala
    290                 295                 300

Ile
305

<210> SEQ ID NO 7
<211> LENGTH: 362
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Val Gln Leu Val Glu Ser Gly Gly Leu Val Gln Pro Gly
1               5                   10                  15

Arg Ser Leu Arg Leu Ser Cys Ala Ala Ser Gly Phe Thr Phe Asp Asp
                20                  25                  30

Tyr Ala Met His Trp Val Arg Gln Ala Pro Gly Lys Gly Leu Asp Trp
            35                  40                  45

Val Ser Ala Ile Thr Trp Asn Ser Gly His Ile Asp Tyr Ala Asp Ser
        50                  55                  60

Val Glu Gly Arg Phe Ala Val Ser Arg Asp Asn Ala Lys Asn Ala Leu
65                  70                  75                  80

Tyr Leu Gln Met Asn Ser Leu Arg Pro Glu Asp Thr Ala Val Tyr Tyr
                85                  90                  95

Cys Ala Lys Val Ser Tyr Leu Ser Thr Ala Ser Ser Leu Asp Tyr Trp
            100                 105                 110

Gly Gln Gly Thr Leu Val Thr Val Ser Ser Gly Gly Gly Gly Ser Gly
```

```
            115                 120                 125
Gly Gly Gly Ser Gly Gly Gly Ser Asp Ile Gln Met Thr Gln Ser
        130                 135                 140
Pro Ser Ser Leu Ser Ala Ser Ile Gly Asp Arg Val Thr Ile Thr Cys
145                 150                 155                 160
Arg Ala Ser Gln Gly Ile Arg Asn Tyr Leu Ala Trp Tyr Gln Gln Lys
                165                 170                 175
Pro Gly Lys Ala Pro Lys Leu Leu Ile Tyr Ala Ala Ser Thr Leu Gln
            180                 185                 190
Ser Gly Val Pro Ser Arg Phe Ser Gly Ser Gly Ser Gly Thr Asp Phe
        195                 200                 205
Thr Leu Thr Ile Ser Ser Leu Gln Pro Glu Asp Val Ala Thr Tyr Tyr
    210                 215                 220
Cys Gln Arg Tyr Asn Arg Ala Pro Tyr Thr Phe Gly Gln Gly Thr Lys
225                 230                 235                 240
Val Glu Ile Lys Arg Thr Val Ala Ala Pro Ser Val Phe Ile Phe Pro
                245                 250                 255
Pro Ser Asp Glu Gln Leu Lys Ser Gly Thr Ala Ser Val Val Cys Leu
            260                 265                 270
Leu Asn Asn Phe Tyr Pro Arg Glu Ala Lys Val Gln Trp Lys Val Asp
        275                 280                 285
Asn Ala Leu Gln Ser Gly Asn Ser Gln Glu Ser Val Thr Glu Gln Asp
    290                 295                 300
Ser Lys Asp Ser Thr Tyr Ser Leu Ser Ser Thr Leu Thr Leu Ser Lys
305                 310                 315                 320
Ala Asp Tyr Glu Lys His Lys Val Tyr Ala Cys Glu Val Thr His Gln
                325                 330                 335
Gly Leu Ser Ser Pro Val Thr Lys Ser Phe Asn Arg Gly Glu Asp Tyr
            340                 345                 350
Lys Asp Asp Asp Asp Lys Ala Ser Ala Ile
        355                 360

<210> SEQ ID NO 8
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Asp Trp Val
        35                  40                  45
Ser Ala Ile Thr Trp Asn Ser Gly His Ile Asp Tyr Ala Asp Ser Val
    50                  55                  60
Glu Gly Arg Phe Ala Val Ser Arg Asp Asn Ala Lys Asn Ala Leu Tyr
65                  70                  75                  80
Leu Gln Met Asn Ser Leu Arg Pro Glu Asp Thr Ala Val Tyr Tyr Cys
                85                  90                  95
Thr Lys Ala Ser Tyr Leu Ser Ser Ser Ser Leu Asp Asn Trp Gly
            100                 105                 110
```

```
Gln Gly Thr Leu Val Thr Val Ser Gly Gly Gly Ser Gly Gly
            115                 120                 125
Gly Gly Ser Gly Gly Gly Ser Asp Ile Gln Met Thr Gln Ser Pro
130                 135                 140
Ser Ser Leu Ser Ala Ser Ile Gly Asp Arg Val Thr Ile Thr Cys Arg
145                 150                 155                 160
Ala Ser Gln Gly Ile Arg Asn Tyr Leu Ala Trp Tyr Gln Lys Pro
            165                 170                 175
Gly Lys Ala Pro Lys Leu Leu Ile Tyr Ala Ala Ser Thr Leu Gln Ser
            180                 185                 190
Gly Val Pro Ser Arg Phe Ser Gly Ser Gly Ser Gly Thr Asp Phe Thr
            195                 200                 205
Leu Thr Ile Ser Ser Leu Gln Pro Glu Asp Val Ala Thr Tyr Tyr Cys
            210                 215                 220
Gln Lys Tyr Asn Ser Ala Pro Tyr Ala Phe Gly Gln Gly Thr Lys Val
225                 230                 235                 240
Glu Ile Lys Arg

<210> SEQ ID NO 9
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Val Gln Leu Val Glu Ser Gly Gly Asp Leu Val Lys Pro Gly
1               5                   10                  15
Gly Ser Leu Lys Leu Ser Cys Ala Ala Ser Gly Phe Ser Phe Ser Ser
            20                  25                  30
Tyr Gly Met Ser Trp Val Arg Gln Thr Pro Asp Lys Arg Leu Glu Trp
        35                  40                  45
Val Ala Thr Ile Ser Asn Gly Gly Tyr Thr Tyr Tyr Pro Asp Ser
50                  55                  60
Val Lys Gly Arg Phe Thr Ile Ser Arg Asp Asn Ala Lys Asn Thr Leu
65                  70                  75                  80
Tyr Leu Gln Met Ser Ser Leu Lys Ser Glu Asp Ser Ala Met Tyr Tyr
                85                  90                  95
Cys Ala Arg Arg Glu Arg Tyr Asp Glu Asn Gly Phe Ala Tyr Trp Gly
            100                 105                 110
Gln Gly Thr Leu Val Thr Val Ser Ala Gly Gly Gly Ser Gly Gly
            115                 120                 125
Gly Gly Ser Gly Gly Gly Ser Asp Ile Val Met Thr Gln Ser Pro
130                 135                 140
Ser Ser Leu Thr Val Thr Ala Gly Glu Lys Val Thr Met Ser Cys Thr
145                 150                 155                 160
Ser Ser Gln Ser Leu Phe Asn Ser Gly Lys Gln Lys Asn Tyr Leu Thr
            165                 170                 175
Trp Tyr Gln Gln Lys Pro Gly Gln Pro Pro Lys Val Leu Ile Tyr Trp
            180                 185                 190
Ala Ser Thr Arg Glu Ser Gly Val Pro Asp Arg Phe Thr Gly Ser Gly
            195                 200                 205
Ser Gly Thr Asp Phe Thr Leu Thr Ile Ser Ser Val Gln Ala Glu Asp
            210                 215                 220
```

-continued

| | | | | | | | | | | | |
|---|---|---|---|---|---|---|---|---|---|---|---|
| Leu | Ala | Val | Tyr | Tyr | Cys | Gln | Asn | Asp | Tyr | Ser | Asn Pro Leu Thr Phe |
| 225 | | | | 230 | | | | 235 | | | 240 |

Gly Gly Gly Thr Lys Leu Glu Leu Lys Arg Thr Val Ala Ala Pro Ser
            245                 250                 255

Val Phe Ile Phe Pro Pro Ser Asp Glu Gln Leu Lys Ser Gly Thr Ala
        260                 265                 270

Ser Val Val Cys Leu Leu Asn Asn Phe Tyr Pro Arg Glu Ala Lys Val
        275                 280                 285

Gln Trp Lys Val Asp Asn Ala Leu Gln Ser Gly Asn Ser Gln Glu Ser
    290                 295                 300

Val Thr Glu Gln Asp Ser Lys Asp Ser Thr Tyr Ser Leu Ser Ser Thr
305                 310                 315                 320

Leu Thr Leu Ser Lys Ala Asp Tyr Glu Lys His Lys Val Tyr Ala Cys
                325                 330                 335

Glu Val Thr His Gln Gly Leu Ser Ser Pro Val Thr Lys Ser Phe Asn
            340                 345                 350

Arg Gly Glu Asp Tyr Lys Asp Asp Asp Lys Ala Ser Ala Ile
        355                 360                 365

<210> SEQ ID NO 10
<211> LENGTH: 863
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
taatacgact cactataggg acaattacta tttacaatta caccatggag gtgcagctga    60
aggagtcagg acctggcctg gtggcgccct cacagagcct gtccatcaca tgcaccgtct   120
cagggttctc attaaccgac tatggtgtaa actgggttcg ccagcctcca ggaaagggtc   180
tggagtggct gggaatgata tggggtgatg gaagcacaga ctatgattca actctcaaat   240
ccagactgag catcagcaag gacaactcca agagccaaat tttcttaaaa atgaacagtc   300
tgcaaactga tgacacagcc aggtactact gtgccagaga atggcatcat ggccccgtcg   360
cttactgggg ccaagggact ctggtcactg tctctgcagg tggaggcggt tcaggcggag   420
gtggctctgg cggtggcgga tcggacattg tgatgaccca gtctcacaaa ttcatgtcca   480
caacagtagg agacagggtc agcatcacct gcaaggccag tcaggctgtg agttctgctg   540
tagcctggta tcaacaaaaa ccaggacaat ctcctaaact actgatttac tgggcatcca   600
cccggcacac tggagtccct gatcgcttca caggcagtgg atctgtgaca gattttactc   660
tcaccatcca caatttgcag gctgaagacc tggcacttta ttactgtcag caacattata   720
gcactccatt cacgttcggc tcggggacaa agttggaaat aaaacgtacg gtggctgcac   780
catctgtctt catcttcccg ccatctgact acaaggacga cgacgacaag gcatccgcta   840
tttaaaaaaa aaaaaaaaaa aaa                                           863
```

<210> SEQ ID NO 11
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
taatacgact cactataggg acaattacta tttacaatta caatgcaggt gcagctggtg      60
cagtctgggg gaggcgtggt ccagcctggg aggtccctga gactctcctg tgcagcgtct     120
ggattcacct tcagtagcta tggcatgcac tgggtccgcc aggctccagg caaggggctg     180
gagtgggtgg catttatacg gtatgatgga agtaataaat actatgcaga ctccgtgaag     240
ggccgattca ccatctccag agacaattcc aagaacacgc tgtatctgca aatgaaaagc     300
ctgagagctg aggacacggc tgtgtattac tgtaagaccc atggtagcca tgacaactgg     360
ggccaaggga caatggtcac cgtctcttca ggtggaggcg gttcaggcgg aggtggcagc     420
ggcggtggcg gatcgtccta tgtgctgact cagccccccT cagtgtctgg gaccccCggg     480
cagagagtca ccatctcttg ttctggaggc agatccaaca tcggcagtaa tactgtaaag     540
tggtatcagc agctcccagg aacggccccc aaactcctca tctatggcaa tgatcagcgg     600
ccctcagggg tccctgaccg attctctggc tccaagtctg gcacctcagc ctccctggct     660
atcactgggg tccaggctga agacgaggct gactattact gccagtcata tgacagaggc     720
acccaccccg ccctgctctt cggaactggg accaagctga ccgtcctagg tcaacccaag     780
gctgccccct cggtcactct ggactacaag gacgacgacg acaaggcatc cgctatttaa     840
aaaaaaaaaa aaaaaaaa                                                   858
```

<210> SEQ ID NO 12
<211> LENGTH: 1137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
taatacgact cactataggg acaattacta tttacaatta caatgcaggt gcagctggtg      60
cagtctgggg gaggcgtggt ccagcctggg aggtccctga gactctcctg tgcagcgtct     120
ggattcacct tcagtagcta tggcatgcac tgggtccgcc aggctccagg caaggggctg     180
gagtgggtgg catttatacg gtatgatgga agtaataaat actatgcaga ctccgtgaag     240
ggccgattca ccatctccag agacaattcc aagaacacgc tgtatctgca aatgaaaagc     300
ctgagagctg aggacacggc tgtgtattac tgtaagaccc atggtagcca tgacaactgg     360
ggccaaggga caatggtcac cgtctcttca ggtggaggcg gttcaggcgg aggtggcagc     420
ggcggtggcg gatcgtccta tgtgctgact cagccccccT cagtgtctgg gaccccCggg     480
cagagagtca ccatctcttg ttctggaggc agatccaaca tcggcagtaa tactgtaaag     540
tggtatcagc agctcccagg aacggccccc aaactcctca tctatggcaa tgatcagcgg     600
ccctcagggg tccctgaccg attctctggc tccaagtctg gcacctcagc ctccctggct     660
atcactgggg tccaggctga agacgaggct gactattact gccagtcata tgacagaggc     720
acccaccccg ccctgctctt cggaactggg accaagctga ccgtcctagg tcaacccaag     780
gctgccccct cggtcactct gttcccgccc tcctctgagg agcttcaagc caacaaggcc     840
acactggtgt gtctcataag tgacttctac ccgggagccg tgacagtggc ctggaaggca     900
gatagcagcc ccgtcaaggc gggagtggag accaccacac cctccaaaca agcaacaac     960 aagtacgcgg ccagcagcta cctgagcctg acgcctgagc agtggaagtc ccacagaagc    1020
tacagctgcc aggtcacgca tgaagggagc accgtggaga acagtggcc cctacagaa     1080 gactacaagg acgacgacga caaggcatcc gctatttaaa aaaaaaaaa aaaaaaa      1137
```

<210> SEQ ID NO 13
<211> LENGTH: 1113
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

| | |
|---|---|
| taatacgact cactataggg acaattacta tttacaatta caatgcaggt gcagctggtg | 60 |
| cagtctgggg gaggcgtggt ccagcctggg aggtccctga actctcctg tgcagcgtct | 120 |
| ggattcacct tcagtagcta tggcatgcac tgggtccgcc aggctccagg caaggggctg | 180 |
| gagtgggtgg catttatacg gtatgatgga agtaataaat actatgcaga ctccgtgaag | 240 |
| ggccgattca ccatctccag agacaattcc aagaacacgc tgtatctgca aatgaaaagc | 300 |
| ctgagagctg aggacacggc tgtgtattac tgtaagaccc atggtagcca tgacaactgg | 360 |
| ggccaaggga caatggtcac cgtctcttca ggtggaggcg gttcaggcgg aggtggcagc | 420 |
| ggcggtggcg gatcgtccta tgtgctgact cagcccccct cagtgtctgg gaccccgggg | 480 |
| cagagagtca ccatctcttg ttctggaggc agatccaaca tcggcagtaa tactgtaaag | 540 |
| tggtatcagc agctcccagg aacggccccc aaactcctca tctatggcaa tgatcagcgg | 600 |
| ccctcagggg tccctgaccg attctctggc tccaagtctg gcacctcagc ctccctggct | 660 |
| atcactgggg tccaggctga agacgaggct gactattact gccagtcata tgacagaggc | 720 |
| acccaccccg ccctgctctt cggaactggg accaagctga ccgtcctagg tcaacccaag | 780 |
| gctgccccct cggtcactct gcctcaacct cctgtcaatg ctggcggcgg ctctggtggt | 840 |
| ggttctggtg gcggctctga gggtggtggc tctgagggtg gcggttctga gggtggcggc | 900 |
| tctgagggag gcggttccgg tggtggctct ggttccggtg attttgatta tgaaaagatg | 960 |
| gcaaacgcta ataaggggc tatgaccgaa aatgccgatg aaaacgcgct acagtctgac | 1020 |
| gctaaaggca aacttgattc tgtcgctact gattacgatt acaaagacga tgacgataag | 1080 |
| gcatccgcta tttaaaaaaa aaaaaaaaaa aaa | 1113 |

<210> SEQ ID NO 14
<211> LENGTH: 1097
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

| | |
|---|---|
| taatacgact cactataggg acaattacta tttacaatta caatgcaggt gcagctggtg | 60 |
| cagtctgggg gaggcgtggt ccagcctggg aggtccctga actctcctg tgcagcgtct | 120 |
| ggattcacct tcagtagcta tggcatgcac tgggtccgcc aggctccagg caaggggctg | 180 |
| gagtgggtgg catttatacg gtatgatgga agtaataaat actatgcaga ctccgtgaag | 240 |
| ggccgattca ccatctccag agacaattcc aagaacacgc tgtatctgca aatgaaaagc | 300 |
| ctgagagctg aggacacggc tgtgtattac tgtaagaccc atggtagcca tgacaactgg | 360 |
| ggccaaggga caatggtcac cgtctcttca ggtggaggcg gttcaggcgg aggtggcagc | 420 |
| ggcggtggcg gatcgtccta tgtgctgact cagcccccct cagtgtctgg gaccccgggg | 480 |
| cagagagtca ccatctcttg ttctggaggc agatccaaca tcggcagtaa tactgtaaag | 540 |
| tggtatcagc agctcccagg aacggccccc aaactcctca tctatggcaa tgatcagcgg | 600 |

```
ccctcagggg tccctgaccg attctctggc tccaagtctg gcacctcagc ctccctggct      660
atcactgggg tccaggctga agacgaggct gactattact gccagtcata tgacagaggc      720
acccaccccg ccctgctctt cggaactggg accaagctga ccgtcctagg tcaacccaag      780
gctgccccct cggtcactct gcctcaacct cctgtcaatg ctggcggcgg ctctggtggt      840
ggttctggtg gcggctctga gggtggtggc tctgagggtg gcggttctga gggtggcggc      900
tctgagggag gcggttccgg tggtggctct ggttccggtg attttgatta tgaaaagatg      960
gcaaacgcta ataagggggc tatgaccgaa aatgccgatg aaaacgcgct acagtctgac     1020
gctaaaggca aacttgattc tgtcgctact gattacgatt acaaagacga tgacgataag     1080
gcatccgcta tttaaaa                                                    1097
```

```
<210> SEQ ID NO 15
<211> LENGTH: 876
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ttaatacgac tcactatagg gacaattact atttacaatt acaccatgga ggtgcagctg       60
gtggagtctg ggggaggctt ggtacagccc ggcaggtccc tgagactctc ctgtgcggcc      120
tctggattca ccctttgatga ttatgccatg cactgggtcc ggcaagctcc agggaagggc      180
ctggactggg tctcagctat cacttggaat agtggtcaca tagactatgc ggactctgtg      240
gagggccgat tcgccgtctc cagagacaac gccaagaacg ccctgtatct gcaaatgaac      300
agtctgagac tgaggacacg gcagtatat tactgtgcga aagtctcgta ccttagcacc      360
gcgtcctccc ttgactactg gggccaaggt accctggtca ccgtctcgag tggtggaggc      420
ggttcaggcg gaggtggctc tggcggtggc ggatcggaca tccagatgac ccagtctcca      480
tcctccctgt ctgcatctat aggggacaga gtcaccatca cttgtcgggc aagtcagggc      540
atcagaaatt acttagcctg gtatcagcaa aaaccaggga aagcccctaa gctcctgatc      600
tatgctgcat ccactttgca atcaggggtc ccatctcggt tcagtggcag tggatctggg      660
acagatttca ctctcaccat cagcagccta gcctgaag atgttgcaac ttattactgt      720
caaaggtata accgtgcccc gtacactttt ggccagggga ccaaggtgga aatcaaacgt      780
acggtggctg caccatctgt cttcatcttc ccgccatctg actacaagga cgacgacgac      840
aaggcatccg ctatttaaaa aaaaaaaaaa aaaaaa                                876
```

```
<210> SEQ ID NO 16
<211> LENGTH: 980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
taatacgact cactataggg acaattacta tttacaatta ccatggag gtgcagctgg        60 tggagtctgg gggaggcttg gtacagcccg gcaggtccct gagactctcc tgtgcggcct     120
ctggattcac ctttgatgat tatgccatgc actgggtccg gcaagctcca gggaagggcc     180
tggactgggt ctcagctatc acttggaata gtggtcacat agactatgcg gactctgtgg     240
```

```
agggccgatt cgccgtctcc agagacaacg ccaagaacgc cctgtatctg caaatgaaca      300
gtctgagacc tgaggacacg gcagtatatt actgtgcgaa agtctcgtac cttagcaccg      360
cgtcctccct tgactactgg ggccaaggta ccctggtcac cgtctcgagt ggtggaggcg      420
gttcaggcgg aggtggctct ggcggtggcg gatcggacat ccagatgacc cagtctccat      480
cctccctgtc tgcatctata ggggacagag tcaccatcac ttgtcgggca agtcagggca      540
tcagaaatta cttagcctgg tatcagcaaa aaccagggaa agcccctaag ctcctgatct      600
atgctgcatc cactttgcaa tcaggggtcc catctcggtt cagtggcagt ggatctggga      660
cagatttcac tctcaccatc agcagcctac agcctgaaga tgttgcaact tattactgtc      720
aaaggtataa ccgtgccccg tacacttttg gccagggac caaggtggaa atcaaacgta      780
cggtggctgc accatctgtc ttcatcttcc cgccatctga tgagcagttg aaatctggaa      840
ctgcctctgt tgtgtgcctg ctgaataact tctatcccag agaggccaaa gtacagtgga      900
aggtggataa cgccctccaa tcgggtaact cccaggagag tgtcacagag caggacagca      960
```

<210> SEQ ID NO 17
<211> LENGTH: 1151
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
taatacgact cactataggg acaattacta tttacaatta caccatggag gtgcagctgg      60
tggagtctgg gggaggcttg gtacagcccg gcaggtccct gagactctcc tgtgcggcct      120
ctggattcac ctttgatgat tatgccatgc actgggtccg gcaagctcca gggaagggcc      180
tggactgggt ctcagctatc acttggaata gtggtcacat agactatgcg gactctgtgg      240
agggccgatt cgccgtctcc agagacaacg ccaagaacgc cctgtatctg caaatgaaca      300
gtctgagacc tgaggacacg gcagtatatt actgtgcgaa agtctcgtac cttagcaccg      360
cgtcctccct tgactactgg ggccaaggta ccctggtcac cgtctcgagt ggtggaggcg      420
gttcaggcgg aggtggctct ggcggtggcg gatcggacat ccagatgacc cagtctccat      480
cctccctgtc tgcatctata ggggacagag tcaccatcac ttgtcgggca agtcagggca      540
tcagaaatta cttagcctgg tatcagcaaa aaccagggaa agcccctaag ctcctgatct      600
atgctgcatc cactttgcaa tcaggggtcc catctcggtt cagtggcagt ggatctggga      660
cagatttcac tctcaccatc agcagcctac agcctgaaga tgttgcaact tattactgtc      720
aaaggtataa ccgtgccccg tacacttttg gccagggac caaggtggaa atcaaacgta      780
cggtggctgc accatctgtc ttcatcttcc cgccatctga tgagcagttg aaatctggaa      840
ctgcctctgt tgtgtgcctg ctgaataact tctatcccag agaggccaaa gtacagtgga      900
aggtggataa cgccctccaa tcgggtaact cccaggagag tgtcacagag caggacagca      960
aggacagcac ctacagcctc agcagcaccc tgacgctgag caaagcagac tacgagaaac      1020
acaaagtcta cgcctgcgaa gtcacccatc agggcctgag ctcgcccgtc acaaagagct      1080
tcaacagggg agaggactac aaggacgacg acgacaaggc atccgctatt taaaaaaaaa      1140
aaaaaaaaaa a                                                          1151
```

<210> SEQ ID NO 18

| <211> LENGTH: 878 |
| --- |
| <212> TYPE: DNA |
| <213> ORGANISM: Artificial Sequence |
| <220> FEATURE: |
| <223> OTHER INFORMATION: Description of Artificial Sequence: Synthetic polynucleotide |

<400> SEQUENCE: 18

```
taatacgact cactataggg acaattacta tttacaatta caccatggaa gtgcagctgg      60
tggaaagcgg cggcgatctg gtgaaaccgg gcggcagcct gaaactgagc tgcgcggcga     120
gcggctttag ctttagcagc tatggcatga gctgggtgcg ccagaccccg ataaacgcc     180
tggaatgggt ggcgaccatt agcaacggcg gcggctatac ctattatccg gatagcgtga     240
aaggccgctt taccattagc gcgataacg cgaaaaacac cctgtatctg cagatgagca     300
gcctgaaaag cgaagatagc gcgatgtatt attgcgcgcg ccgcgaacgc tatgatgaaa     360
acggctttgc gtattggggc cagggcaccc tggtgaccgt gagcgcgggt ggaggcggtt     420
caggcggagg tggcagcggc ggtggcggat cggatattgt gatgacccag agcccgagca     480
gcctgaccgt gaccgcgggc gaaaaagtga ccatgagctg caccagcagc cagagcctgt     540
ttaacagcgg caaacagaaa aactatctaa cctggtatca gcagaaaccg gccagccgc     600
cgaaagtgct gatttattgg gcgagcaccc gcgaaagcgg cgtgccggat cgctttaccg     660
gcagcggcag cggcaccgat tttaccctga ccattagcag cgtgcaggcg aagatctgg     720
cggtgtatta ttgccagaac gattatagca acccgctgac ctttggcggc ggcaccaaac     780
tggaactgaa acgtacggtg gctgcaccat ctgtcttcat cgactacaag gacgacgacg     840
acaaggcatc cgctatttaa aaaaaaaaa aaaaaaaa                               878
```

<210> SEQ ID NO 19
<211> LENGTH: 1166
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 19

```
taatacgact cactataggg acaattacta tttacaatta caccatggaa gtgcagctgg      60
tggaaagcgg cggcgatctg gtgaaaccgg gcggcagcct gaaactgagc tgcgcggcga     120
gcggctttag ctttagcagc tatggcatga gctgggtgcg ccagaccccg ataaacgcc     180
tggaatgggt ggcgaccatt agcaacggcg gcggctatac ctattatccg gatagcgtga     240
aaggccgctt taccattagc gcgataacg cgaaaaacac cctgtatctg cagatgagca     300
gcctgaaaag cgaagatagc gcgatgtatt attgcgcgcg ccgcgaacgc tatgatgaaa     360
acggctttgc gtattggggc cagggcaccc tggtgaccgt gagcgcgggt ggaggcggtt     420
caggcggagg tggcagcggc ggtggcggat cggatattgt gatgacccag agcccgagca     480
gcctgaccgt gaccgcgggc gaaaaagtga ccatgagctg caccagcagc cagagcctgt     540
ttaacagcgg caaacagaaa aactatctaa cctggtatca gcagaaaccg gccagccgc     600
cgaaagtgct gatttattgg gcgagcaccc gcgaaagcgg cgtgccggat cgctttaccg     660
gcagcggcag cggcaccgat tttaccctga ccattagcag cgtgcaggcg aagatctgg     720
cggtgtatta ttgccagaac gattatagca acccgctgac ctttggcggc ggcaccaaac     780
tggaactgaa acgtacggtg gctgcaccat ctgtcttcat cttcccgcca tctgatgagc     840
agttgaaatc tggaactgcc tctgttgtgt gcctgctgaa taacttctat cccagagagg     900
```

```
ccaaagtaca gtggaaggtg gataacgccc tccaatcggg taactcccag gagagtgtca      960
cagagcagga cagcaaggac agcacctaca gcctcagcag caccctgacg ctgagcaaag     1020
cagactacga gaaacacaaa gtctacgcct gcgaagtcac ccatcagggc ctgagctcgc     1080
ccgtcacaaa gagcttcaac aggggagagg actacaagga cgacgacgac aaggcatccg     1140
ctatttaaaa aaaaaaaaaa aaaaaa                                          1166
```

<210> SEQ ID NO 20
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20

```
uagcggaugc                                                              10
```

<210> SEQ ID NO 21
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21

```
uagcggaugc aaaaaaaaaa aaaaaaaa                                          28
```

<210> SEQ ID NO 22
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
taatacgact cactataggg acaattacta tttacaatta caccatggag gtgcagctga       60
aggagtcagg                                                              70
```

<210> SEQ ID NO 23
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
cgatccgcca ccgccagagc cacctccgcc tgaaccgcct ccacctgcag agacagtgac       60
cagagtcc                                                                68
```

<210> SEQ ID NO 24
<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
ggtggaggcg gttcaggcgg aggtggctct ggcggtggcg gatcggacat tgtgatgacc       60
``` cagtctc                                                              67

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gatggtgcag ccaccgtacg ttttatttcc aactttgtcc ccgag                    45

<210> SEQ ID NO 26
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggacaattac tatttacaat tacaccatgg aagtgcagct ggtggaaagc ggcggcgatc    60
tggtgaaacc                                                           70

<210> SEQ ID NO 27
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctgctaaag ctaaagccgc tcgccgcgca gctcagtttc aggctgccgc ccggtttcac    60
cagatcgccg                                                           70

<210> SEQ ID NO 28
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ggctttagct ttagcagcta tggcatgagc tgggtgcgcc agaccccgga taaacgcctg    60
gaatgggtgg                                                           70

<210> SEQ ID NO 29
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcctttcacg ctatccggat aataggtata gccgccgccg ttgctaatgg tcgccaccca    60
ttccaggcgt                                                           70

<210> SEQ ID NO 30
<211> LENGTH: 69

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccggatagcg tgaaaggccg ctttaccatt agccgcgata acgcgaaaaa caccctgtat    60
ctgcagatg                                                            69

<210> SEQ ID NO 31
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gttcgcggcg cgcgcaataa tacatcgcgc tatcttcgct tttcaggctg ctcatctgca    60
gatacagggt                                                           70

<210> SEQ ID NO 32
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
attgcgcgcg ccgcgaacgc tatgatgaaa acggctttgc gtattggggc cagggcaccc    60
tggtgaccgt                                                           70

<210> SEQ ID NO 33
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgatccgcca ccgccgctgc cacctccgcc tgaaccgcct ccacccgcgc tcacggtcac    60
cagggtgccc                                                           70

<210> SEQ ID NO 34
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agcggcggtg gcggatcgga tattgtgatg acccagagcc cgagcagcct gaccgtgacc    60
gcgggcgaaa                                                           70

<210> SEQ ID NO 35
<211> LENGTH: 70
<212> TYPE: DNA
<213> ORGANISM: Artificial Sequence
<220> FEATURE:
<223> OTHER INFORMATION: Description of Artificial Sequence: Synthetic
```

```
                                     primer

<400> SEQUENCE: 35
tgtttgccgc tgttaaacag gctctggctg ctggtgcagc tcatggtcac tttttcgccc      60
gcggtcacgg                                                             70

<210> SEQ ID NO 36
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtttaacagc ggcaaacaga aaaactatct gacctggtat cagcagaaac cgggccagcc      60
gccgaaagtg                                                             70

<210> SEQ ID NO 37
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cggtaaagcg atccggcacg ccgctttcgc gggtgctcgc ccaataaatc agcactttcg      60
gcggctggcc                                                             70

<210> SEQ ID NO 38
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tgccggatcg ctttaccggc agcggcagcg gcaccgattt taccctgacc attagcagcg      60
tgcaggcgga                                                             70

<210> SEQ ID NO 39
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aaaggtcagc gggttgctat aatcgttctg gcaataatac accgccagat cttccgcctg      60
cacgctgcta                                                             70

<210> SEQ ID NO 40
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
```

```
agcaacccgc tgacctttgg cggcggcacc aaactggaac tgaaacgtac ggtggctgca    60
ccatctgtct                                                           70
```

<210> SEQ ID NO 41
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
ttaaatagcg gatgccttgt cgtcgtcgtc cttgtagtcg atgaagacag atggtgcagc    60
cacc                                                                 64
```

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Arg Thr Val Ala Ala Pro Ser Val Phe Ile Phe Pro Pro Ser
1               5                   10
```

<210> SEQ ID NO 43
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser
```

<210> SEQ ID NO 44
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

```
            65                  70                  75                  80
Lys His Lys Val Tyr Ala Cys Glu Val Thr His Gln Gly Leu Ser Ser
                85                  90                  95

Pro Val Thr Lys Ser Phe Asn Arg Gly Glu
            100                 105
```

<210> SEQ ID NO 45
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 45
gtcgtcgtcg tccttgtagt cgaagacaga tggtgcagcc acagttcg         48

<210> SEQ ID NO 46
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 46
tttttttttt tttttttttt aaatagcgga tgccttgtcg tcgtcgtcct tgtagtcgaa    60
gacagatggt gcagccaca                                                 79

<210> SEQ ID NO 47
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 47
gtcgtcgtcg tccttgtagt cagtgacagt ggggttggcc ttgggctgac ckaggacggt    60

<210> SEQ ID NO 48
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 48
tttttttttt tttttttttt aaatagcgga tgccttgtcg tcgtcgtcct tgtagtcagt    60
gacagtgggg ttggccttg                                                 79

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
cgctacctcc gccgccagac                                                20

<210> SEQ ID NO 50
<211> LENGTH: 76
<212> TYPE: DNA
<213> ORGANISM: Artificial Sequence
<220> FEATURE:
<223> OTHER INFORMATION: Synthetic oligonucleotide

```
<400> SEQUENCE: 50
tttttttttt tttttttttt aaatagcgga tgctttgtca tcatcatctt tataatcgct      60
acctccgccg ccagac                                                     76

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51
gacacggccg tgtattactg t                                               21

<210> SEQ ID NO 52
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 52
gctgaggaga cggtgacc                                                   18
```